United States Patent
Radjy

(10) Patent No.: US 11,815,505 B2
(45) Date of Patent: Nov. 14, 2023

(54) SENSOR DEVICE, AND SYSTEMS AND METHODS FOR OBTAINING AND PROVIDING INFORMATION RELATING TO CONCRETE MIXTURES AND CONSTRUCTION PROJECTS

(71) Applicant: QUIPIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 433 days.

(21) Appl. No.: 16/141,369

(22) Filed: Sep. 25, 2018

(65) Prior Publication Data

US 2019/0101522 A1    Apr. 4, 2019

Related U.S. Application Data

(60) Provisional application No. 62/565,242, filed on Sep. 29, 2017.

(51) Int. Cl.
*G01N 33/38* (2006.01)
*E04B 1/16* (2006.01)
(Continued)

(52) U.S. Cl.
CPC ............. *G01N 33/383* (2013.01); *E04B 1/16* (2013.01); *E04B 5/32* (2013.01); *E04B 5/38* (2013.01);
(Continued)

(58) Field of Classification Search
CPC ........ G01N 33/383; G01N 29/00; E04B 1/16; E04B 5/32; E04B 5/38; E04B 2103/02; E04B 2005/322; E01C 23/01
See application file for complete search history.

(56) References Cited

U.S. PATENT DOCUMENTS

2007/0046479 A1 * 3/2007 Hines ................. G01N 29/2481
340/584
2012/0161789 A1   6/2012 Girlando et al.
(Continued)

FOREIGN PATENT DOCUMENTS

WO    2011/103039 A1    8/2011

OTHER PUBLICATIONS

Giatec SmartRock. Smart rock Waterproof Wireless Sensor for Temperature and Maturity Monitoring for Concrete Pours. Mar. 2017.*

(Continued)

*Primary Examiner* — Hyun D Park
*Assistant Examiner* — Lynda Dinh
(74) *Attorney, Agent, or Firm* — Lucas & Mercanti, LLP

(57) ABSTRACT

A plurality of sensor devices are placed at a plurality of locations at which concrete is to be poured, wherein each sensor device is adapted to measure humidity. For example, the plurality of sensors may be placed at selected locations within a form at a construction site associated with a construction project. Concrete is poured at the plurality of locations. Data representing humidity measurements is received from the plurality of sensor devices. For each of the plurality of sensor devices, a respective spike in humidity and a respective time associated with the spike in humidity are determined, thereby determining a plurality of spikes in humidity and a plurality of corresponding times. A build rate is determined for the construction project based on the plurality of spikes in humidity and a plurality of corresponding times.

4 Claims, 66 Drawing Sheets

(51) Int. Cl.
E04B 5/32 (2006.01)
E04B 5/38 (2006.01)
G01N 29/00 (2006.01)
E01C 23/01 (2006.01)

(52) U.S. Cl.
CPC .............. G01N 29/00 (2013.01); *E01C 23/01* (2013.01); *E04B 2005/322* (2013.01); *E04B 2103/02* (2013.01)

(56) References Cited

U.S. PATENT DOCUMENTS

| | | | |
|---|---|---|---|
| 2015/0014300 A1* | 1/2015 | Ciuperca | H05B 1/0227 219/494 |
| 2015/0355160 A1* | 12/2015 | Berman | G01N 11/14 73/54.03 |
| 2016/0018383 A1* | 1/2016 | Radjy | G01N 33/383 73/53.01 |
| 2016/0328929 A1* | 11/2016 | Jesus De Sequeira Serra Nunes | G08B 5/36 |
| 2017/0016874 A1* | 1/2017 | Radjy | B28C 7/024 |
| 2017/0146487 A1 | 5/2017 | Pagani | |
| 2017/0284996 A1* | 10/2017 | Ghods | B28C 7/02 |

OTHER PUBLICATIONS www.paconstructors.org, P-b0700402-B, Section 704—Cement Concrete, 2016.*

International Search Report and Written Opinion dated Dec. 27, 2018 from corresponding International Application No. PCT/US2018/052877.

* cited by examiner

STRUCTURE ID: SER-12 — 4111
COMPONENT: LEVEL 3 — 4113

STATISTICS
STRENGTH: 5000 PSI — 4221
TIME USED: 80 HOURS — 4222
COST OF COMPONENT: $ XXX — 4223
COST OF STRUCTURE (CUMULATIVE): $ YYY — 4224
BUILD RATE: 6 FEET/HOUR — 4225

BACK — 4255

SENSOR DEVICE, AND SYSTEMS AND METHODS FOR OBTAINING AND PROVIDING INFORMATION RELATING TO CONCRETE MIXTURES AND CONSTRUCTION PROJECTS

CROSS REFERENCE TO RELATED APPLICATION

This application claims priority from U.S. Provisional Application No. 62/565,242 filed Sep. 29, 2017, the contents of which are incorporated herein by reference.

TECHNICAL FIELD

This specification relates generally to the construction field, and more particularly to sensor devices, and systems and methods for obtaining and providing information relating to concrete mixtures and construction projects.

BACKGROUND

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement (cement and water which hardens into a solid mass upon aging).

In the construction field, after a batch of concrete has been produced for use at a particular site, it is useful to be able to obtain data concerning certain performance characteristics such as the in-place strength of the batch, maturity, and other characteristics. Accurate prediction of concrete performance can increase the quality of the end product, and can provide other benefits such as allowing the use of accelerated construction schedules.

Several methods for testing and monitoring; in-place strength of a concrete mass have been incorporated into the American Standard. Testing Methods, including ASTM C805 (The Rebound Number Method—the so-called Swiss Hammer Method), ASTM C597 (The Pulse Velocity (Sonic) Method), and ASTM C900 (The Pullout Strength Method).

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens.

In accordance with the standards, typically 4×8-inch or 6×12-inch test cylinders are used, and the concrete specimens are stored in a carefully selected location for a predetermined period of time. When making cylinders for acceptance of concrete, the field technician must test properties of the fresh concrete including temperature, slump, density (unit weight) and air content.

SUMMARY

In accordance with an embodiment, a sensor device includes a housing, the housing having an opening allowing substances to pass from an exterior of the housing to an interior of the housing, a printed circuit board disposed in the housing, the printed circuit board including a humidity sensor and at least one electronic component, a tube having a first end and a second end, the tube comprising a waterproof material, wherein the first end of the tube surrounds the humidity sensor, wherein a first seal is formed by between the first end of the tube and the printed circuit board, wherein the second end of the tube is located proximate the hole, and a material layer disposed between the second end of the tube and the hole, wherein the material layer comprises a waterproof and breathable material, wherein a second seal is formed between the material layer and the housing, wherein a third seal is formed between the material layer and the second end of the tube. The hole and the material layer allow water vapor to pass from the exterior to the humidity sensor. The first seal, the second seal, and the third seal prevent the water vapor from reaching the at least one electronic component.

In one embodiment, the printed circuit board further comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In another embodiment, the printed circuit board further includes a transmitter.

In another embodiment, the tube comprises one of plastic and rubber.

In another embodiment, the tube has a diameter of between 0.25 cm and 1.0 cm.

In accordance with another embodiment, a sensor device includes a housing, the housing having an opening that allows water vapor to pass between an exterior of the housing and an interior of the housing but prevents liquid from passing between the exterior and the interior. The sensor device also includes a printed circuit board disposed in the housing, the printed circuit board including a humidity sensor adapted to obtain humidity measurements, one or more second sensors adapted to obtain measurement data, and a processor adapted to: detect a change in the humidity measurements from a first level to a second level, activate the one or more second sensors in response to the change in the humidity measurements, and a transmitter adapted to transmit the humidity measurements and the measurement data.

In one embodiment, the opening comprises a hole in the housing, the hole having a diameter between 0.5 millimeters and 1.0 millimeter.

In another embodiment, the housing comprises a first portion and a second portion, the first and second portions being engaged, and the opening is disposed between the first and second portions.

In another embodiment, the printed circuit board further comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In accordance with another embodiment, a method is described. The method includes detecting, by a sensing device, a first humidity level representing a humidity of a first environment, embedding the sensing device within a concrete mixture, detecting, by the sensing device, a second humidity level associated with the concrete mixture, determining a change in humidity between the first humidity level and the second humidity level, and activating a selected component of the sensing device in response to detection of the change in humidity.

In one embodiment, the selected component comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In accordance with another embodiment, a sensor device is provided. The sensor device includes a housing, the housing having a hole allowing substances to pass from an exterior of the housing to an interior of the housing, a printed circuit board disposed in the housing, the printed circuit board including one of a temperature sensor and a humidity sensor, a material layer disposed between the hole and the printed circuit board, wherein the material layer comprises a waterproof and breathable material, and a support element disposed between the printed circuit board and the material layer, the support element adapted to separate the printed circuit board and the material layer. The hole and the material layer allow water vapor to pass from the exterior to the interior of the housing.

In accordance with another embodiment, a sensor device includes a humidity sensor. Before being placed into a concrete mixture, selected components of the sensor device (such as a temperature sensor, a pH sensor, a motion sensor, an accelerometer, etc.) are deactivated. The humidity sensor obtains humidity measurements, and the humidity measurement data is monitored by a processor. At the time when the sensor is inserted into a concrete mixture, the processor detects a change in the humidity measurements. For example, a spike in humidity may be detected. In response to the change in humidity, one or more components of the sensor device are activated. For example, other sensors may be activated in order to obtain measurements of temperature and other characteristics of the concrete mixture.

In accordance with another embodiment, a sensor device includes a sonic sensor adapted to measure sonic signals (sound waves). Before being placed into a concrete mixture, selected components of the sensor device (such as a temperature sensor, a pH sensor, a motion sensor, an accelerometer, etc.) are deactivated. The sonic sensor obtains measurements of sonic signals around the sensor device, and the sonic signal measurement data is monitored by a processor. At the time when the sensor is inserted into a concrete mixture, the processor detects a change in the strength of the sonic signal. For example, after the sensor is inserted into the concrete mixture, a signal loss may be detected as sonic signals (sound waves) are blocked by the concrete mixture. In response to the change in the strength of the sonic signal, one or more components of the sensor device are activated.

In one embodiment, components of a sensor device, such as the housing and other parts, may be formed of a thermosetting resin or a thermoplastic.

In one embodiment, a sensor device (such as any of those described herein) may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth ($3/16$) inches.

In accordance with an embodiment, a method is provided. A plurality of sensor devices are placed at a plurality of locations at which concrete is to be poured, wherein each sensor device is adapted to measure humidity. Concrete is poured at the plurality of locations. Data representing humidity measurements is received from the plurality of sensor devices. For each of the plurality of sensor devices, a respective spike in humidity and a respective time associated with the spike in humidity are determined, thereby determining a plurality of spikes in humidity and a plurality of corresponding times. A build rate is determined for the construction project based on the plurality of spikes in humidity and a plurality of corresponding times.

In one embodiment, the plurality of sensors are placed in a form located at a construction site.

In another embodiment, the form is associated with a component of a multi-level structure.

In another embodiment, the plurality of sensors are placed on a roadway.

In another embodiment, a build rate is determined based on a distance between first and second sensor devices and a time difference between a first humidity spike detected by the first sensor device and a second humidity spike detected by the second sensor device.

In another embodiment, the plurality of locations are associated with a construction project. A user device is caused to display, on a display device, a graphical representation of a structure associated with the construction project and a value representing a build rate.

In another embodiment, each sensor device is further adapted to measure acceleration. Second data representing acceleration measurements is received from the plurality of sensor devices. A build rate is determined for the construction project based on the plurality of spikes in humidity, a plurality of corresponding times, and the second data.

In accordance with another embodiment, a method is provided. A sensor device is placed at a location at which a concrete mixture is to be poured, wherein the sensor device is adapted to measure humidity. Concrete is poured at the location. Data representing humidity measurements are received from the sensor device. A spike in the humidity measurements is detected. A time associated with the spike is determined. The first data and the time are stored in a memory.

In one embodiment, at least one component of the sensor device is activated in response to detecting the spike in humidity measurements.

In another embodiment, a sensor device is placed in a form at a construction site.

In another embodiment, a sensor device is placed on a roadway.

In another embodiment, a build rate is determined based at least on the time associated with the spike.

In another embodiment, the location is associated with a construction project. A user device is caused to display, on a display device, a graphical representation of a structure associated with the construction project and a value representing the build rate.

In another embodiment, the sensor device is further adapted to measure acceleration. Second data representing acceleration measurements are received from the sensor device. A build rate is determined for the construction project based on the time associated with the spike and the second data.

In accordance with an embodiment, a method is provided. A plurality of sensor devices are placed at a plurality of locations at which a concrete mixture is to be poured, wherein each sensor device is adapted to measure a characteristic related to the concrete mixture. The concrete mixture is poured at the plurality of locations. Data representing measurements of the characteristic are received from the plurality of sensor devices. For each of the plurality of sensor devices, a respective change in the characteristic and a respective time associated with the change are determined, thereby determining a plurality of changes and a plurality of corresponding times. A build rate for the construction project is determined based on the plurality of changes and a plurality of corresponding times.

The characteristic may be humidity, temperature, or a decibel level of a signal.

In one embodiment, the characteristic is humidity, and the change is a spike in humidity measurements.

In another embodiment, the characteristic is a decibel level of a signal, and the change is a decrease in the decibel level of the signal.

These and other advantages of the present disclosure will be apparent to those of ordinary skill in the art by reference to the following Detailed Description and the accompanying drawings.

BRIEF DESCRIPTION OF THE DRAWINGS

FIG. 42 shows a page displaying information relating to a selected portion or component of a structure in accordance with an embodiment.

DETAILED DESCRIPTION

It has been observed that embedding sensors into a concrete mixture can be a useful method for obtaining certain measurements relating to the concrete mixture. For example, embedding a temperature sensor in a concrete mixture can facilitate the gathering of temperature data, which can be useful in predicting the strength or maturity of the concrete mixture. Similarly, embedding a humidity sensor in a concrete mixture can facilitate the gathering of humidity data, which can also be useful in predicting the strength or maturity of the concrete mixture. When embedded in a concrete mixture, it is preferable that a humidity sensor be directly exposed to the water vapor within the concrete in order to directly measure the humidity of the concrete.

However, it has been observed that many types of sensors, such as temperature sensors, motion sensors, etc., are susceptible to damage when exposed to humidity. In addition, any electronics in a sensor may also be damaged by humidity. Therefore, it is often preferable to provide a protective seal for certain sensors (e.g., temperature sensors, motion sensors, etc.) and for any electronics on a sensor before embedding such sensors into a concrete mixture.

Accordingly, there is a need for improved systems, apparatus, and methods for embedding a humidity sensor into a concrete mixture in a manner that exposes the humidity sensor to the humidity of the concrete mixture, while protecting any electronic circuitry on the sensor, and any other attached sensors from exposure to the humidity of the concrete.

Figure 1:
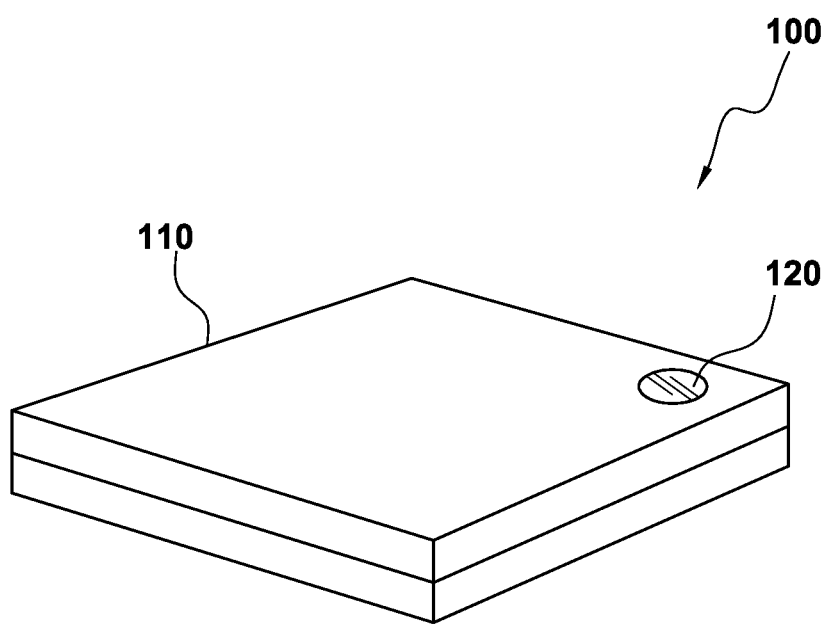
FIG. 1 shows a sensor in accordance with an embodiment.

FIG. 1 shows a sensor 100 in accordance with an embodiment. Sensor 100 includes a housing 110. Housing 110 includes a hole 120.

Figure 2:
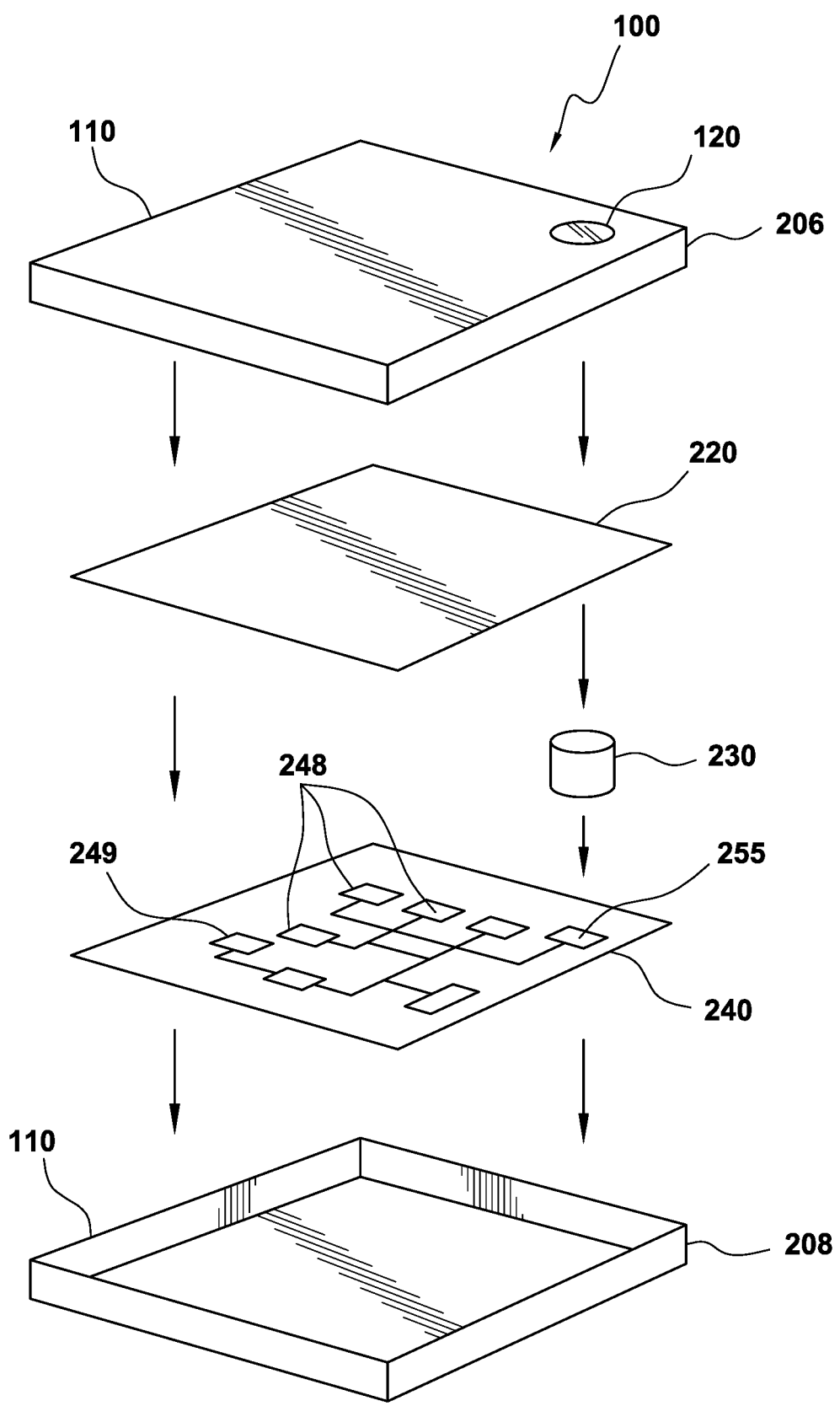
FIG. 2 shows components of the sensor of FIG. 1.

FIG. 2 shows components of the sensor of FIG. 1. Sensor 100 includes upper portion 206 and lower portion 208 of housing 110. Housing 110 may comprise plastic, metal, or other suitable material. Sensor may have a width between 0.5 inch and 3 inches, for example. Other dimensions may be used.

Sensor 100 also includes a layer 220 of waterproof material, a protective tube 230, and a printed circuit board (PCB) 240. PCB 240 includes a plurality of elements 248, which may include circuit components such as resistors, capacitors, amplifiers, etc., and/or one or more sensors adapted to obtain measurements relating to one or more characteristics such as temperature, motion, etc. For example, PCB 240 may include one or more of the following: a temperature sensor, a salinity sensor, a conductivity sensor, a motion sensor, a pH sensor, an acceleration sensor (accelerometer), a sonic sensor, etc. PCB 240 also includes a transceiver 249, which may include an antenna capable of sending and receiving data via wireless communication, for example. PCB 240 also includes a humidity sensor 255. PCB 240 may also include a location sensor (e.g., with GPS functionality). PCB 240 may also include a battery or other power source.

PCB 240 fits into bottom portion 208. Tube 230 fits onto and over humidity sensor 255. A first end of tube that contacts PCB 240 surrounds humidity sensor 255. PCB 240 and tube 230 are constructed in such a manner that a seal is formed between tube 230 and PCB 240 when tube 230 is fitted onto and over humidity sensor 255. A second end of tube has a diameter that is larger than hole 120; therefore the second end surround hole 120.

Waterproof layer 220 fits above tube 230 between the second end of tube 230 and hole 120. Waterproof layer 220 includes a waterproof, breathable material. Therefore, waterproof layer 220 allows water vapor that enters hole 120 to pass through waterproof layer 220, but prevents water (or a concrete mixture) from passing through. Waterproof layer 220 may be formed from a waterproof, breathable fabric membrane such as Gore-Tex or other similar material. Upper portion 206 fits onto lower portion 208, creating a protective seal.

Figure 3:
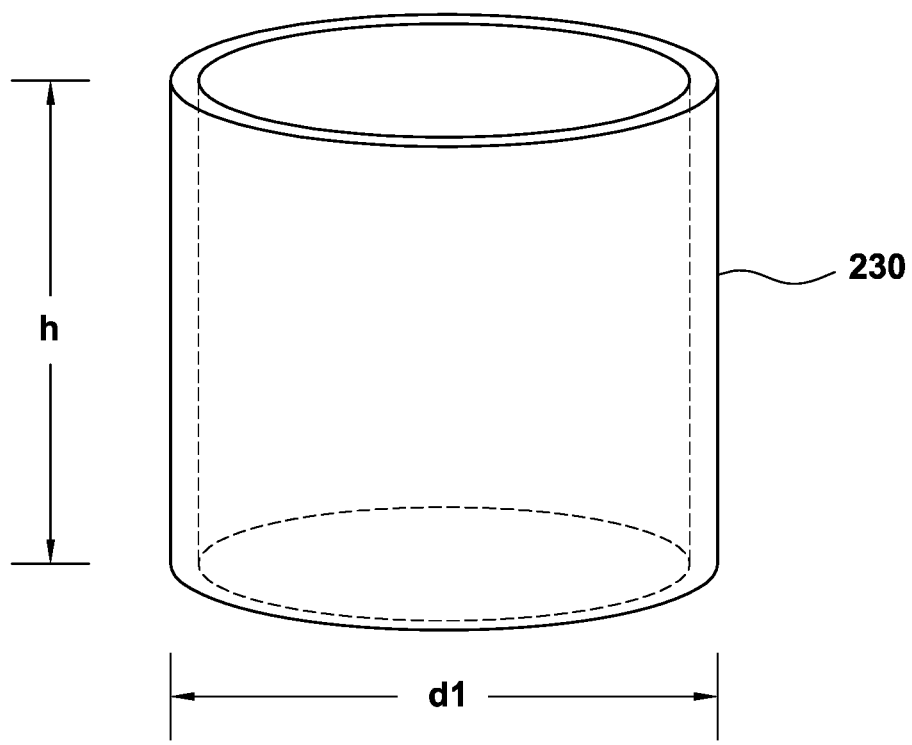
FIG. 3 shows a protective tube in accordance with an embodiment.

FIG. 3 shows protective tube 230 in accordance with an embodiment. Tube 230 may be formed of a waterproof material such as a plastic, rubber, or other material. Tube 230 has a diameter d1 that is determined by the size of humidity sensor 255. Tube 230 surrounds humidity sensor 255; therefore the diameter d1 of tube 230 is greater than the greatest dimension of humidity sensor 255. In one embodiment, diameter d1 of tube 230 is between 0.25 cm and 1.0 cm. Other diameters may be used.

Figure 4:
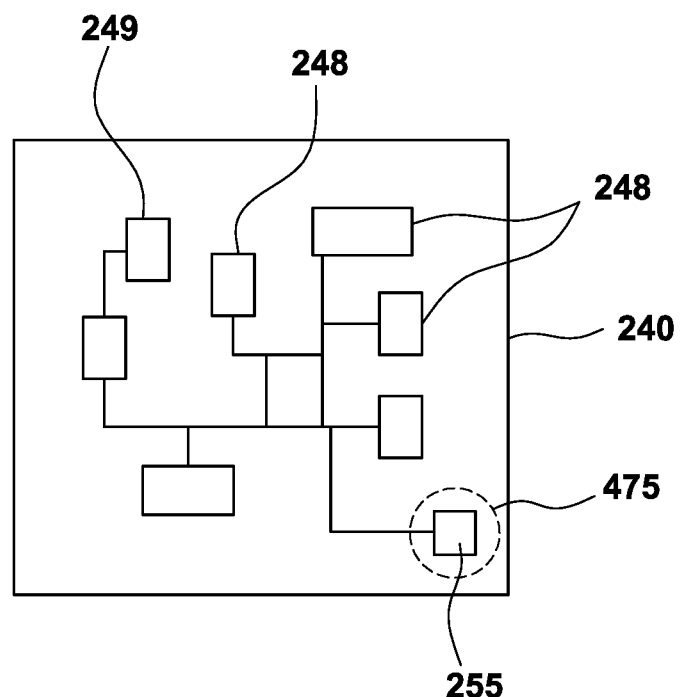
FIG. 4 shows a printed circuit board in accordance with an embodiment.

FIG. 4 shows PCB 240 in accordance with an embodiment. PCB 240 includes a groove 475 surrounding humidity sensor 255. Groove 475 is adapted to receive and support and end of tube 230.

Figure 5:
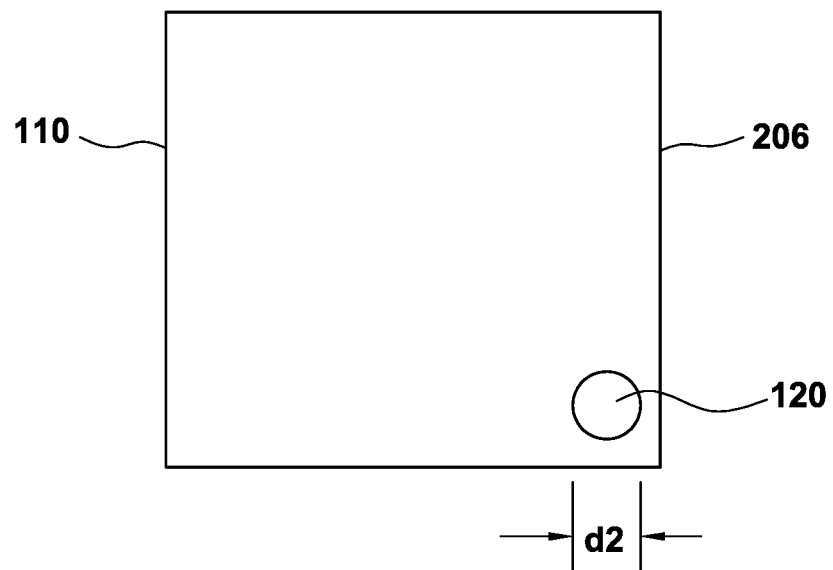
FIG. 5 shows a top view of an upper portion of a sensor in accordance with an embodiment.

FIG. 5 shows a top view of upper portion 206 in accordance with an embodiment. Hole 120 has a diameter d2. Diameter d2 is preferably equal to or smaller than diameter d1 of tube 230. However, any diameter may be used.

Figure 6:
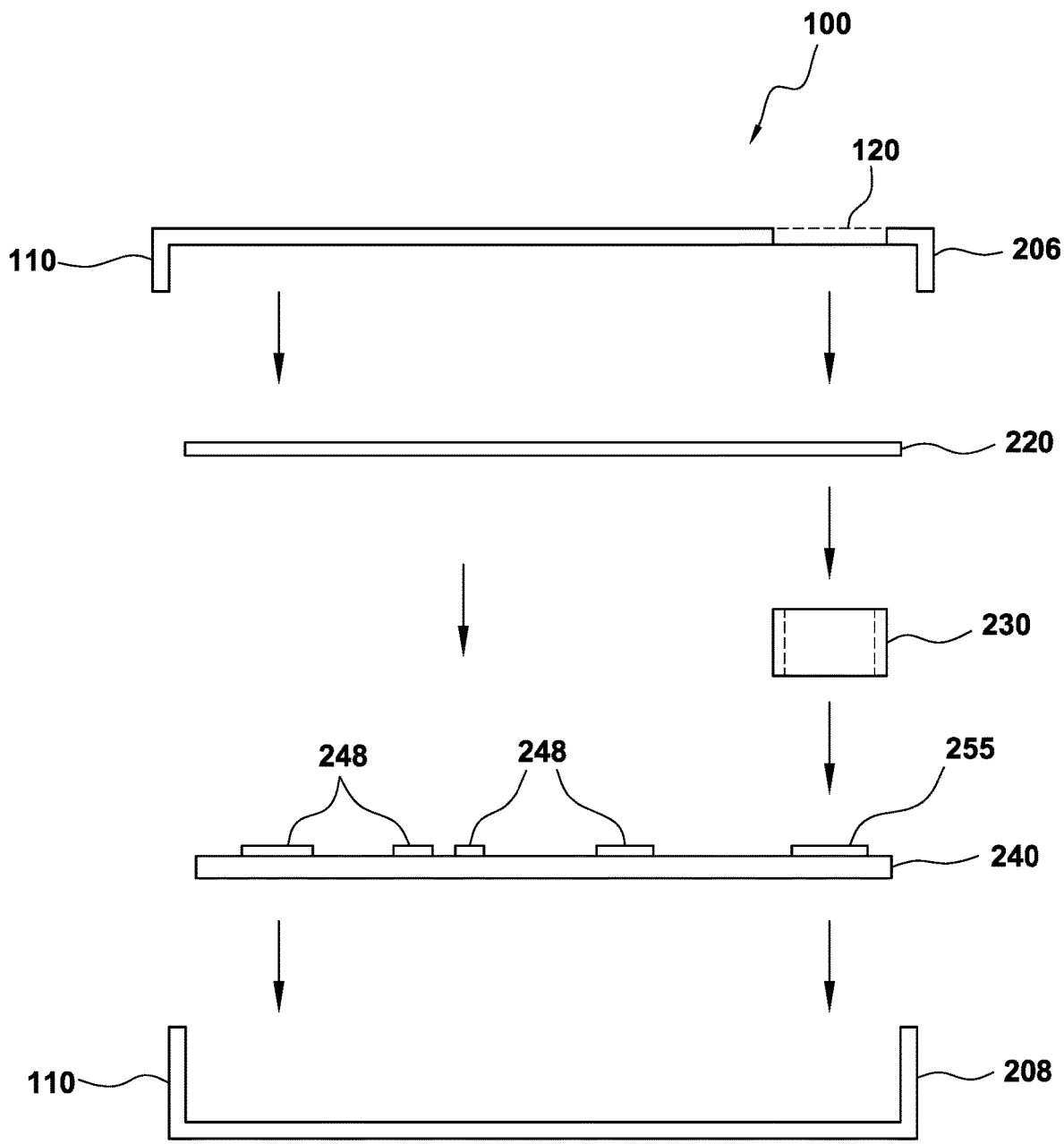
FIGS. 6-7 show cross-sectional views of components of a sensor in accordance with an embodiment.
Figure 7:
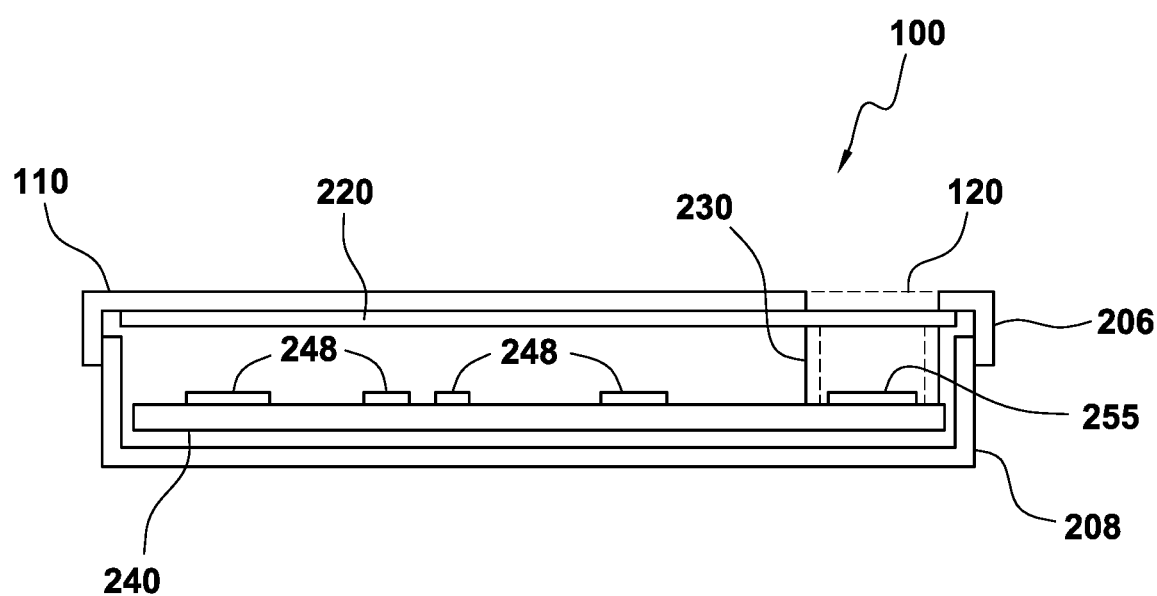

FIGS. 6 and 7 show cross-sectional views of components of sensor 100 in accordance with an embodiment. PCB 240 fits into bottom portion 208. Tube 230 fits onto and over humidity sensor 255. PCB 240 and tube 230 are constructed in such a manner that a first seal is formed between tube 230 and PCB 240 when tube 230 is fitted onto and over humidity sensor 255. Waterproof layer 220 fits above tube 230. Upper portion 206 fits onto lower portion 208, creating a protective seal between upper portion 206 and lower portion 208. As upper portion 206 is closed, a seal also forms between tube 230 and waterproof layer 220. FIG. 7 shows a cross sectional view of components of sensor 100 after upper portion 206 has been fitted onto lower portion 208.

Advantageously, as upper portion 206 is closed over lower portion 208, a first seal is formed between tube 230 and PCB 240, a second seal is formed between tube 230 and waterproof layer 220, and a third seal is formed between waterproof layer 220 and upper portion 206. After these seals are formed, tube 230 defines a volume between hole 120 and humidity sensor 255 that is partially exposed to the surrounding environment. Hole 120 allows water vapor to enter the interior of sensor 100 and reach humidity sensor 255, enabling humidity sensor 255 to measure the humidity of the surrounding environment. Waterproof layer 220 is breathable and allows water vapor to pass through to humidity sensor 255; however, waterproof layer 220 prevents any water (or concrete mixture) from passing through to the interior of sensor 100. In addition, tube 230 advantageously prevents any water vapor that enters through hole 120 from reaching other components of sensor 100. For example, tube 230 protects components 248 (and transceiver 249) from the humidity of the surrounding environment.

In accordance with an embodiment, sensor 100 may be used to obtain measurements of humidity of a concrete mixture. In one embodiment, sensor 100 may be placed on top of the surface of a concrete mixture, with hole 120 facing down (into the concrete mixture). In another embodiment, sensor 100 may be embedded within a concrete mixture. For example, sensor 100 may be embedded several inches or several feet beneath the surface of a concrete mixture.

Figure 8:
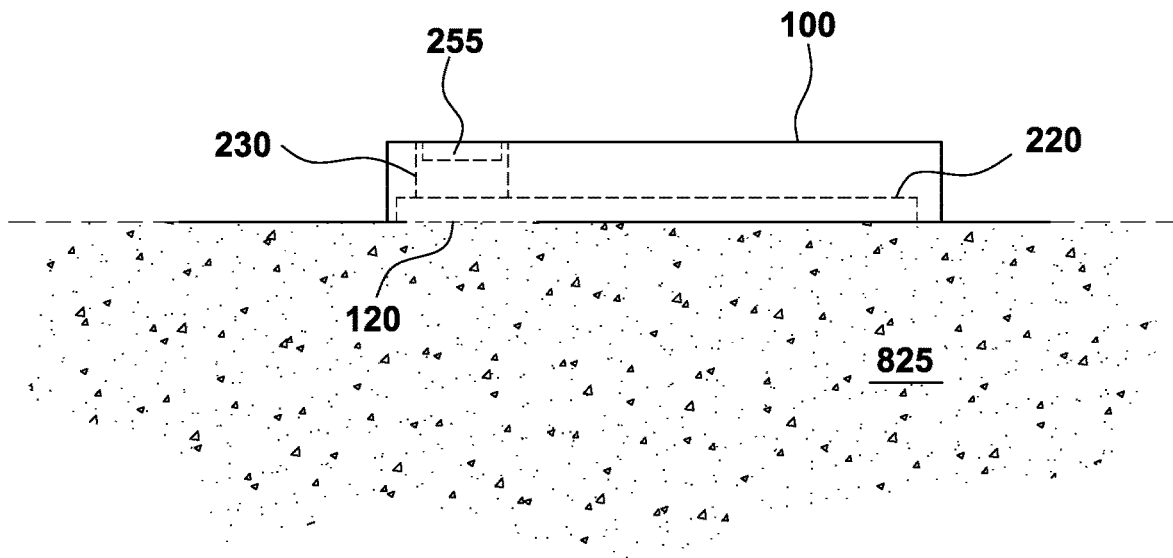
FIG. 8 shows a sensor disposed on a surface of a concrete mixture in accordance with an embodiment.

FIG. 8 shows sensor 100 disposed on a surface of a concrete mixture 825 in accordance with an embodiment. Hole 120 faces downward, proximate the surface of concrete 825. Because hole 120 faces downward, water vapor from concrete mixture 825 readily passes through hole 120, and through layer 220, and reaches humidity sensor 255. Humidity sensor 255 may obtain humidity measurements of the humidity of concrete mixture 825. Sensor 100 may transmit the humidity measurements to a second device via wireless transmission, for example.

Figure 9:
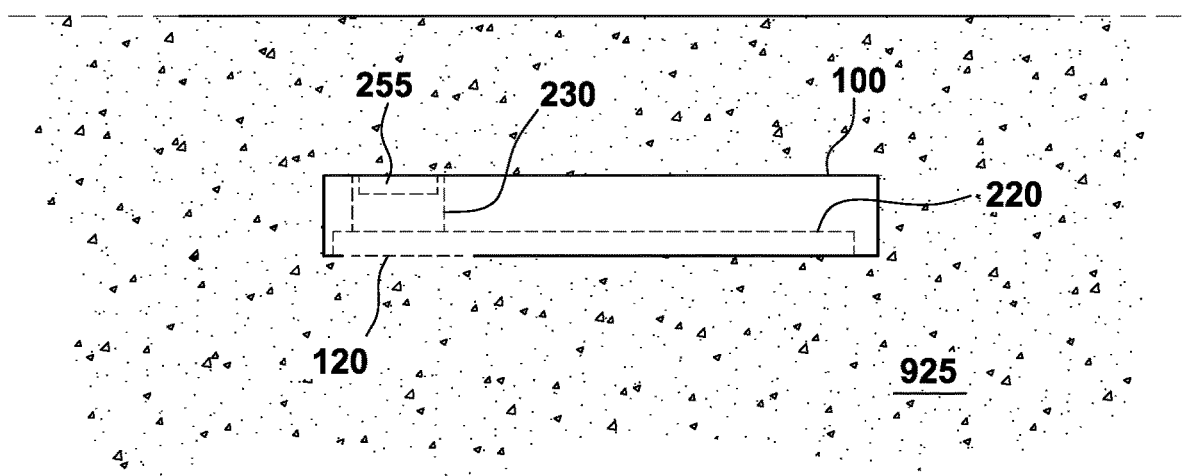
FIG. 9 shows a sensor embedded beneath the surface of a concrete mixture in accordance with an embodiment.

FIG. 9 shows sensor 100 embedded beneath the surface of a concrete mixture 925 in accordance with an embodiment. Hole 120 faces downward. Water vapor from concrete mixture 925 readily passes through hole 120, and through layer 220, and reaches humidity sensor 255. Humidity sensor 255 may obtain humidity measurements of the humidity of concrete mixture 925. Sensor 100 may transmit the humidity measurements to a second device via wireless transmission, for example. In the illustrative embodiment, sensor 100 may transmit data wirelessly through a layer of concrete.

Figure 10:
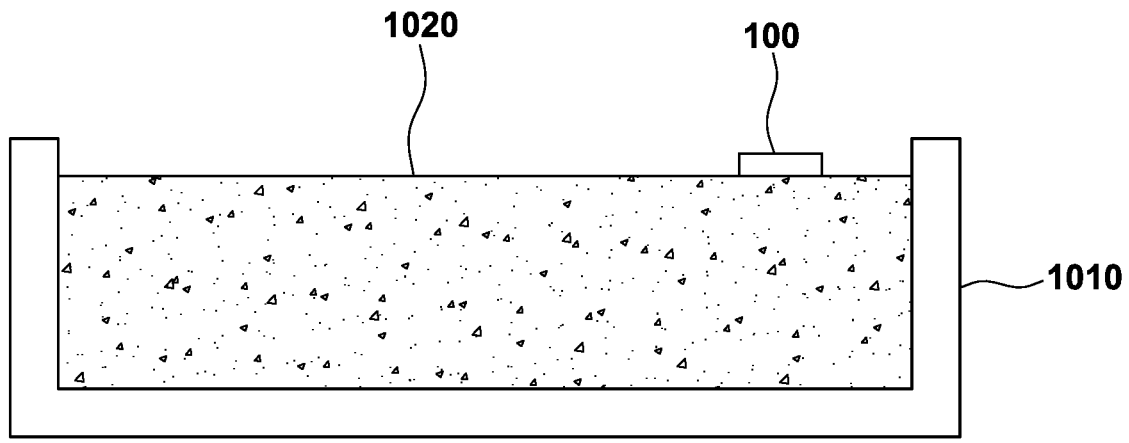
FIG. 10 shows a concrete mixture in a form in accordance with an embodiment.

Sensor 100 may be used in this manner at a construction site, for example. FIG. 10 shows a concrete mixture 1020 in a form 1010 in accordance with an embodiment. Sensor 100 is disposed on the surface of the concrete. Sensor 100 may obtain measurements of the humidity of concrete mixture 1020. Sensor 100 may transmit the humidity measurements to a second device via wireless transmission.

Figure 11:
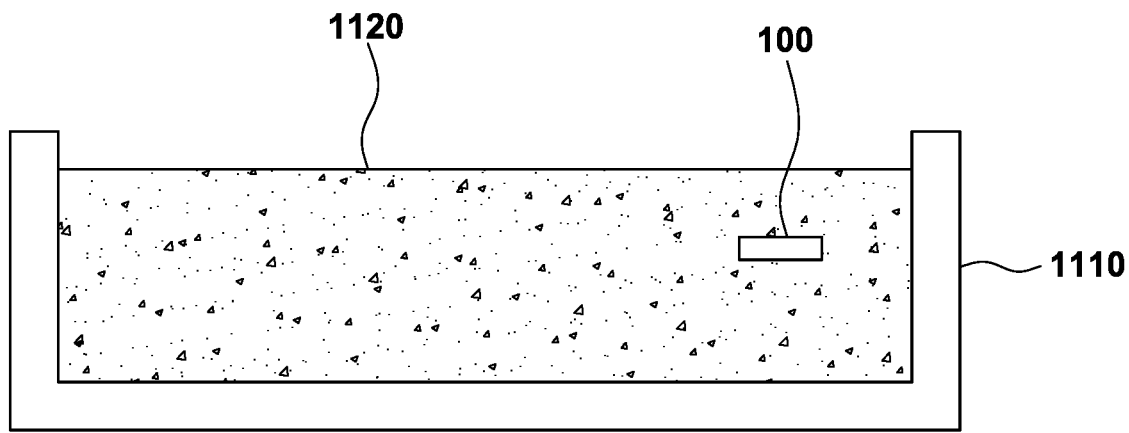
FIG. 11 shows a concrete mixture in a form in accordance with another embodiment.

FIG. 11 shows a concrete mixture 1120 in a form 1110 in accordance with another embodiment. Sensor 100 is embedded under the surface of the concrete. Sensor 100 may obtain measurements of the humidity of concrete mixture 1120. Sensor 100 may transmit the humidity measurements to a second device via wireless transmission.

Figure 12:
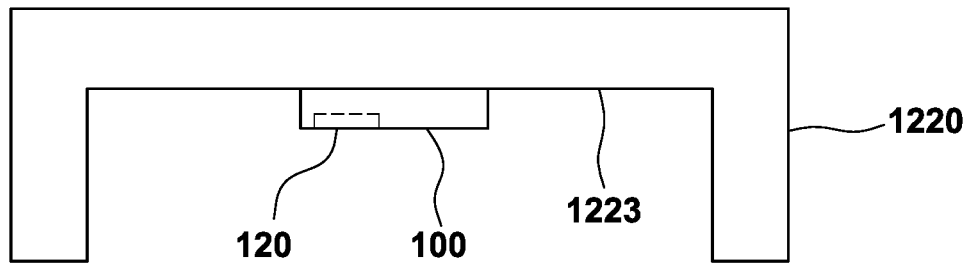
FIG. 12 shows a test cylinder and a cap in accordance with an embodiment.
Figure 12:
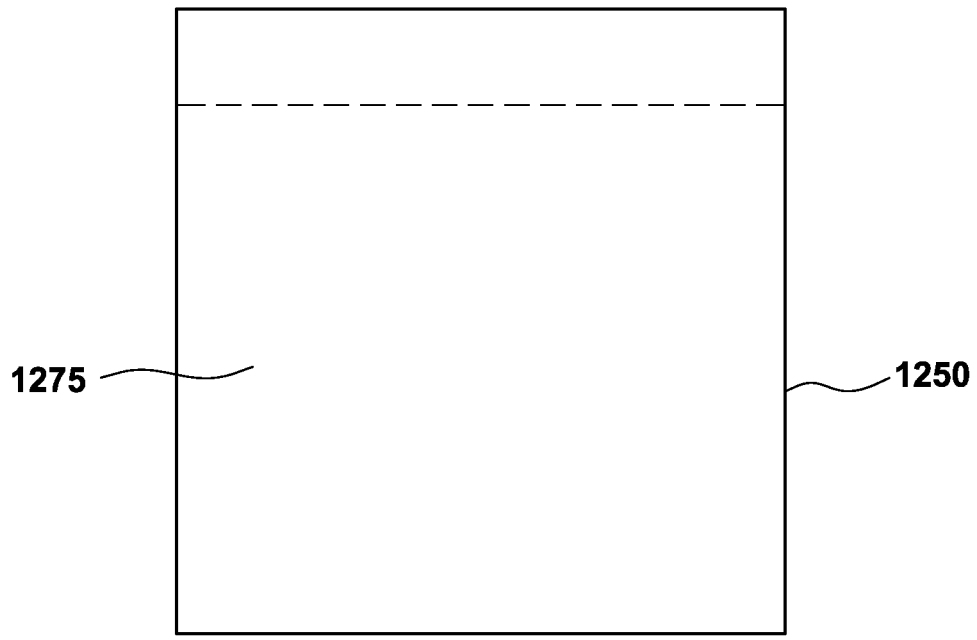

In another embodiment, a sensor may be attached to a cap and placed on a standard test cylinder used to test specimens of concrete. FIG. 12 shows a test cylinder and a cap in accordance with an embodiment. Test cylinder 1250 may be a 4×8-inch or 6×12-inch test cylinder, for example. Test cylinder 1250 contains a specimen of concrete 1275. A cap 1220 is constructed to fit onto test cylinder 1250. Sensor 100 is attached to an interior surface 1223 of cap 1220. Sensor 100 is oriented so that hole 120 faces downward.

Figure 13:
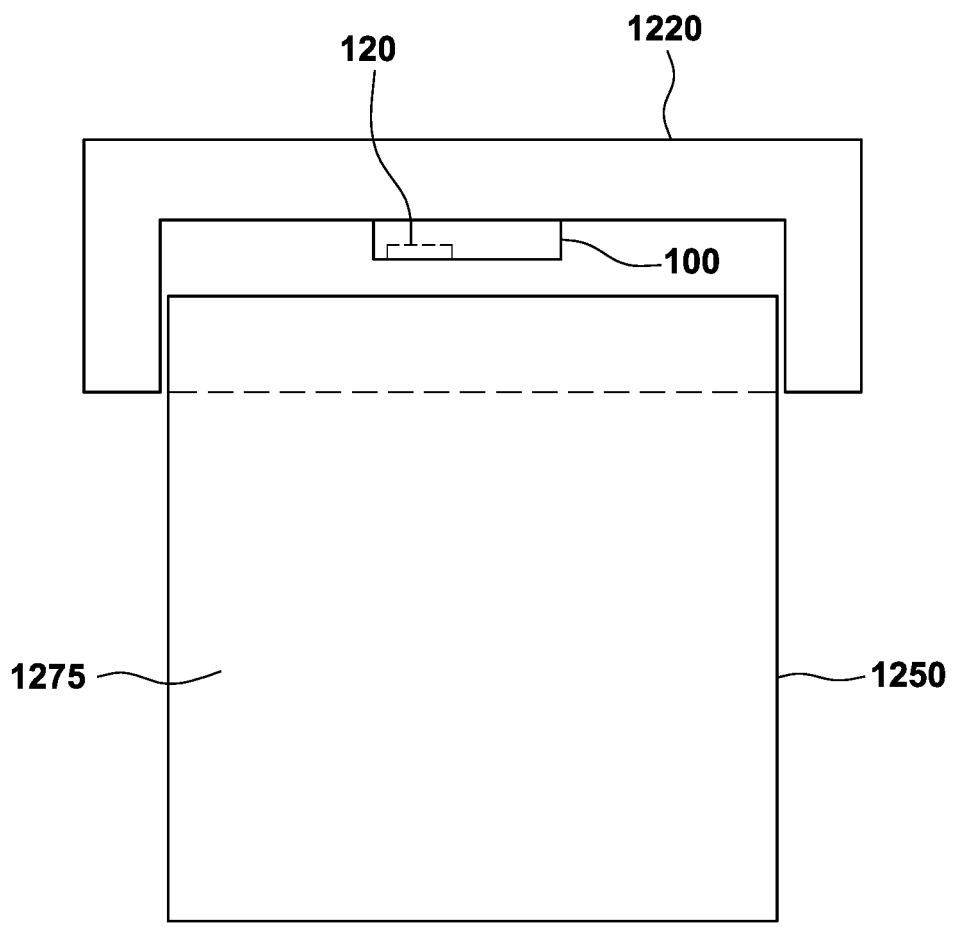
FIG. 13 shows a test cylinder and a cap placed on the test cylinder in accordance with an embodiment.

Cap 1220 may be placed onto test cylinder 1250, as shown in FIG. 13. Cap 1220 may form a seal when placed onto test cylinder 1250. After cap 1220 has been placed onto test cylinder 1250, sensor 100 may obtain measurements of humidity. Because hole 120 faces downward, humidity generated by concrete 1275 may enter sensor 100 through hole 120. A sensor attached to a cap such as cap 1220 may be used in a similar manner to obtain measurements of other characteristics of a concrete mixture contained in a test cylinder, such as temperature, motion, etc.

Devices, systems, apparatus and methods for using a sensor device attached to a cap placed on a concrete test cylinder to obtain measurements of one or more characteristics of a concrete mixture contained in the test cylinder are described, for example, in U.S. patent application Ser. No. 15/414,401, filed Jan. 24, 2017 and entitled "SYSTEMS, APPARATUS AND METHODS FOR OBTAINING MEASUREMENTS CONCERNING THE STRENGTH AND PERFORMANCE OF CONCRETE MIXTURES," which is hereby incorporated by reference herein in its entirety and for all purposes.

Figure 14:
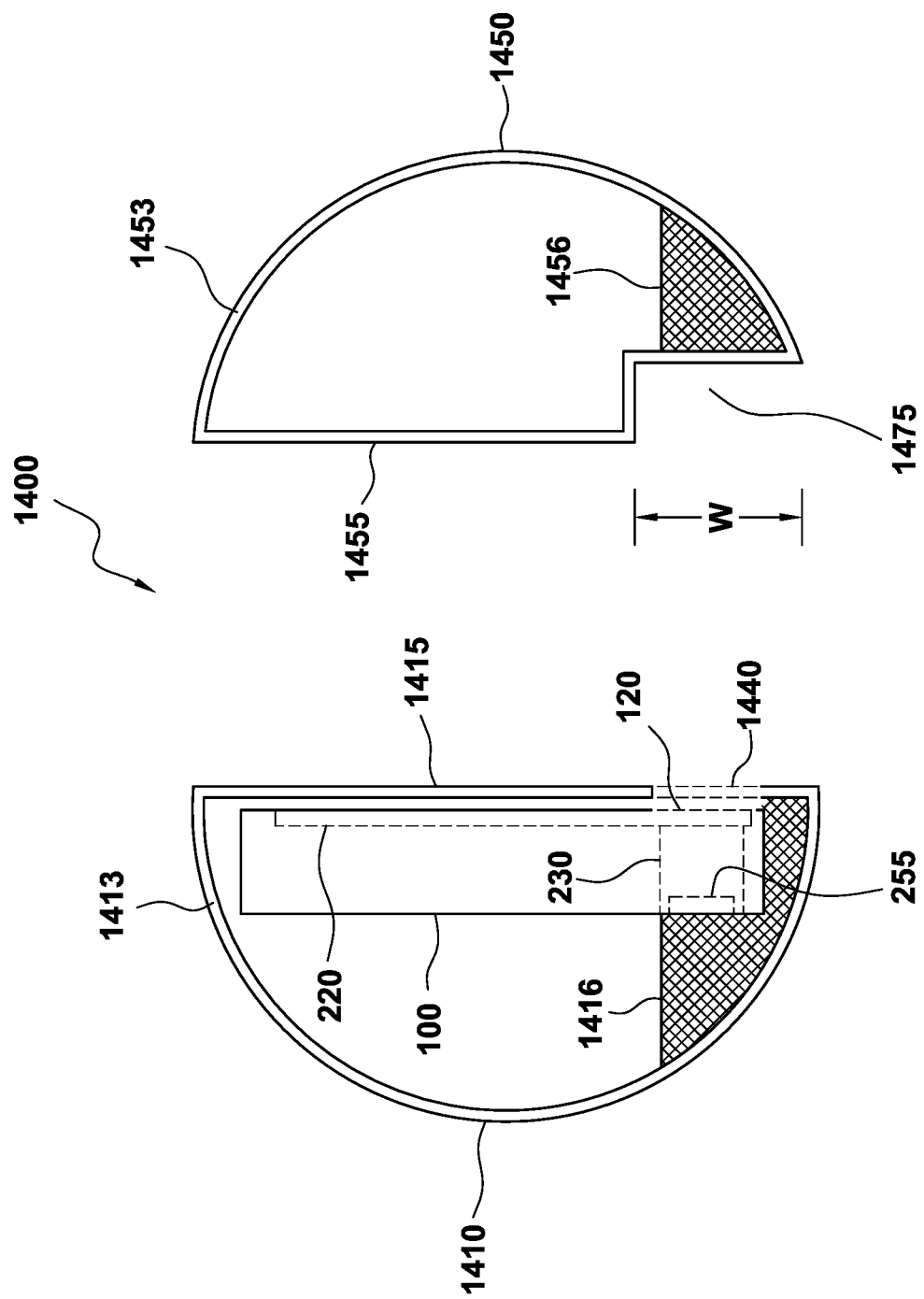
FIG. 14 shows a cross-sectional view of components of a sensing device in accordance with an embodiment.

In other embodiments, sensor 100 may be placed within a sensing device. FIG. 14 shows a cross-sectional view of components of a sensing device in accordance with an embodiment. Sensing device 1400 includes a first portion 1410 and a second portion 1420. First portion 1410 has a hemispherical shaped side 1413 and a flat side 1415. Flat side 1415 has a hole 1440 that is approximately the same size as hole 120 of sensor 100. Sensor 100 is disposed within first portion 1410, proximate the flat side 1415, such that hole 120 of sensor 100 is proximate hole 1440. A predetermined quantity of a substance such as lead is disposed inside of first portion 1410, on the side near hole 120 and hole 1440.

Second portion 1450 has a hemispherical shaped side 1453 and a flat side 1455. Flat side 1455 has a notch 1475 on one side. A width W of notch 1475 is greater than the width of hole 1440. A predetermined quantity of a substance such as lead is disposed inside of second portion 1450, on the side near notch 1475.

Figure 15:
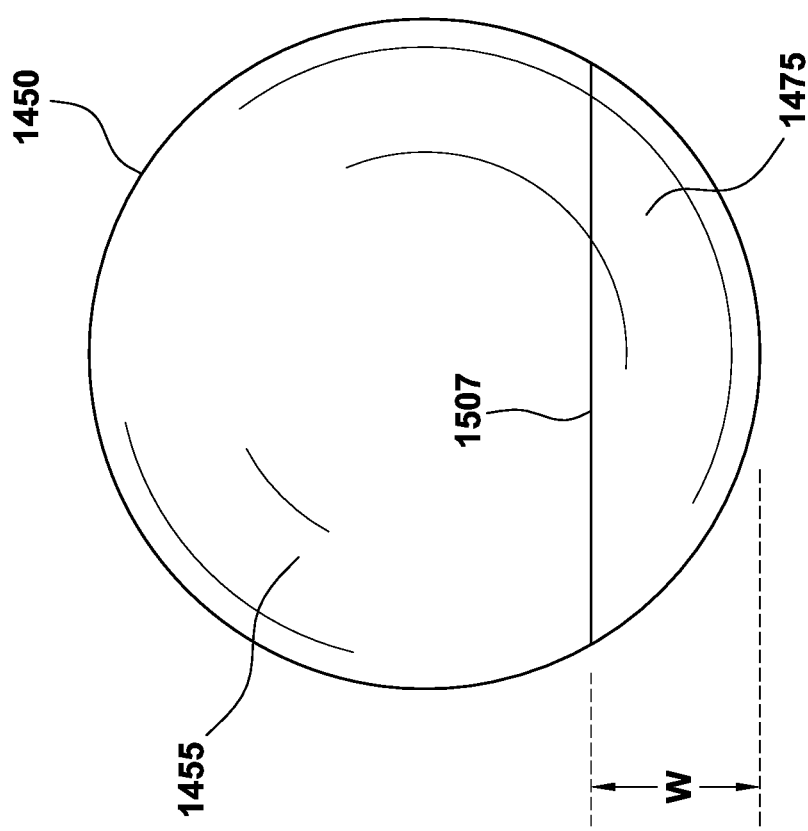
FIG. 15 shows a view of a flat side of a portion of the sensing device of the embodiment of FIG. 14.

FIG. 15 shows a view of flat side 1455 of second portion 1450 of sensing device 1400 in accordance with the embodiment of FIG. 14. Notch 1475 runs longitudinally across flat side 1455, defining a chord 1507.

First portion 1410 and second portion 1450 may be joined to form sensing device 1400. Specifically, flat side 1415 of first portion 1410 is attached to flat side 1455 of second portion 1450.

Figure 16:
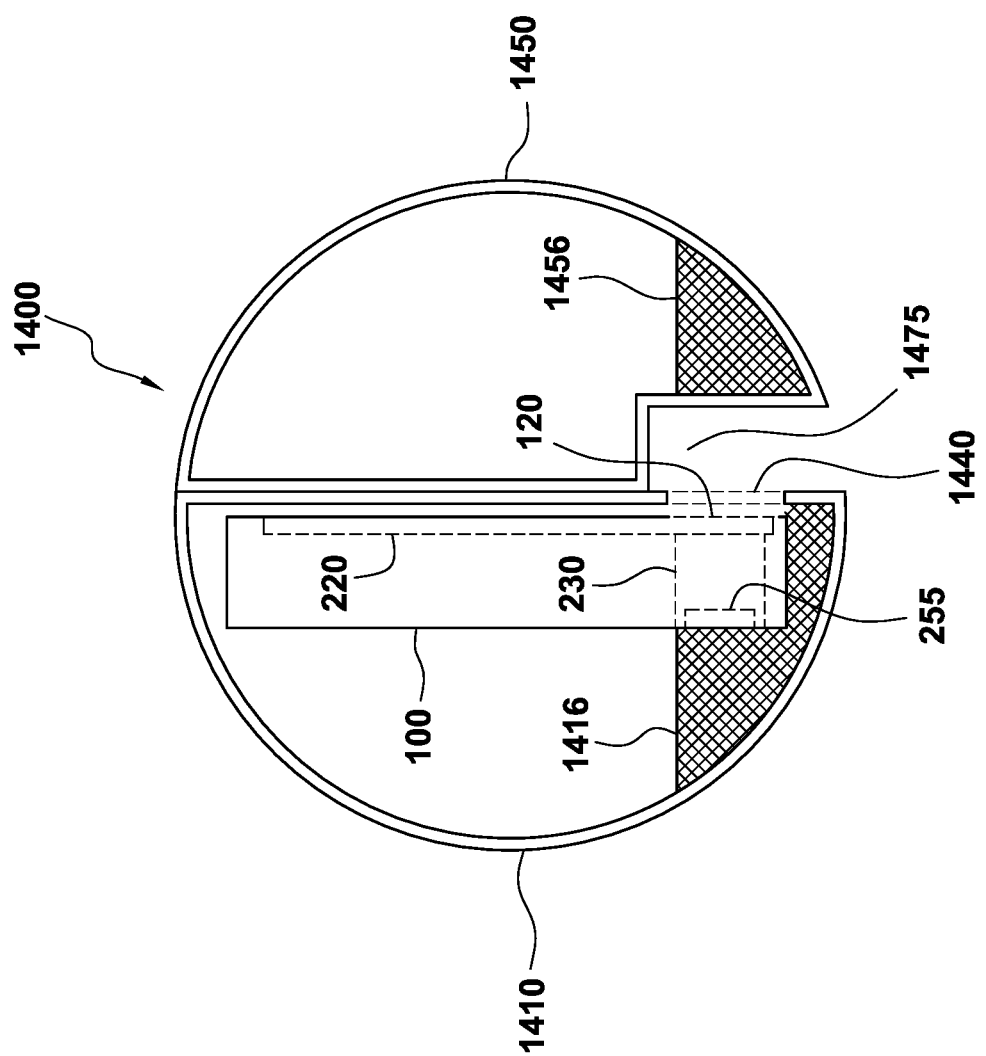
FIG. 16 shows a cross-sectional view of a sensing device in accordance with an embodiment.

FIG. 16 shows a cross-sectional view of sensing device 1400 in accordance with an embodiment. Sensing device 1400 has a spherical, or approximately spherical, shape. Notch 1475 ensure that hole 1440 is exposed to the surrounding environment.

In accordance with an embodiment, sensing device 1400 may be inserted, or partially inserted, into a concrete mixture. While in the concrete mixture, sensor 100 within sensing device 1400 may obtain measurements of the humidity of the concrete mixture.

Figure 17:
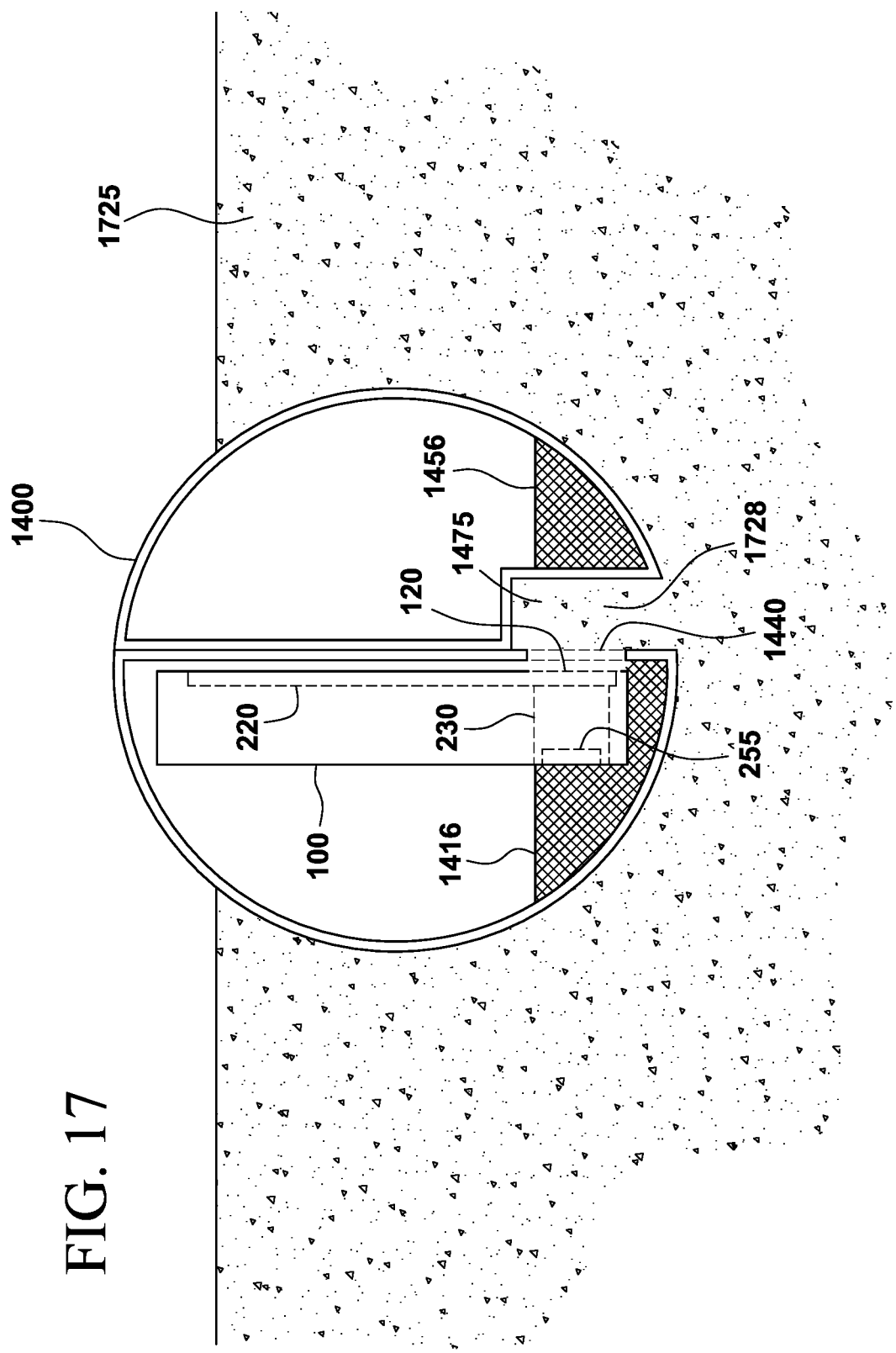
FIG. 17 shows a sensing device embedded in a concrete mixture in accordance with an embodiment.

FIG. 17 shows sensing device 1400 embedded in a concrete mixture 1725 in accordance with an embodiment. For example, sensing device 1400 may be inserted into a concrete mixture within a form at a construction site. The weight of material 1416 and material 1456 cause sensing device to orient itself with the notch 1475 on the underside of the device. Therefore, notch 1475 is embedded within the concrete mixture. A portion 1728 of the concrete enters notch 1475. Humidity from the concrete within notch 1475 enters hole 1440 of sensing device 1400, and enters hole 120 of sensor 100. Humidity sensor 255 may therefore measure the humidity of concrete 1725. Sensor 100 may transmit the humidity measurements via wireless transmission to a remote device.

Figure 18:
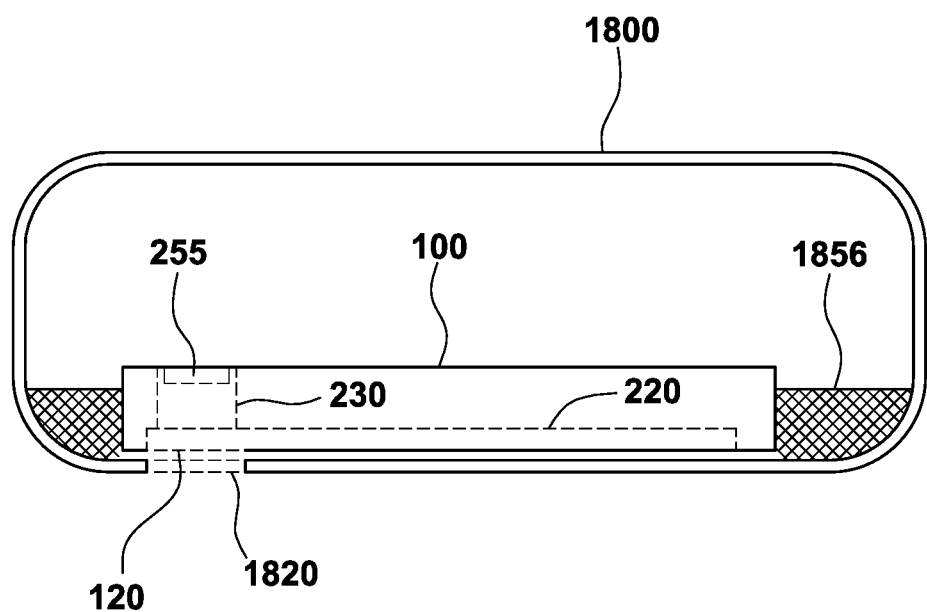
FIG. 18 shows a sensing device in accordance with another embodiment.

In another embodiment, sensor 100 may be disposed within a sensing device having a different shape, such as a rectangular prism, a triangular prism, a cube, a disc, etc. FIG. 18 shows a sensing device 1800 in accordance with another embodiment. Sensing device 1800 has a cuboid shape (a rectangular prism with rounded edges). A hole 1820 is disposed on one side of sensing device 1800. Hole 120 of sensor 100 is disposed proximate to hole 1820 of sensing device 1800. In this manner, humidity of the surrounding environment may enter through hole 1820 and hole 120 and reach humidity sensor 255.

In accordance with an embodiment, data obtained by sensor 100 may be transmitted via a network to a processor. The processor analyzes the data and generates a prediction relating to a characteristic of a concrete mixture based on the data. For example, humidity measurements obtained by sensor 100 may be used to generate a prediction of strength or maturity of a concrete mixture. Data from multiple sensors may be received and used to generate multiple predictions.

Figure 19:
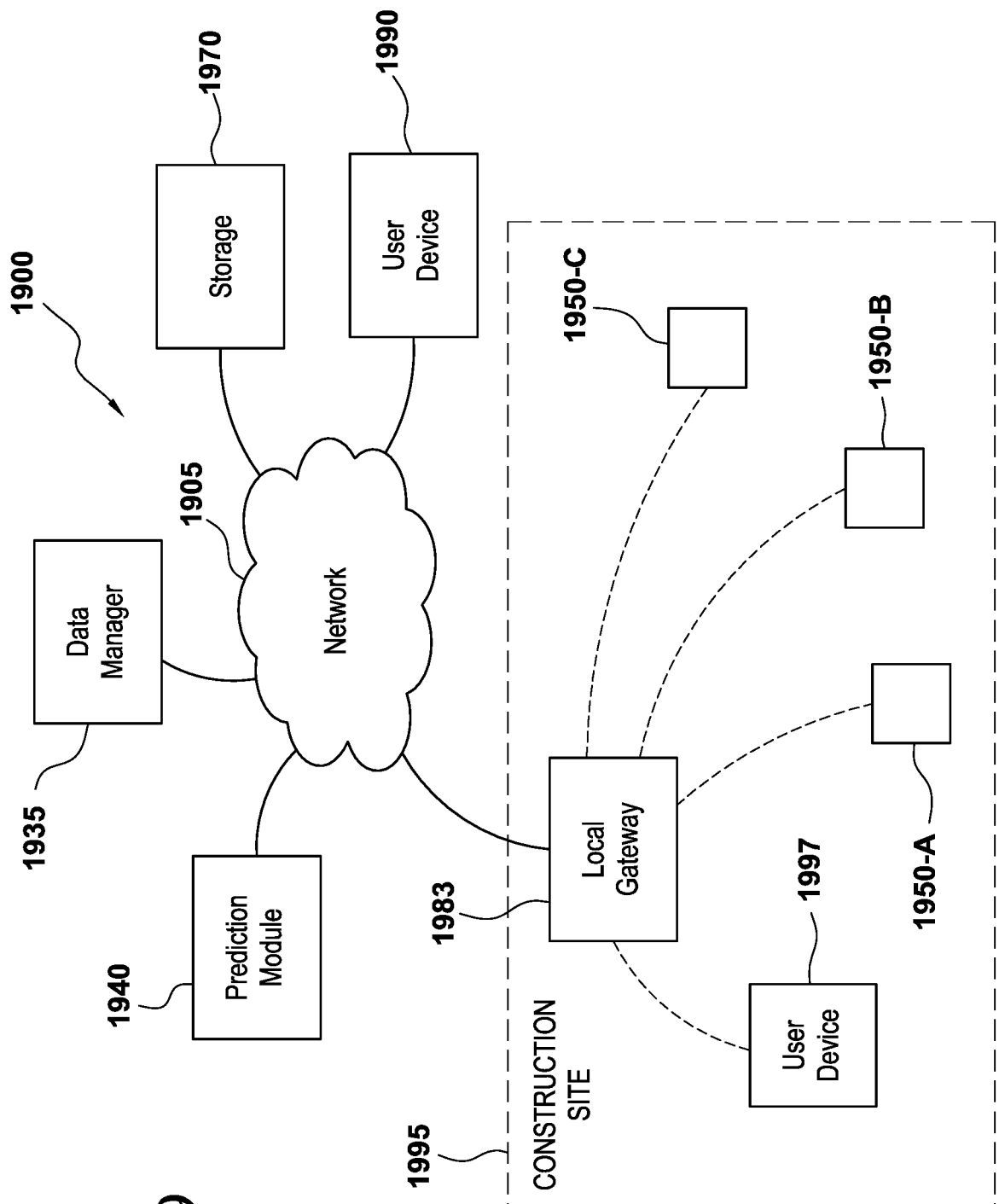
FIG. 19 shows a communication system in accordance with an embodiment.

FIG. 19 shows a communication system in accordance with an embodiment. Communication system 1900 includes a network 1905, which may include the Internet, for example, a data manager 1935, a prediction manager 1940, and a storage 1970. Communication system 1900 also includes a user device 1990, which may be a personal computer, a laptop device, a cell phone, a tablet device, etc.

Communication system 1900 also includes a local gateway 1983, which is connected to network 1905. Local gateway 1983 may include a wireless modem, for example. Local gateway 1983 is located at a construction site 1995, and is linked to a plurality of sensing devices 1950-A, 1950-B, 1950-C, etc., which are disposed at various locations at the construction site. Each sensing device 1950 includes a sensor similar to sensor 100. Each sensing device 1950 may be similar to sensing device 1400 described herein, for example.

Sensing devices 1950 are disposed at various sites at a construction site. For example, a sensing device 1950-A may be embedded in a first concrete form, sensing device 1950-B may be embedded in a second concrete form, etc. Using methods and apparatus similar to those described above, each sensing device 1950 obtains humidity measurements related to a respective concrete mixture. Each sensing device 1950 transmits measurement data to data manager 1935 via local gateway 1983 and network 1905. For example, each sensing device 1950 may transmit measurement data wirelessly to local gateway 1983, which transmits the measurement data to data manager 1935 via network 1905. Each sensing device 1950 may also transmit an identifier uniquely identifying itself. For example, an RFID tag embedded in each sensing device 1950 may transmit identification information. Communication system 1900 may include any number of sensing devices.

In one embodiment, multiple sensing devices 1950 may be located at a single location (e.g., a single construction site). In another embodiment, multiple sensing devices 1950 may be located at multiple locations (e.g., at multiple construction sites).

Communication system 1900 also includes a user device 1997, which may be a personal computer, laptop device, tablet device, cell phone, or other processing device which is located at a construction site and used by a technician at the site. User device 1997 may communicate with network 1905, with local gateway 1983, with a sensing device 1950, and/or with other devices within communication system 1900.

Data manager 1935 receives humidity measurement data from one or more sensing devices 1950 and may analyze the measurement data. In the illustrative embodiment, data manager 1935 transmits the measurement data to prediction manager 1940 (or otherwise makes the data available to prediction manager 1940). Prediction manager 1940 may generate predictions concerning the behavior of one or more concrete specimens. For example, prediction manager 1940 may receive humidity data from sensing device 1950-A and, based on the measurement data, generate predictions regarding the water-to-cementitious ratio, durability, strength, slump, maturity, etc., of the concrete mixture in which sensing device 1950-A is located. In one embodiment, the measurement data received by data manager 1935 is provided to a real-time model to project setting behavior and strength for the entire batch of concrete. In another embodiment, the measurement data is continually subject to statistical analysis to generate real-time projections, control charts, etc. Data manager 1935 may store the measurement data and/or the prediction data in storage 1970. For example, measurements and/or prediction data may be stored in a database. Other data structures may be used to store measurement and/or prediction data.

In one embodiment, data manager 1935 may transmit measurement data and/or prediction information relating to water-to-cementitious ratio, durability, strength, slump, maturity, etc. to a user device such as user device 1990 or user device 1997 to enable a technician to access and view the information. For example, user device 1990 and/or user device 1997 may display measurement data and/or prediction data on a web page, or in another format.

In one embodiment, storage 1970 includes a cloud storage system. Data obtained by a sensing device 1950 may be transmitted to and saved in storage 1970 in real-time. A cloud implementation such as that illustrated by FIG. 19 may allow data from projects in multiple regions or multiple countries to be auto-consolidated in a single database.

Figure 20:
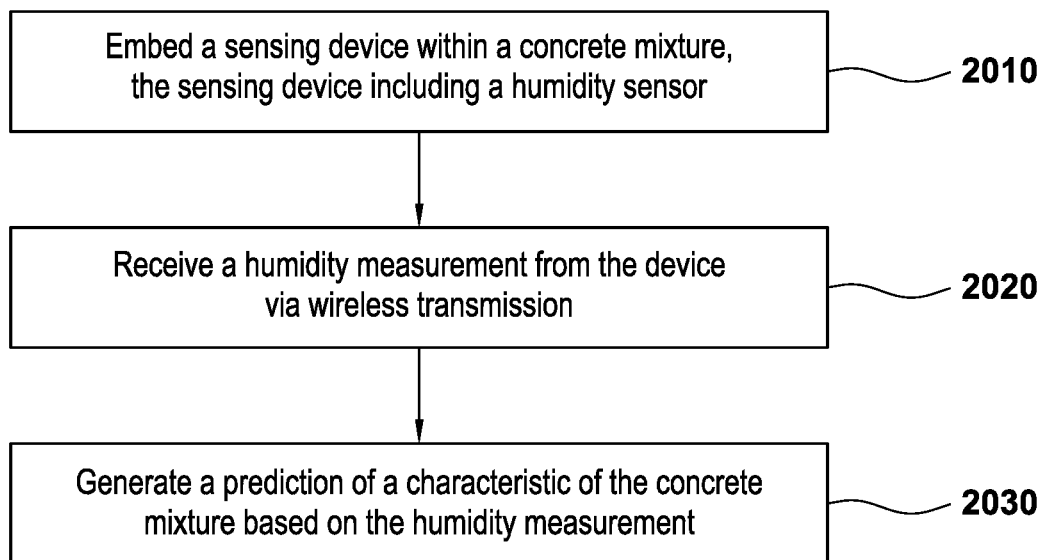
FIG. 20 is a flowchart of a method in accordance with an embodiment.

FIG. 20 is a flowchart of a method in accordance with an embodiment. At step 2010, a sensing device is embedded within a concrete mixture, the sensing device including a humidity sensor. At step 2020, a humidity measurement is received from the device via wireless transmission. At step 2030, a prediction of a characteristic of the concrete mixture is generated based on the humidity measurement.

Figure 21A:
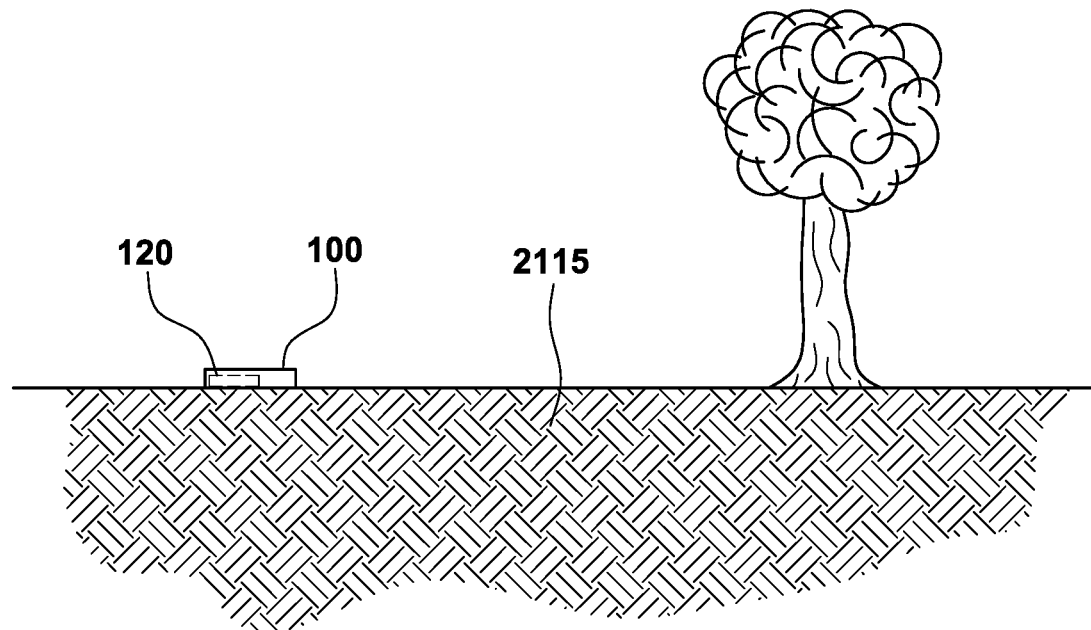
FIG. 21A shows a sensor disposed on the surface of soil in accordance with an embodiment.
Figure 21B:
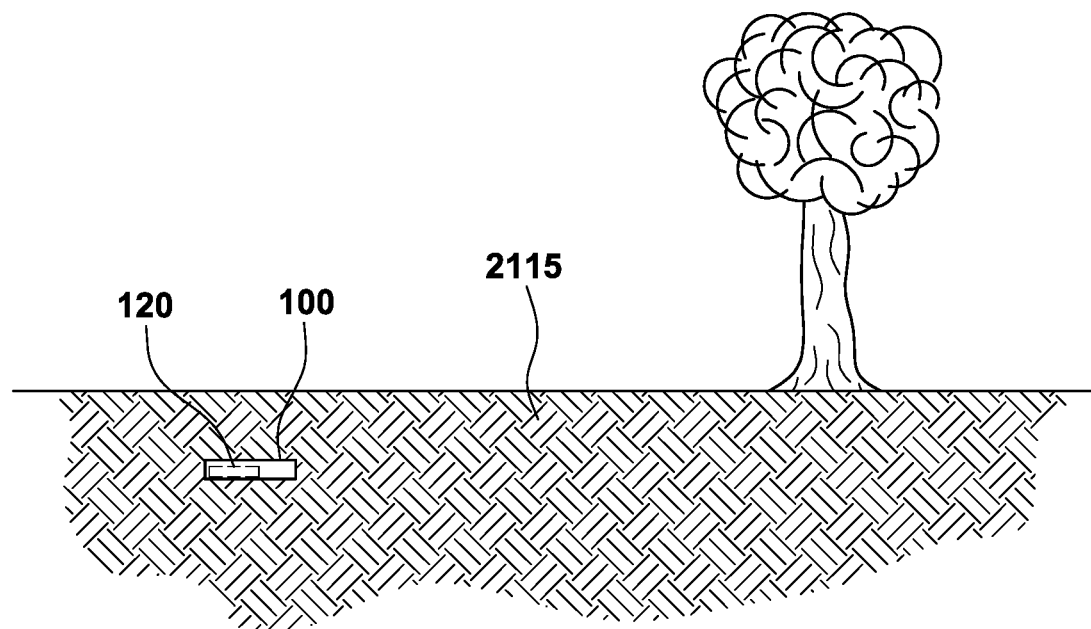
FIG. 21B shows a sensor embedded under the surface of soil in accordance with an embodiment.

While embodiments have been discussed herein in the context of the concrete production and testing and construction industries, systems, methods, and apparatus described herein may be used in other fields and for other uses, as well. For example, a sensor similar to sensor 100 described herein, and/or a sensing device such as sensing device 1400 described herein, may be used in an agricultural setting to determine the humidity of soil. For example, a sensor may be placed on top of the soil, or buried several inches or feet under the soil. FIG. 21A shows sensor 100 disposed on the surface of soil 2115 in accordance with an embodiment. FIG. 21B shows sensor 100 embedded under the surface of soil 2115 in accordance with another embodiment. In the manner described herein, sensor 100 may obtain measurements of the humidity of soil 2115, and transmit the measurement data to a remote device via wireless transmission. A prediction of a characteristic of soil 2115 may then be generated based on the measurement data.

In other embodiments, sensors and sensing devices described herein may be used to analyze other substances including, without limitation, water, water mixtures, chemical products, paint, petroleum-based substances, food products, etc.

In various embodiments, the method steps described herein, including the method steps described in FIG. 20, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 20, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 22:
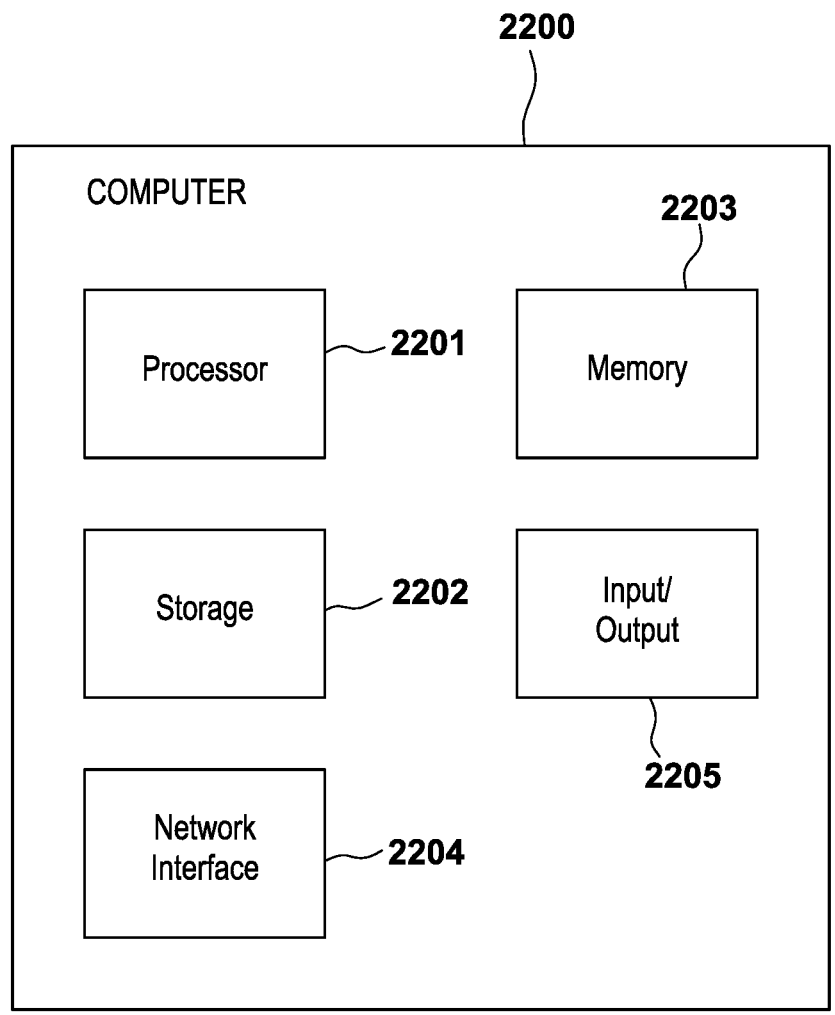
FIG. 22 shows a high-level block diagram of an exemplary computer that may be used to implement certain embodiments.

A high-level block diagram of an exemplary computer that may be used to implement systems, apparatus and methods described herein is illustrated in FIG. 22. Computer 2200 includes a processor 2201 operatively coupled to a data storage device 2202 and a memory 2203. Processor 2201 controls the overall operation of computer 2200 by executing computer program instructions that define such operations. The computer program instructions may be stored in data storage device 2202, or other computer readable medium, and loaded into memory 2203 when execution of the computer program instructions is desired. Thus, the method steps of FIG. 20 can be defined by the computer program instructions stored in memory 2203 and/or data storage device 2202 and controlled by the processor 2201 executing the computer program instructions. For example, the computer program instructions can be implemented as computer executable code programmed by one skilled in the art to perform an algorithm defined by the method steps of FIG. 20. Accordingly, by executing the computer program instructions, the processor 2201 executes an algorithm defined by the method steps of FIG. 20. Computer 2200 also includes one or more network interfaces 2204 for communicating with other devices via a network. Computer 2200 also includes one or more input/output devices 2205 that enable user interaction with computer 2200 (e.g., display, keyboard, mouse, speakers, buttons, etc.).

Processor 2201 may include both general and special purpose microprocessors, and may be the sole processor or one of multiple processors of computer 2200. Processor 2201 may include one or more central processing units (CPUs), for example. Processor 2201, data storage device 2202, and/or memory 2203 may include, be supplemented by, or incorporated in, one or more application-specific integrated circuits (ASICs) and/or one or more field programmable gate arrays (FPGAs).

Data storage device 2202 and memory 2203 each include a tangible non-transitory computer readable storage medium. Data storage device 2202, and memory 2203, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2205 may include peripherals, such as a printer, scanner, display screen, etc. For example, input/output devices 2205 may include a display device such as a cathode ray tube (CRT) or liquid crystal display (LCD) monitor for displaying information to the user, a keyboard, and a pointing device such as a mouse or a trackball by which the user can provide input to computer 2200.

Any or all of the systems and apparatus discussed herein, including sensor 100, sensing device 1400, data manager 1935, prediction module 1940, storage 1970, local gateway 1983, user device 1990, and user device 1997, and components thereof, may be implemented using a computer such as computer 2200.

One skilled in the art will recognize that an implementation of an actual computer or computer system may have other structures and may contain other components as well, and that FIG. 22 is a high level representation of some of the components of such a computer for illustrative purposes.

In accordance with another embodiment, a sensor is embedded in a layer of concrete (e.g., within a concrete floor or other surface). A second layer of a selected material (e.g., rubber) is deposited on top of the concrete layer. The second layer may be deposited on the concrete to function as a protective layer or for another reason. The sensor obtains measurements of one or more characteristics of the concrete and transmits the information. A second device receives the measurement data and may predict a second characteristic of the concrete based on the measurement data.

Figure 23A:
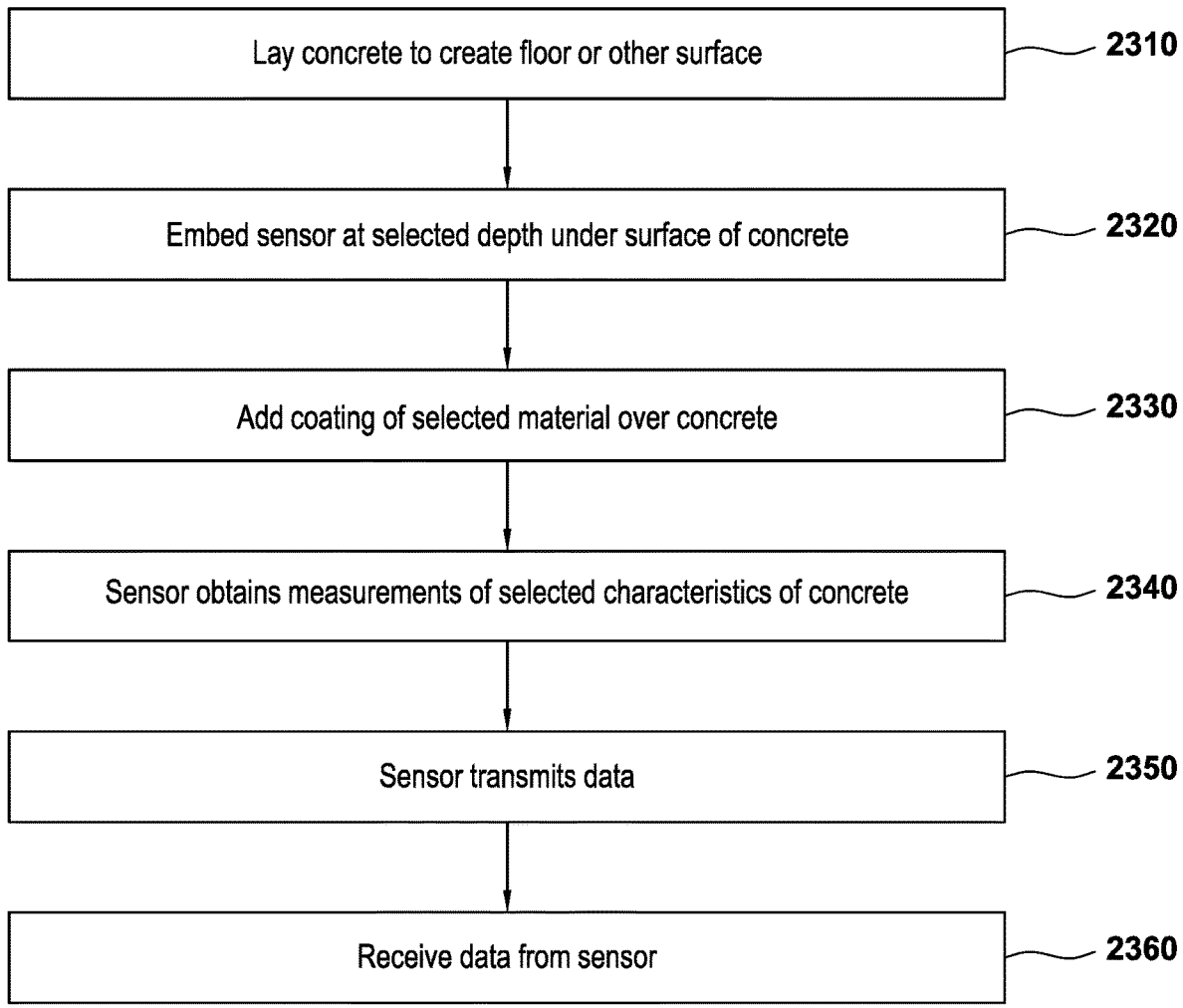
FIG. 23A is a flowchart of a method of obtaining data relating to characteristics of a concrete mixture in accordance with an embodiment.

FIG. 23A is a flowchart of a method of determining one or more characteristics of concrete in accordance with an embodiment. At step 2310, concrete is laid to create a floor or other surface. At step 2320, a sensor is embedded under the surface of the concrete at a selected depth. For example, the sensor may be embedded at a depth of approximately one inch. A sensor may be embedded at other depths. At step 2330, a coating of a selected material is added over the concrete.

Figure 23B:
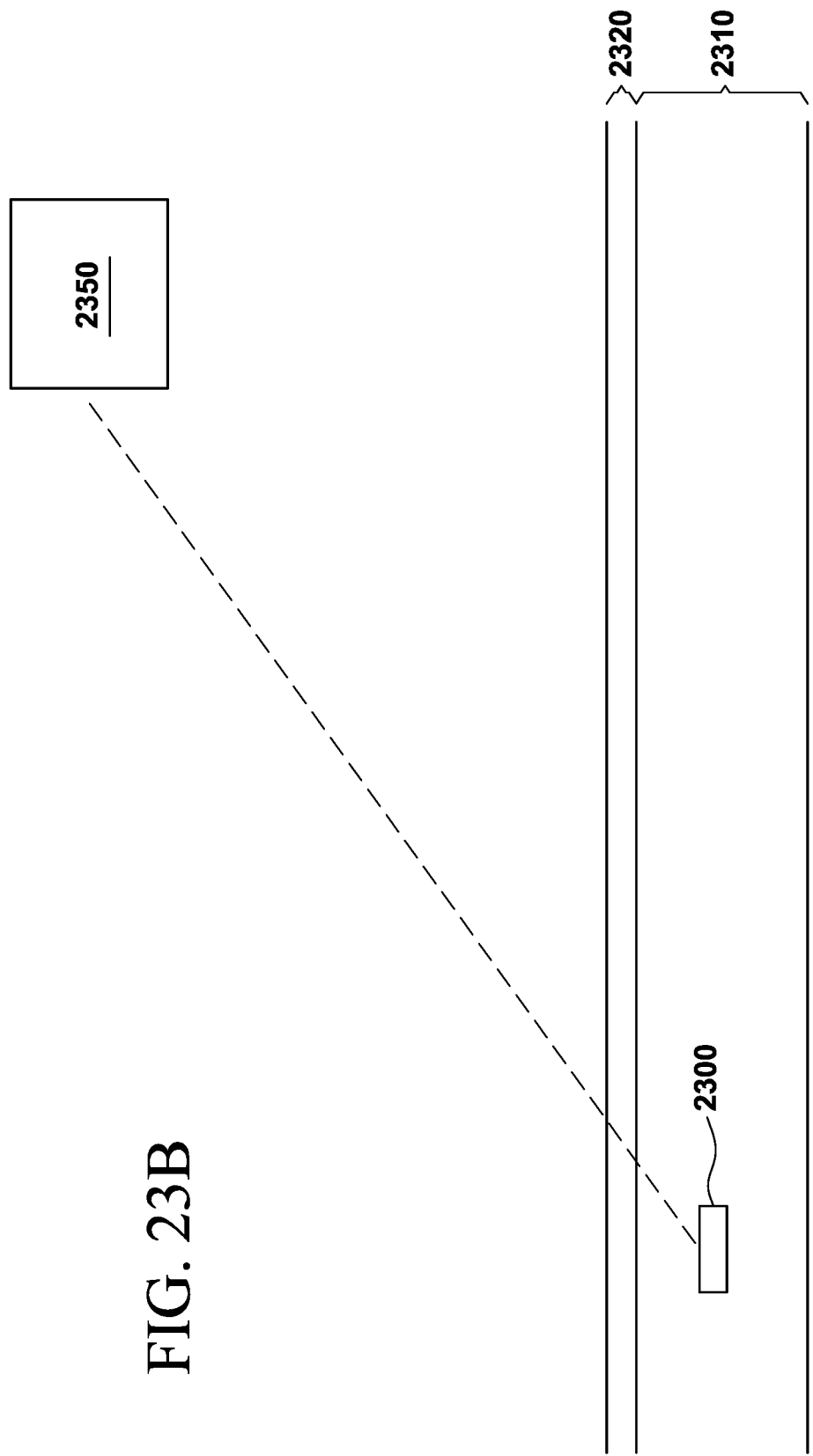
FIG. 23B shows a concrete structure in accordance with an embodiment.

FIG. 23B shows the construction of a concrete floor in accordance with an embodiment. Concrete layer 2310 is laid down. Sensor 2300 is embedded in the concrete. Sensor 2300 may be similar to sensor 100 of FIG. 1 and FIG. 2, for example. A layer 2320 of a selected material is laid down on top of the concrete layer 2310. For example layer 2320 may include rubber or another material.

At step 2340, the sensor obtains measurement data of one or more selected characteristics of the concrete. In the illustrative embodiment, sensor 2300 obtains measurement data pertaining to one or more characteristics of the concrete in layer 2310. For example, sensor 2300 may obtain data pertaining to temperature, humidity, salinity, pH levels, sonic signals, conductivity, etc. At step 2350, the sensor transmits the measurement data. Sensor 2300 transmits the measurement data wirelessly. At step 2360, a second device receives the measurement data from the sensor. In the illustrative embodiment, a second device 2350 receives the measurement data. As discussed elsewhere herein, the measurement data may be used to predict one or more characteristics of the concrete in layer 2310.

The inventors have observed that use of sensor devices, such as sensor 100 of FIG. 1 and FIG. 2, to obtain data relating to a concrete mixture is sometimes complicated by the difficulty of determining when to activate the sensor device (i.e., when to activate the various sensors of the sensor device so that the sensors begin to generate data pertaining to characteristics of the concrete and transmit the measurement data) and the further difficulty of actually activating the sensor device at a desired time. On the one hand, it is undesirable to activate the sensor device before the sensor device has been embedded in the concrete. On the other hand, it is undesirable to activate the sensor device long after the sensor device has been embedded in the concrete. Ideally, the sensor device should be activated at the moment the sensor device is embedded in the concrete mixture.

The inventors have further observed that a sensor device typically experiences a spike in humidity when first embedded in a concrete mixture. The humidity within a concrete mixture is typically significantly higher than the humidity of the outside environment. The inventors have determined that this difference can be utilized to determine when to activate a sensor device.

Thus, in accordance with an embodiment, a sensor device includes a housing and a plurality of sensors disposed in the housing. The plurality of sensors include a humidity sensor and one or more second sensors adapted to obtain measurements of selected characteristics of a concrete mixture, such as temperature, salinity, pH levels, sonic signals, motion, elevation, acceleration, conductivity, etc. For example, the plurality of sensors may include one or more of the following: a temperature sensor, a salinity sensor, a conductivity sensor, a motion sensor, a pH sensor, an acceleration sensor (accelerometer), a sonic sensor, etc. The sensor device may also include a location sensor (e.g., with GPS functionality). The housing includes an opening adapted to permit humidity to enter the housing but prevent liquid (and concrete) from entering the housing. The opening may be a hole in the housing, for example. For example, the dimensions of the hole may be sufficiently small so that the surface tension of water prevents water and concrete from passing through the hole. For example, the hole may have a width of one millimeter or smaller. The humidity sensor within the sensor device is disposed proximate the hole.

Figure 24A:
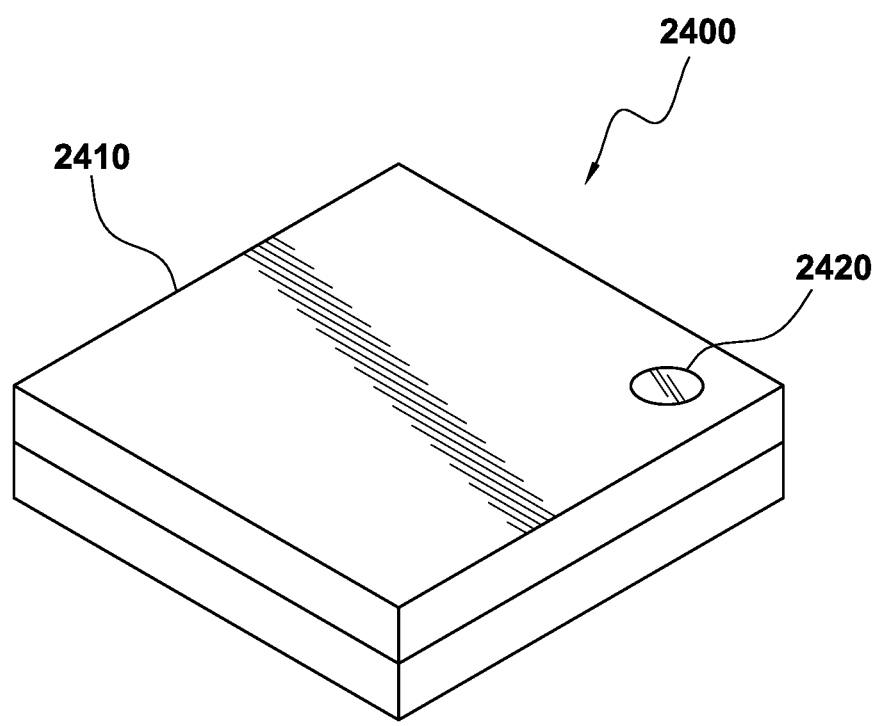
FIG. 24A shows a sensor device in accordance with an embodiment.

FIG. 24A shows a sensor device 2400 in accordance with an embodiment. Sensor device 2400 includes a housing 2410. Housing 2410 includes an opening. In the illustrative embodiment, the opening is a hole 2420. Hole 2420 allows water vapor to pass through; however, the diameter of hole 2420 is sufficiently small so that water and concrete cannot pass through the hole. For example, the hole may have a width of one millimeter or smaller. For example, hole 2420 may have a diameter of between 0.5 millimeters and 1.0 millimeter.

Figure 24B:
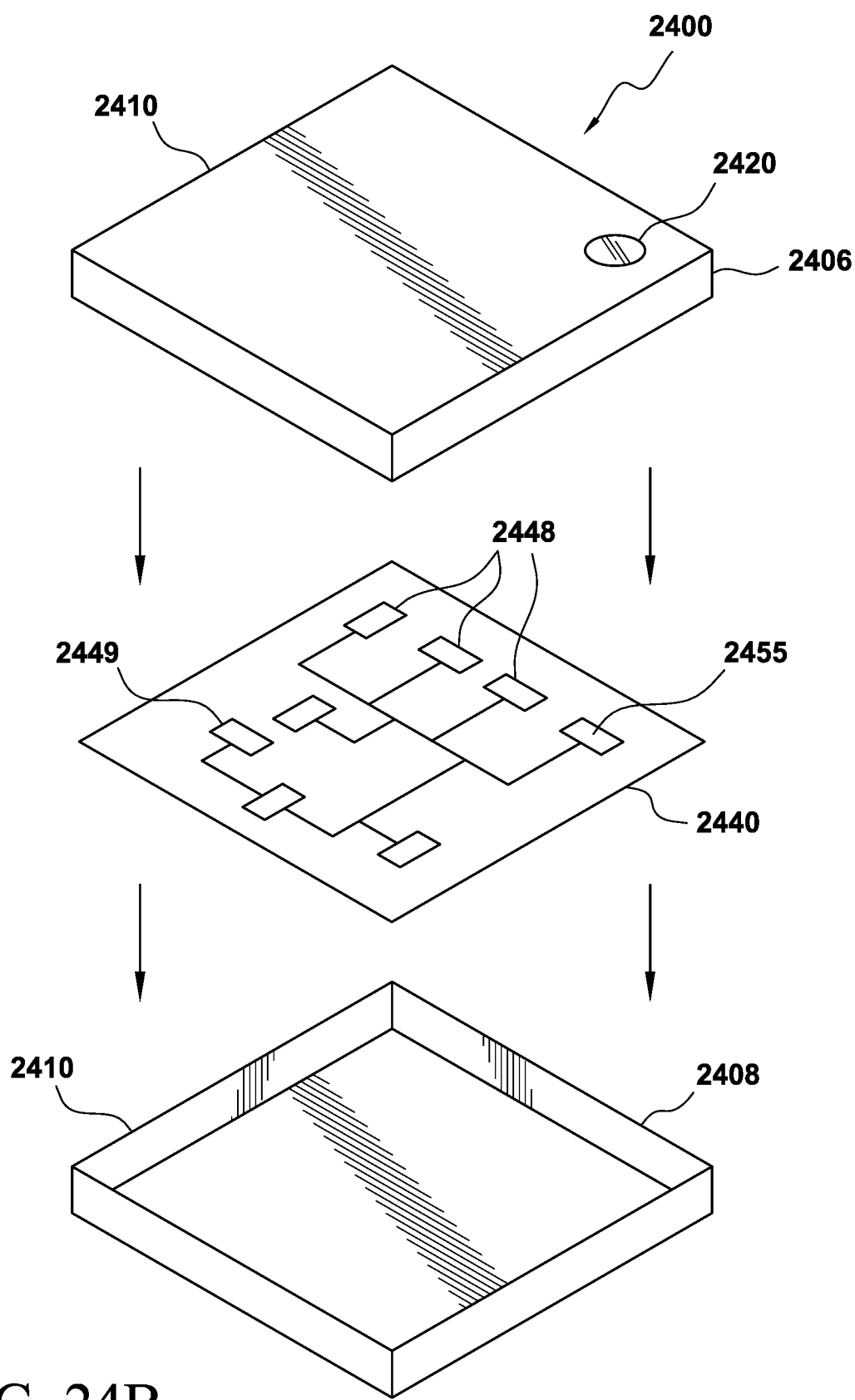
FIG. 24B shows components of a sensor device in accordance with an embodiment.

FIG. 24B shows components of the sensor device of FIG. 2400. Sensor device 2400 includes an upper portion 2406 and a lower portion 2408 of housing 2410. Sensor device 2400 also includes a printed circuit board (PCB) 2440. PCB 2440 includes a plurality of elements 2448, which may include circuit components such as resistors, capacitors, amplifiers, etc., and/or one or more sensors adapted to obtain measurements relating to one or more characteristics such as temperature, salinity, conductivity, motion, etc. For example, PCB 2440 may include one or more of the following: a temperature sensor, a salinity sensor, a conductivity sensor, a motion sensor, a pH sensor, an acceleration sensor (accelerometer), a sonic sensor, etc. PCB 2440 may also include a location sensor (e.g., with GPS capability). In one embodiment, at least one of elements 2448 is a processor adapted to receive measurement data and analyze the measurement data. PCB 2440 also includes a transceiver 2449, which may include an antenna capable of sending and receiving data via wireless communication, for example. In another embodiment, PCB 2440 includes a transmitter. PCB may also include a battery. PCB 2440 also includes a humidity sensor 2455. When housing 2410 is closed, humidity sensor 2455 is located under or proximate hole 2420 such that humidity (water vapor) that enters through hole 2420 is detected by humidity sensor 2455.

PCB 2440 fits into bottom portion 2408. Upper portion 2406 fits onto lower portion 2408, creating a protective seal.

In another embodiment, a sensor device includes a housing that includes an upper portion and a lower portion (such as upper portion 2406 and lower portion 2408). The upper portion and lower portion are adapted to engage and create a partial seal. For example, the upper portion may have first threads that engage with second threads of the lower portion. However, the connection between the upper and lower portions is not a seal. An opening exists between the upper and lower portions that allows water vapor to pass between the exterior and interior of the sensor device but does not allow liquid to pass between the exterior and interior.

Figure 25:
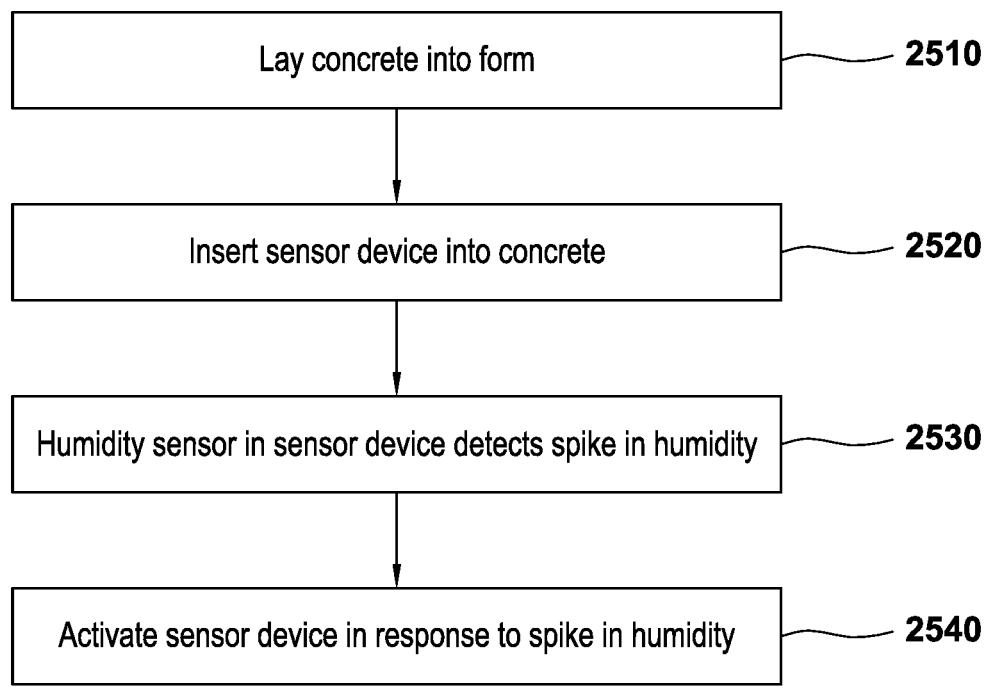
FIG. 25 is a flowchart of a method of detecting humidity in a concrete mixture in accordance with an embodiment.
Figure 26A:
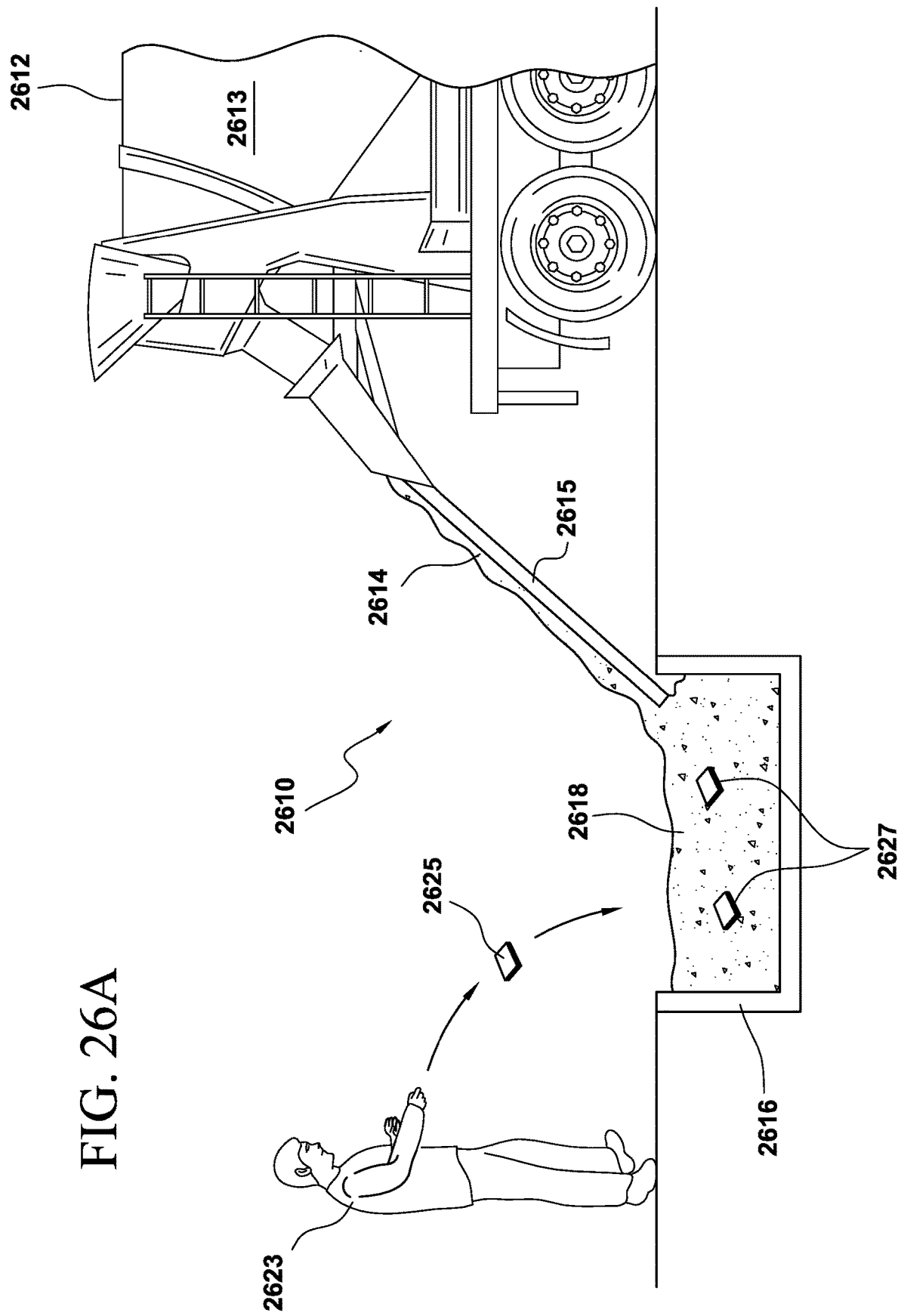
FIG. 26A shows a construction site in accordance with an embodiment.

FIG. 25 is a flowchart of a method of activating a sensor device in accordance with an embodiment. At step 2510, concrete is laid in a form to create a desired structure. FIG. 26A shows a construction site 2610 in accordance with an embodiment. Site 2610 includes a concrete mixing truck 2612 having a drum 2613. Concrete 2614 is poured down a chute 2615 and deposited in a form 2616. The form 2616 thus contains concrete 2618 forming a desired structure.

In the illustrative embodiment, a technician has access to one or more sensor devices that are similar to sensor device 2400 shown in FIG. 24B. Each of these sensor devices is deactivated. When a sensor device is deactivated, any sensors within the sensor device capable of generating data pertaining to various characteristics of concrete (e.g., temperature, salinity, pH, conductivity, etc.) are not activated and do not generate measurement data. The transmitter (e.g., transmitter 2449) within the sensor device does not transmit data. However, even when the sensor device is deactivated, the humidity sensor 2455 continues to function and generates measurements of humidity.

In another embodiment, when a sensor device is deactivated, the transceiver (e.g., transceiver 2449) is active and transmits the humidity measurements generated by humidity sensor 2445 to a remote device (such as data manager 1935). The remote device may be adapted to respond to the humidity measurements and activate the sensor device fully based on the humidity measurements received.

Returning to FIG. 25, at step 2520, a sensor device is inserted into the concrete. In the illustrative embodiment of FIG. 26A, a technician 2623 at the construction site drops or throws a sensor device 2625 into the concrete 2618 in form 2616. For example, sensor device 2625 may be a sensor device similar to sensor device 2400 of FIG. 24B. Prior to the moment when the technician picks up sensor device 2625 and throws it into concrete 2618, the sensor device is deactivated. As seen in FIG. 26A, a plurality of sensor devices 2627 may be inserted into concrete 2618.

Referring to FIG. 24B, before the sensor device 2625 is inserted into the concrete 2618, water vapor enters the sensor device (e.g., through opening or hole 2420). Consequently, the humidity sensor in the sensor device (e.g., humidity sensor 2455 of FIG. 24B) detects a first level of humidity representing the humidity of the surrounding environment.

After sensor device 2625 is inserted (dropped, thrown, etc.) into concrete 2618, water vapor within the concrete enters into sensor device 2625 (through the opening or hole 2420). Consequently, humidity sensor 2455 of sensor device 2625 detects the humidity of the concrete. Typically, the humidity of the concrete is higher than the humidity of the surrounding environment.

Accordingly, at step 2530, a spike in humidity is detected. For example, a processor 2448 on PCB 2440 (in sensor device 2625) may detect a spike in humidity based on predetermined criteria. For example, humidity sensor 2455 may transmit humidity measurements to processor 2448 on PCB 2440, and the processor 2448 may determine that the humidity has experienced a spike defined as a change from a first predetermined level to a second predetermined level; alternatively a spike in humidity may be defined as any change in humidity that exceeds a predetermined amount. Other methods may be used to detect a spike in humidity.

Figure 26B:
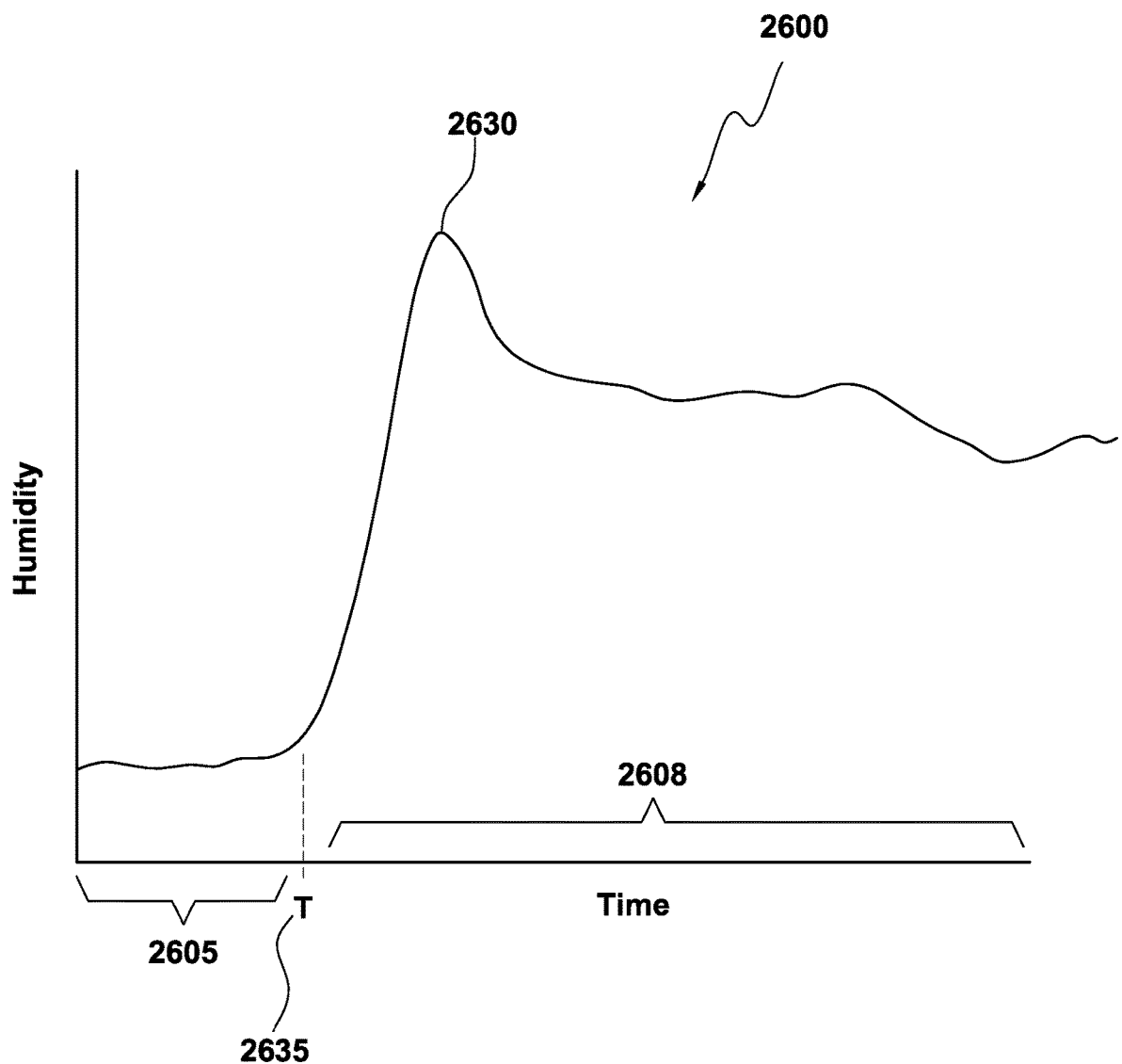
FIG. 26B is a graph showing humidity measurements versus time in accordance with an embodiment.

FIG. 26B shows a graph illustrating humidity measurements obtained by a sensor device in accordance with an embodiment. Specifically, graph 2600 shows humidity measurements obtained by sensor device 2625 versus time. Referring to graph 2600, region 2605 represents the time before the sensor device is inserted into the concrete mixture. During this time, the humidity sensor 2455 detects the humidity of the surrounding environment, which has a first level of humidity (which may vary slightly). At the moment the sensor device is inserted into concrete 2618, the humidity (water vapor) of the concrete enters opening 2420 and is detected by humidity sensor 2455. Because the humidity of concrete 2618 is significantly higher than the humidity of the surrounding air, humidity sensor 2455 detects a spike in humidity when it is inserted into concrete 2618. As a result, the humidity measurements rise to a peak 2630 and then decrease slightly to a second level that is significantly higher than those associated with region 2605. The region 2608 represents the time after the sensor device was inserted into the concrete mixture.

In one embodiment, a time associated with the spike in humidity detected by the sensor device may be determined based on the humidity measurements. This determined time may be used as time zero (T=0) to represent the moment when the sensor device was inserted into the concrete mixture. Mathematical methods of determining a starting time for a significant change in humidity measurements are known. For example, the data may be analyzed and an inflection point in the data may be determined. Alternatively, a curve associated with the humidity measurements may be examined and a point at which the slope of the curve exceeds a predetermined level may be selected as time zero. Other methods may be used. In the illustrative embodiment of FIG. 26B, a time T (2635) is determined based on the spike in the humidity measurements.

Referring again to FIG. 25, at step 2540, the sensor device is activated in response to the spike in the humidity measurements. In the illustrative embodiment, processor 2448 on PCB 2440 activates the sensor device by activating other sensors and components on PCB 2440 in response to the detection of the humidity spike. In another embodiment, a remote device, such as data manager 1935 (communicating with the sensor device via the Internet), may activate the sensor device.

Thus, the sensor device 2625 is activated when humidity sensor 2455 detects the spike in humidity. Specifically, other components and sensors of the sensor device are activated. For example, other sensors (such as sensors capable of detecting temperature, salinity, pH, conductivity, etc) are activated and begin to measure various characteristics of the concrete mixture. Transceiver 2449 begins to transmit the measurement data.

The inventors have further observed that a sonic signal detected by a sensor device typically experiences a drop in magnitude when the sensor device is first inserted into a wet concrete mixture. Sonic signals (sound waves) typically travel more easily through air than through wet concrete. Thus, if a sensor begins in the surrounding air (e.g., the sensor is held by a technician) and then is inserted into a wet concrete mixture, any sonic sensor on the sensor device that is monitoring sonic signals typically experiences signal loss starting at the moment the sensor device is inserted into the wet concrete mixture. The inventors have determined that this signal loss can be utilized to determine when to activate a sensor device.

Figure 26C:
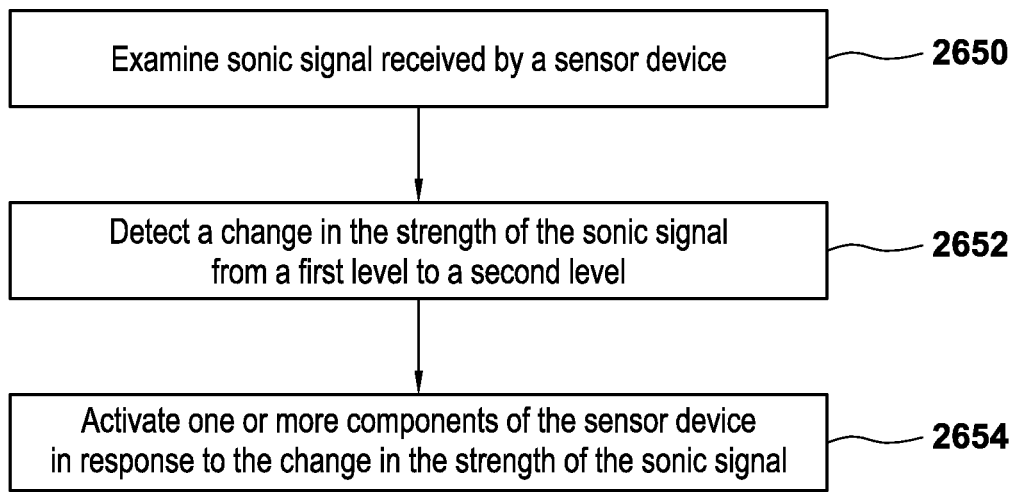
FIG. 26C is a flowchart of a method in accordance with an embodiment.

FIG. 26C is a flowchart showing a method of activating components of a sensor device in accordance with another embodiment. At step 2650, a sonic signal (e.g., a sound wave) received by a sensor device is examined. Referring again to the illustrative embodiment of FIG. 26A, suppose that sensor device 2625 includes a sonic sensor adapted to detect sonic signals (sound waves). A processor of sensor device 2625 monitors and analyzes the sonic signals received. For example, sensor device 2625 may include elements similar to elements 2448 on PCB 2440; the elements may include a sonic sensor and a processor. Alternatively, the sonic signals detected may be transmitted wirelessly to a remote processor adapted to analyze the sonic signals.

Figure 26D:
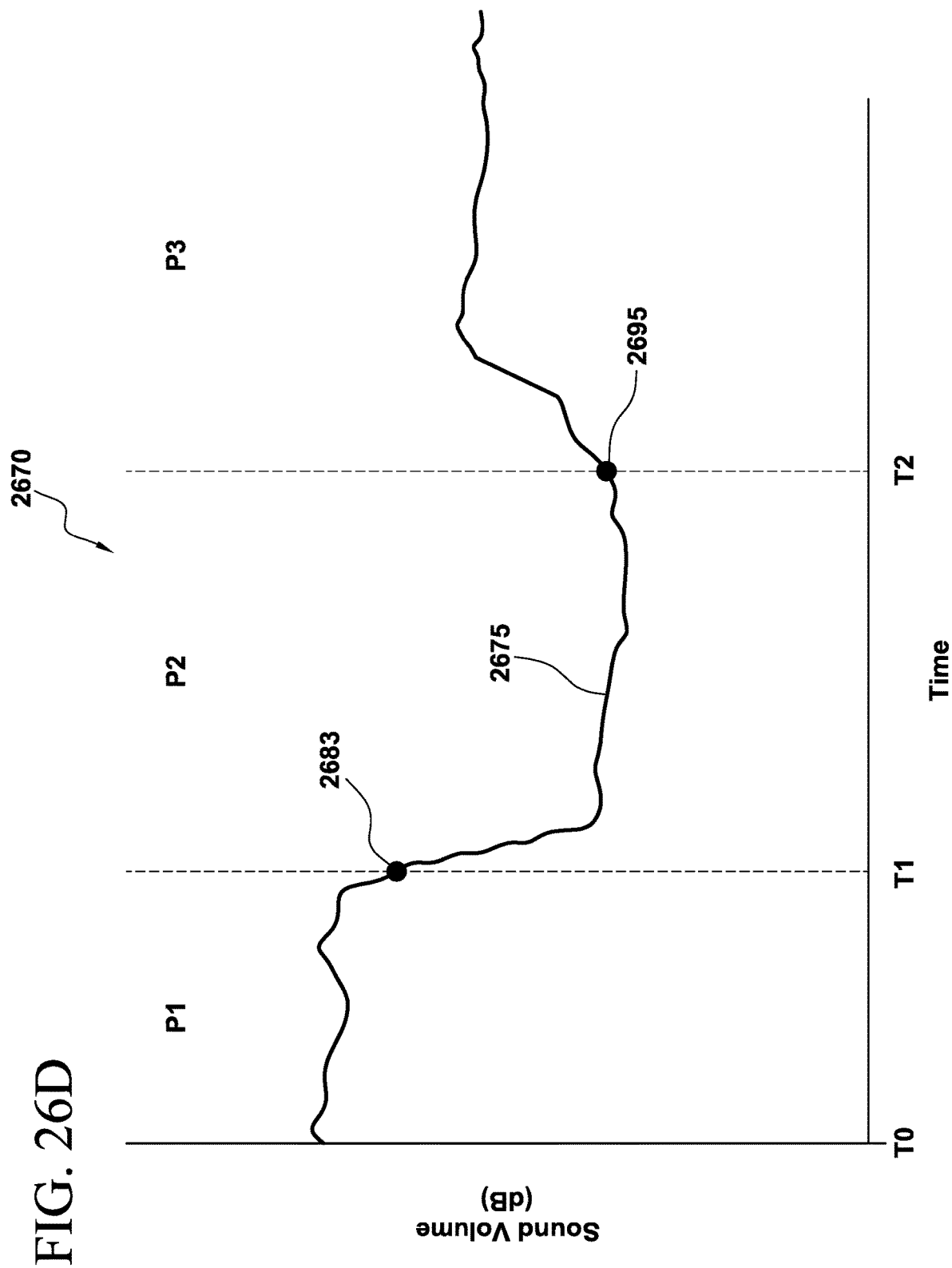
FIG. 26D is a graph showing measurements of a sonic signal versus time in accordance with an embodiment.

FIG. 26D shows a graph 2670 of a sonic signal 2675 that may be detected by a sonic sensor on a sensor device in accordance with an embodiment. In the illustrative embodiment, the sonic sensor begins to detect sonic signals at time T0. The sensor device is held by a technician at time T0 until about time T1. During the period P1 between time T0 and time T1, the sonic signal 2675 has a magnitude (in decibels) around a first initial level, reflecting the sonic signals (including background noise, talking, and any other noises) in the air surrounding the technician.

Suppose now that the technician inserts the sensor device into a concrete mixture at about time T1. At step 2652, a change in the strength of the sonic signal (sound wave) from a first level to a second level is detected. Specifically, after the sensor is embedded in the concrete mixture, the sonic signal detected by the sonic sensor on the sensor device decreases in strength. Thus, referring to graph 2670, the strength of the sonic signal 2675 decreases after time T1 (associated with point 2683) to a second level. The sonic signal displays a signal strength having a second level (which is lower than the first level) between approximately T1 and approximately time T2. The processor of the sensor device 2625 determines that a decrease in the strength of the sonic signal has been detected.

At step 2654, one or more components of the sensor device are activated in response to the change in the strength of the sonic signal. In response to the determination that the strength of the sonic signal has decreased from the first level to the second level, one or more components of the sensor device 2625 are activated. For example, one or more of a temperature sensor, a humidity sensor, a salinity sensor, an accelerometer, a pH sensor, a conductivity sensor, etc., on sensor device 2625 may be activated.

As the concrete mixture dries, the properties of the concrete mixture may change; for example, the dry concrete mixture may transmit sound signals more easily than the wet concrete. As a result, the sonic sensor on the sensor device 2625 may detect an increase in the strength of the sonic signals as the concrete sets. In the illustrative embodiment of FIG. 26D, the strength of sonic signal 2675 increases starting at about time T2 (associated with point 2696 on graph 2670). The strength of sonic signal 2675 rises to a third level (different from the second level). One or more components of the sensor device 2625 may be activated based on the detection of the signal from the second level to the third level.

Figure 27A:
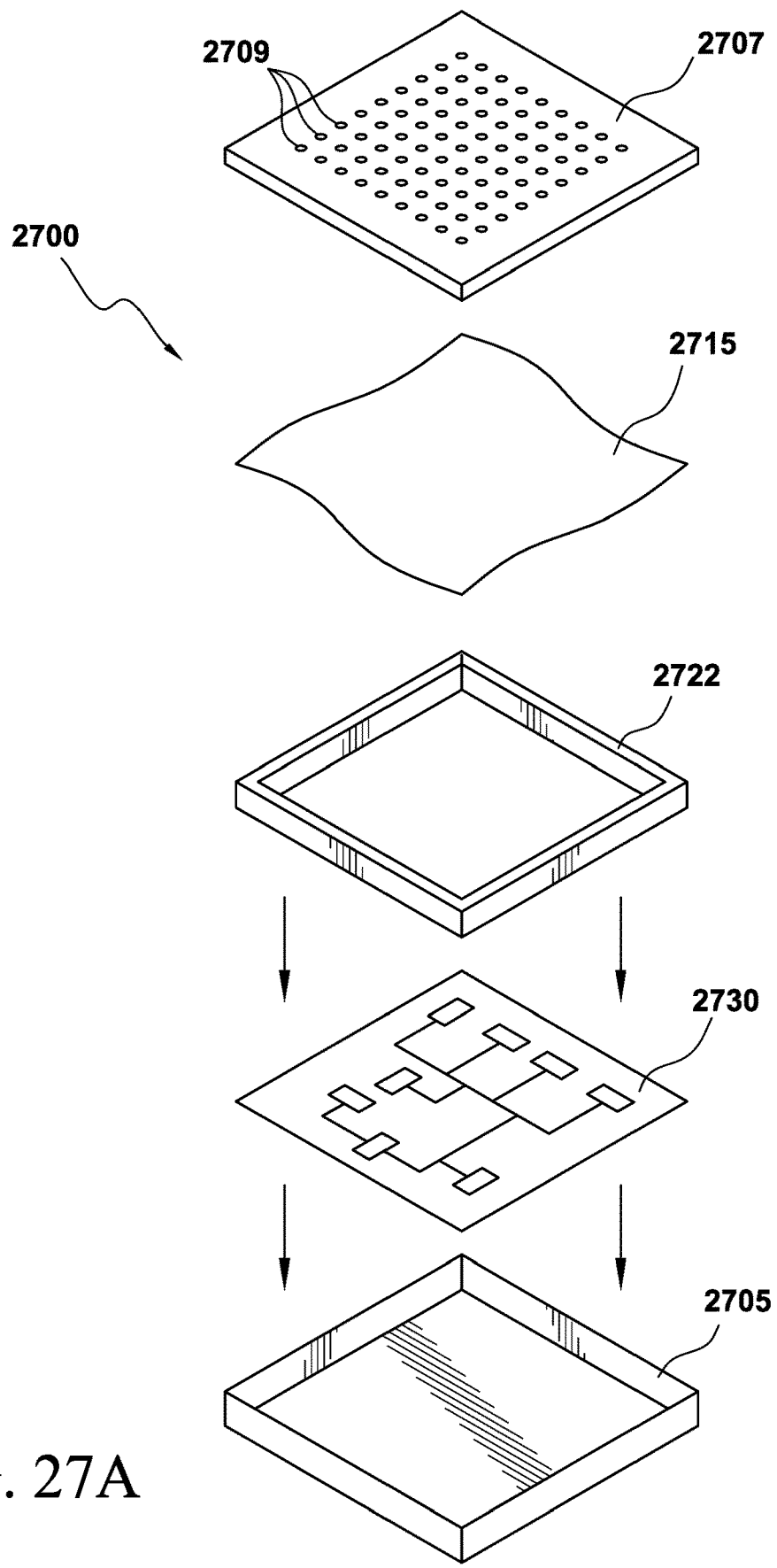
FIGS. 27A-27C show components of a sensor device in accordance with another embodiment.
Figure 27B:
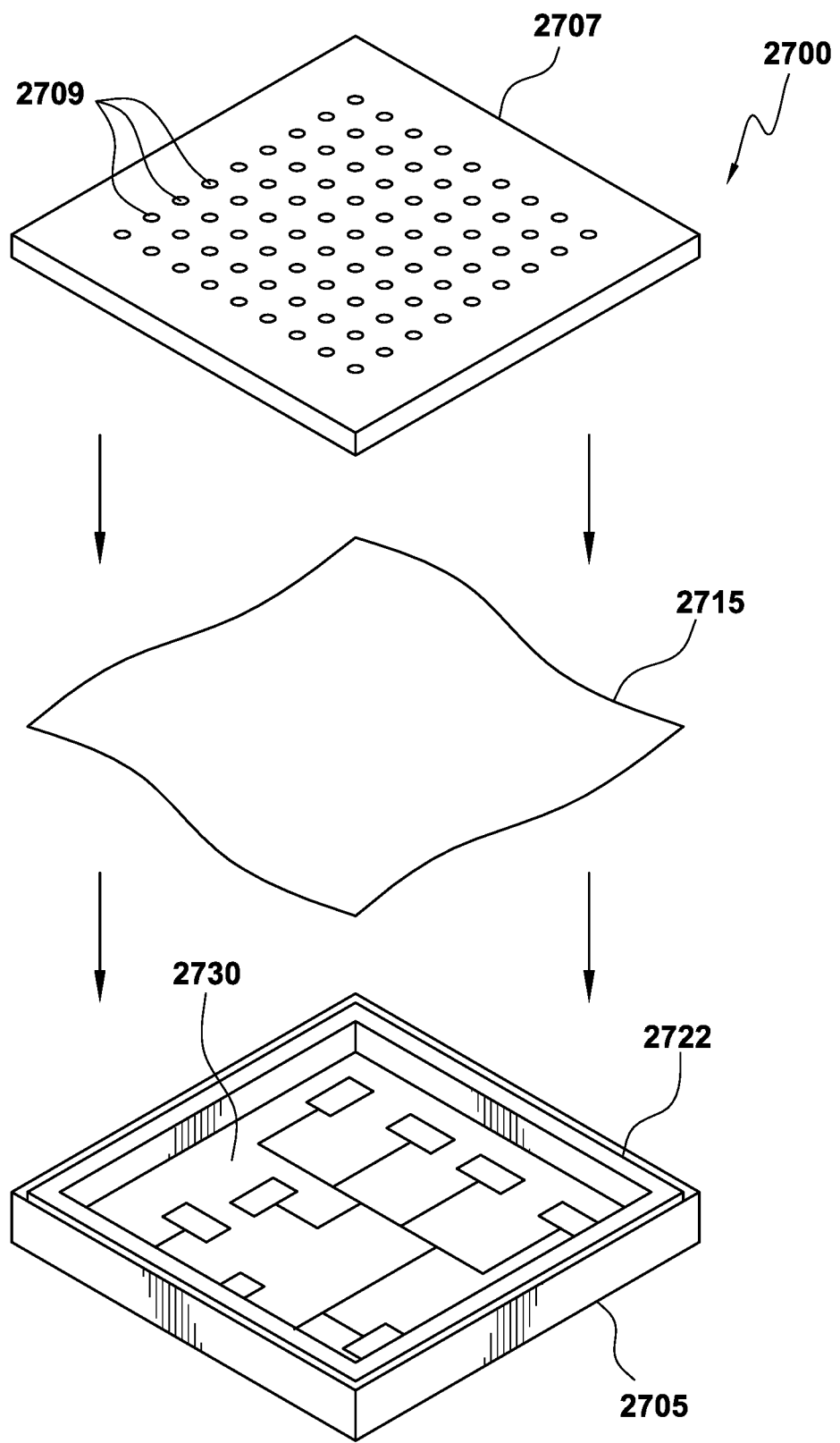
Figure 27C:
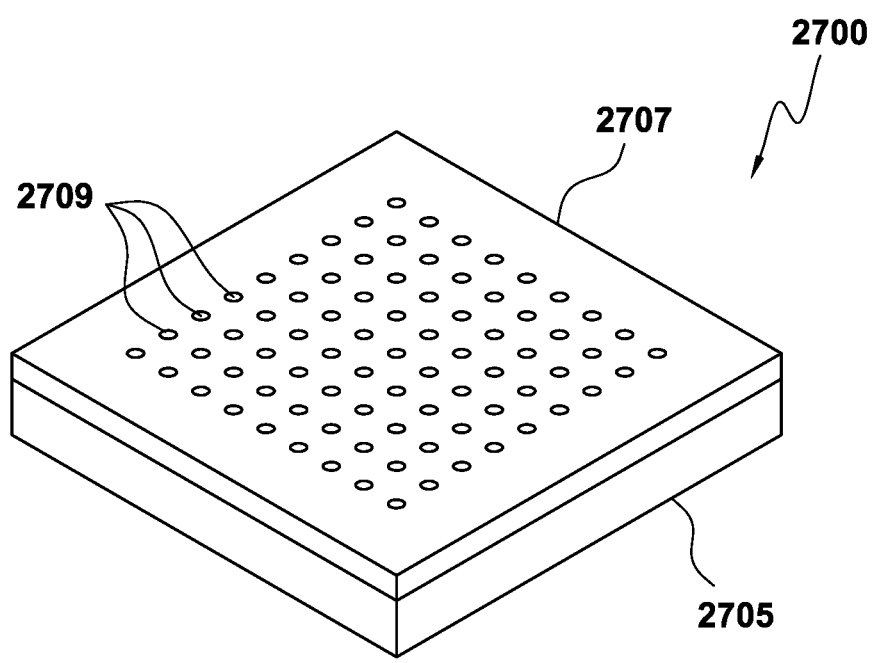

FIGS. 27A-27C show components of a sensor device in accordance with another embodiment. As shown in FIG. 27A, sensor device 2700 includes a housing that includes an upper portion 2707 and a lower portion 2705. Upper portion 2707 and lower portion 2705 may be formed from plastic, metal, or other material. Sensor device 2700 also includes a waterproof layer 2715, a support 2722, and a sensor component 2730.

Upper portion 2707 of housing includes a plurality of holes 2709. In the illustrative embodiment of FIG. 27A, upper portion 2707 includes seventy-two holes arranged in an 8×9 array. In other embodiments, upper portion 2707 of the housing may include any number of holes arranged in any configuration.

Each hole may be any size. For example, each hole may between 0.5 and 6.0 millimeters wide. The holes are adapted to allow humidity to pass through from the exterior of sensor device 2700 to the interior of the sensor device. In some embodiments, the holes may allow liquid and/or concrete to pass through. In other embodiments, the holes do not allow liquid or concrete to pass through.

Waterproof layer 2715 is made of a waterproof, breathable material that allows humidity (water vapor) to pass through the layer but does not allow liquid or concrete to pass through. For example, waterproof layer 2715 may be made waterproof, breathable fabric membrane such as Gore-Tex or other similar material.

Sensor component 2730 includes one or more sensors adapted to measure one or more characteristics of a surrounding material (such as concrete, water, etc.) Sensor component 2730 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Sensor component 2730 may also include a processor. Sensor component 2730 may also include a transceiver, or may include a transmitter and a receiver. Sensor component 2730 may also include a battery. Alternatively, a battery or other power source may be disposed elsewhere in sensor device 2700.

Support 2722 is disposed between sensor component 2730 and waterproof layer 2715. Support 2722 separates waterproof layer 2715 from sensor component 2730 and thereby protects the sensors (and other electronics) of sensor component 2730 from water, liquids, concrete, etc. that may be proximate waterproof layer 2715. Thus support 2722 may maintain a predetermined distance between waterproof layer 2715 and sensor component 2730.

In the illustrative embodiment, sensor device 2700 is assembled by fitting sensor component 2730 into lower portion 2705 of the housing, and placing support 2722 above sensor component 2730, as illustrated in FIGS. 27A and 27B. Waterproof layer 2715 is placed above support 2722, and upper portion 2707 is fitted over lower portion 2705, as illustrated in FIGS. 27B and 27C. Upper portion 2707 and lower portion 2705 may form a seal when fitted together. FIG. 27C shows sensor device 2700 in a fully assembled state.

Figure 28:
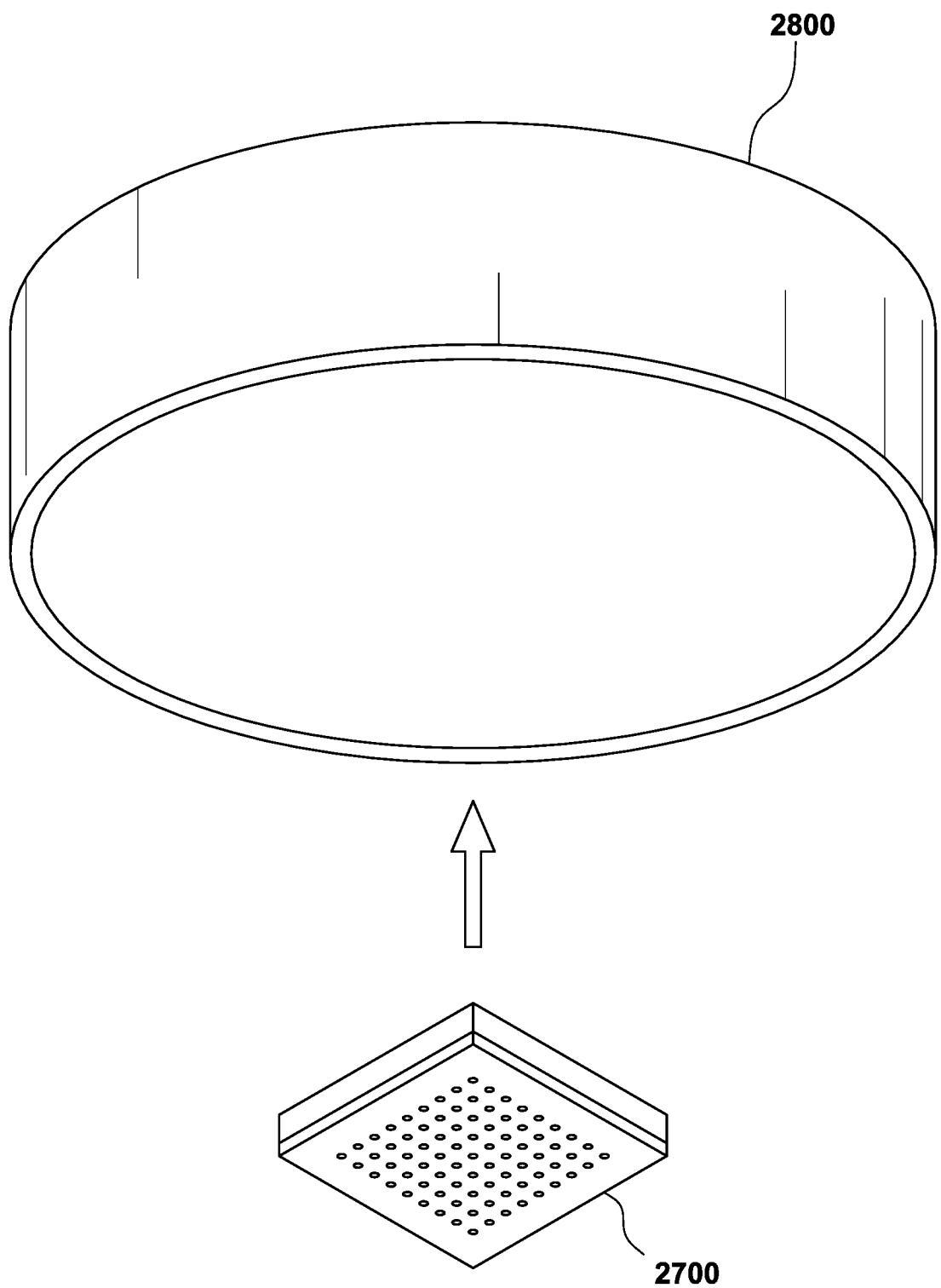
FIG. 28 shows a sensor device and a cap adapted to be placed onto a standard concrete test cylinder in accordance with an embodiment.

In accordance with an embodiment, sensor device 2700 may be attached to a cap adapted to fit onto a standard concrete test cylinder. FIG. 28 shows sensor device 2700 and a cap 2800 adapted to be placed onto a standard concrete test cylinder. For example, sensor device 2700 may be attached to an interior surface of cap 2800 in the manner shown in FIG. 12. In the manner described herein, sensor device 2700 may then obtain measurements relating to one or more characteristics of the concrete mixture in the test cylinder. Sensor device 2700 may transmit the measurement data wirelessly.

It has been observed that certain components of a sensor device such as those described herein can sometimes suffer damage if the sensor device is dropped, thrown, or otherwise experiences a rapid or jarring movement. In particular, it has been observed that if a sensor device is thrown or dropped into a concrete mixture at a construction site, the battery within the sensor device may be damaged by the associated rapid movements. Therefore, a need exists for a sensor device design that protects a battery from rapid, jarring movements that may occur when the sensor device is thrown, dropped, etc.

Figure 29A:
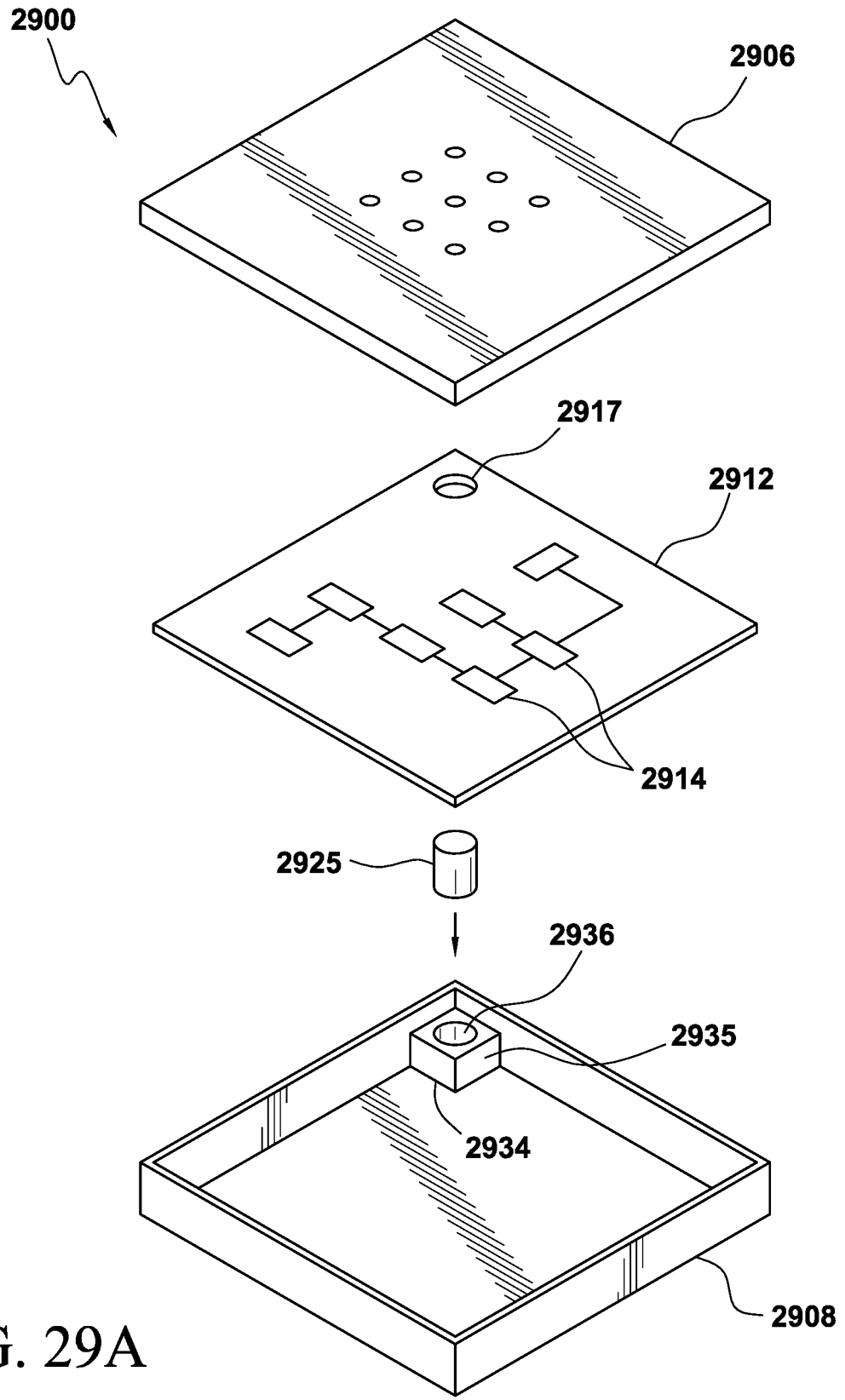
FIGS. 29A-29D show a sensor device in accordance with another embodiment.

FIGS. 29A-29D show a sensor device in accordance with another embodiment. FIG. 29A shows components of a sensor device 2900. Sensor device 2900 includes a housing that includes an upper portion 2906 and a lower portion 2908. Upper portion 2906 may include one or more holes that allow water vapor (but not liquid or concrete) to pass through. Sensor device 2900 also includes a sensor component 2912 which includes one or more sensors. For example, sensor component 2912 may be, for example, a printed circuit board (PCB) containing circuit components such as resistors, capacitors, amplifiers, etc., and/or one or more sensors 2914 adapted to obtain measurements relating to one or more characteristics such as temperature, salinity, conductivity, motion, etc. For example, the sensor component 2912 may include one or more of the following: a temperature sensor, an accelerometer, a pH sensor, an inductance sensor, an impedance or resistivity sensor, a sonic sensor, a pressure sensor, a conductivity sensor, a salinity sensor, a humidity sensor, or an elevation sensor. One example of the temperature sensor is a miniature-sized temperature logger "SMARTBUTTON" (ACR SYSTEMS INC.). In one embodiment, a salinity sensor may include a chloride ion electrode, for example. Sensor component 2912 may also include a transceiver, or may include a transmitter and a receiver.

Sensor component 2917 also includes a hole 2917 in a selected location. In the illustrative embodiment of FIGS. 29A-29D, hole 2917 is proximate a corner of sensor component 2912; however, in other embodiments, hole 2917 may be at a different location on sensor component 2912.

Sensor device 2900 also includes a battery 2925 adapted to provide power to various sensors and other electronic elements of sensor component 2912.

Hole 2917 of sensor component 2912 is adapted to receive battery 2925. Preferably, the size and shape of hole 2917 are selected such that battery 2925 fits snugly through hole 2917 with little or no space between the battery and the edge of the hole.

Lower portion 2908 of the housing includes a casing 2934 disposed in a selected location. While in the illustrative embodiment, casing 2934 is disposed in a corner of the lower portion 2908, in other embodiments, casing 2934 may be located at any selected location of the housing. Casing 2934 includes a solid peripheral portion 2935 and a central cavity 2936. Cavity 2936 is adapted to receive and hold at least a portion of battery 2925. Preferably, the size and shape of cavity 2936 are selected such that battery 2925 fits snugly into cavity 2936 with little or no space between the battery and the side of cavity 2936, to ensure that battery 2925 does not move or shake when placed in the cavity.

Figure 29B:
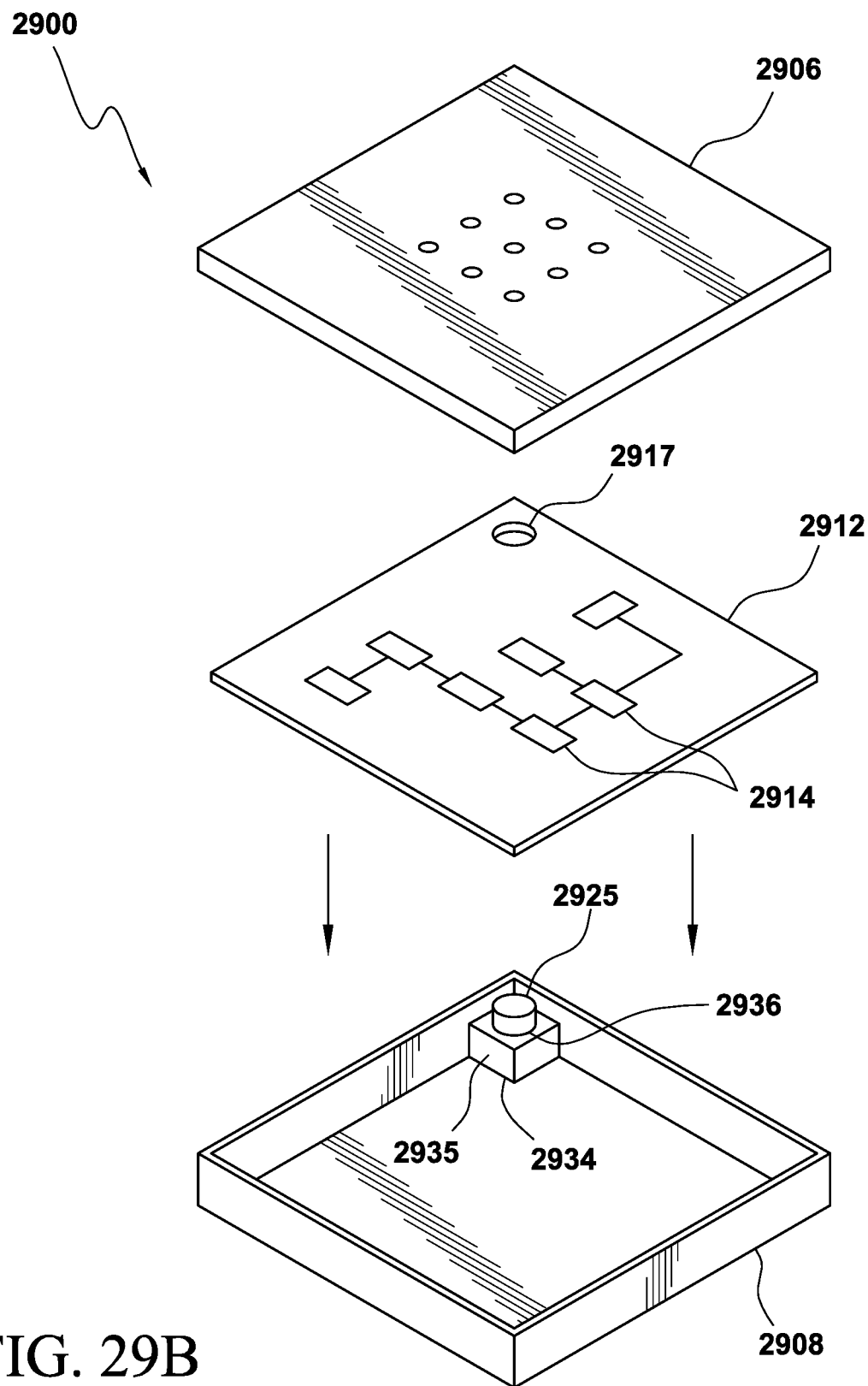
Figure 29C:
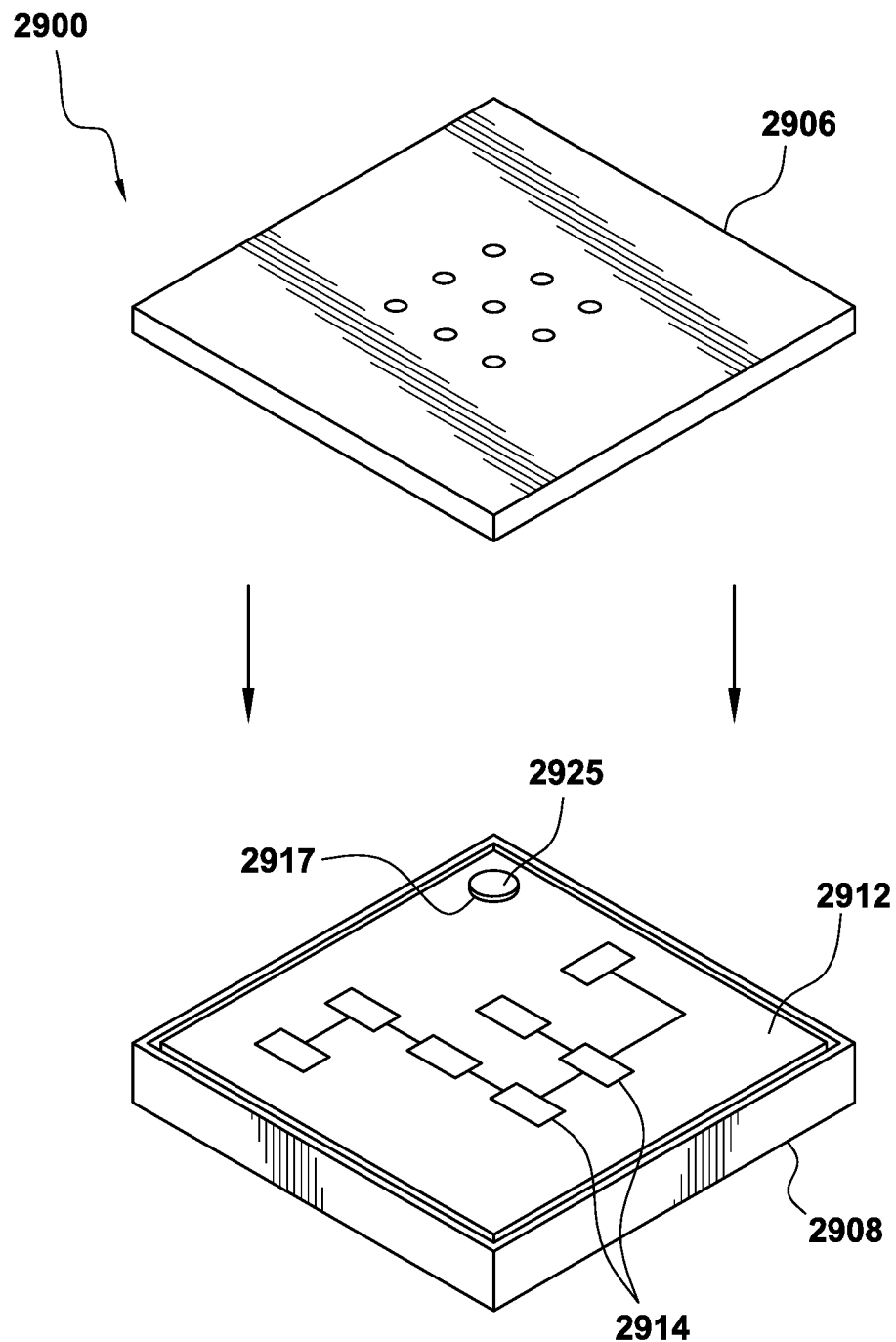
Figure 29D:
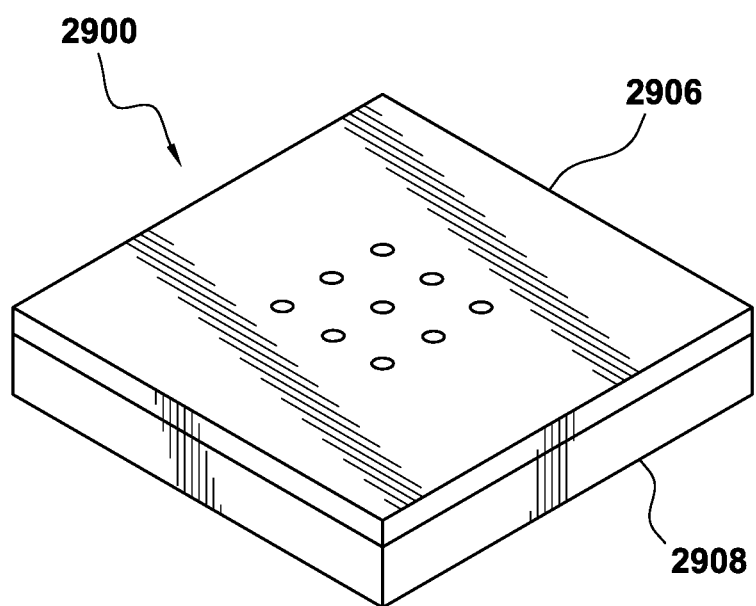

Referring to FIGS. 29B-29D, sensor device 2900 is assembled by placing battery 2925 into cavity 2936. FIG. 29B shows components of sensor device 2900 after battery 2935 has been placed into cavity 2936. Sensor component 2912 is then placed into lower portion 2908 of the housing. Battery 2925 passes through hole 2917, allowing sensor component 2912 to fit into lower portion 2908 of the housing. FIG. 29C shows sensor device 2900 after sensor component 2912 has been placed into lower portion 2908 of the housing. Batter 2925 is visible and may protrude from hole 2917 of sensor component 2912.

Upper portion 2906 of the housing is then secured onto lower portion 2908. Upper portion 2906 and lower portion 2908 may form a seal when fitted together. FIG. 29D shows sensor device 2900 in a fully assembled state.

Advantageously, the placement of battery 2925 within cavity 2936 and hole 2917 secures battery 2925 in place and prevents battery 2925 from moving within sensor device 2900 if sensor device 2900 is moved. This design advantageously protects the battery from being damaged if sensor device 2900 is dropped, thrown, or is otherwise moved in a jarring manner.

Figure 30A:
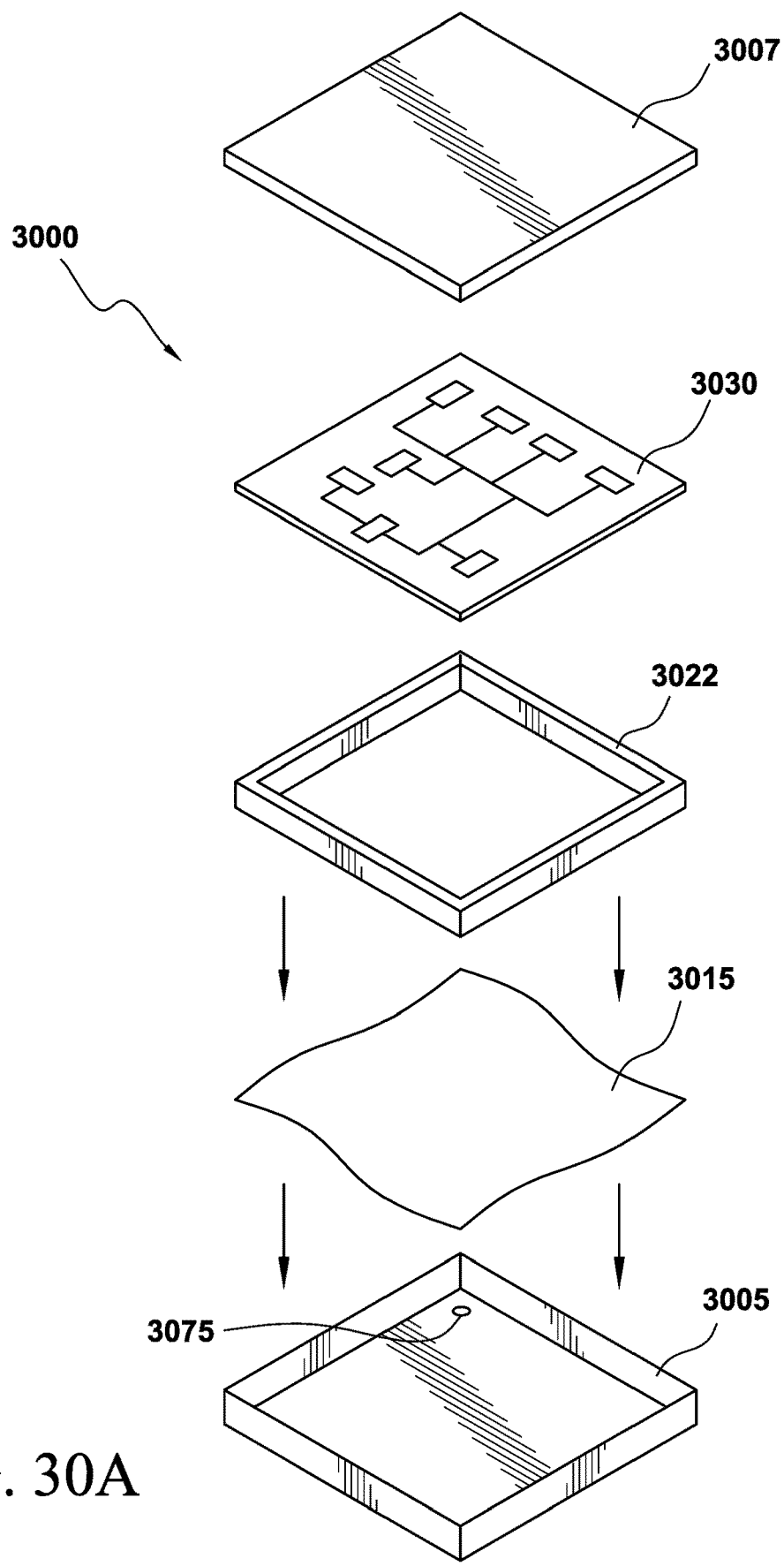
FIGS. 30A-30C show components of a sensor device in accordance with another embodiment.
Figure 30B:
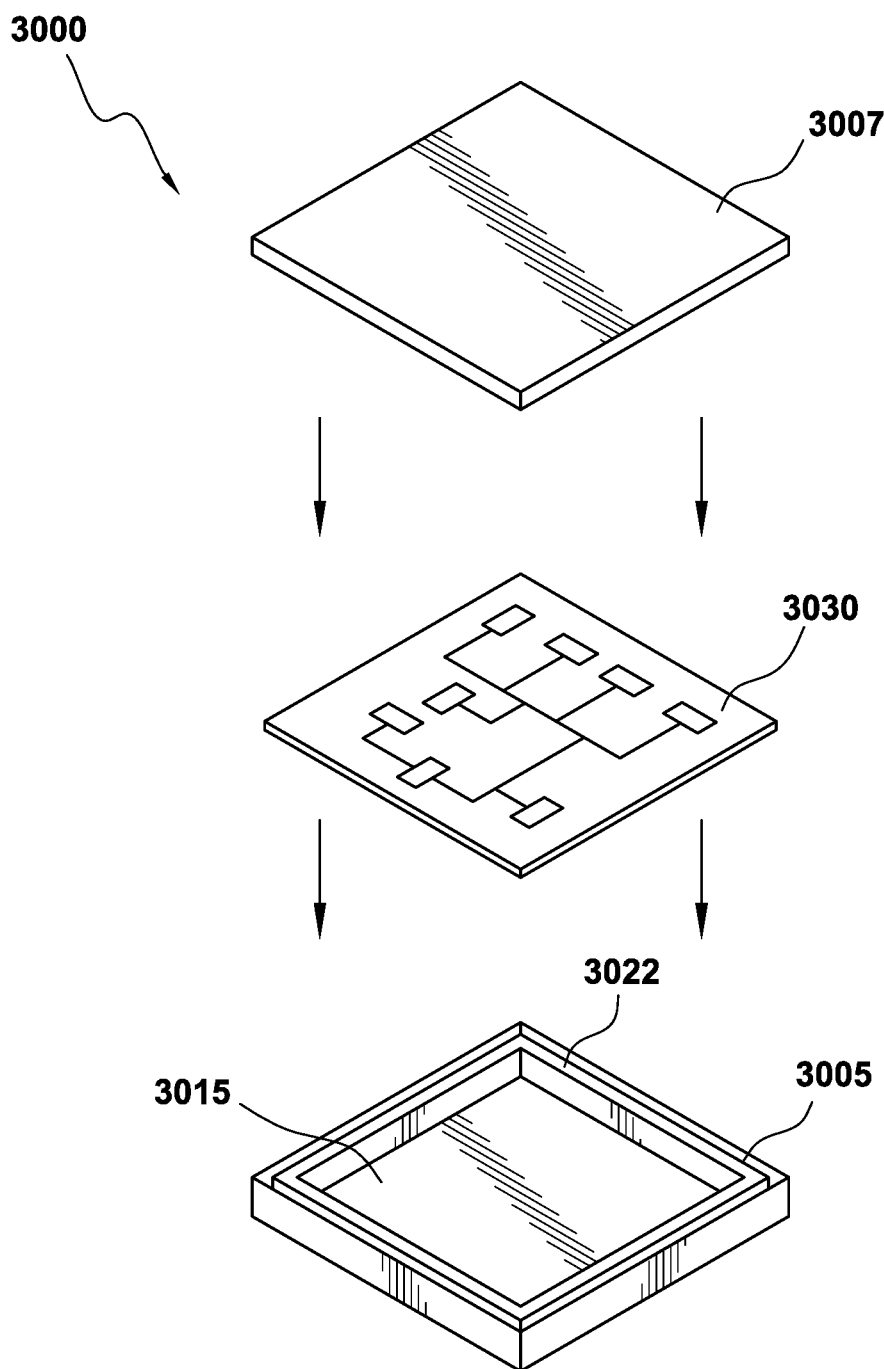
Figure 30C:
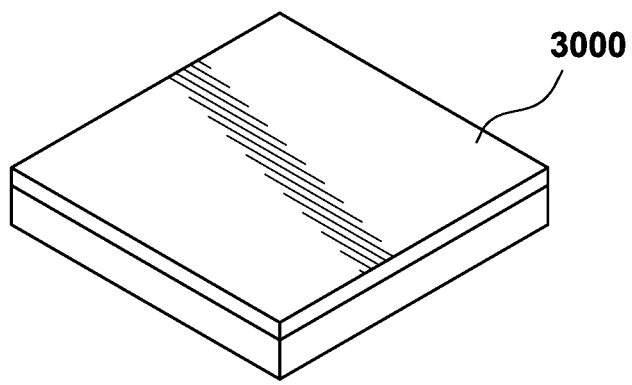

FIGS. 30A-30C show components of a sensor device in accordance with another embodiment. As shown in FIG. 30A, sensor device 3000 includes a housing that includes an upper portion 3007 and a lower portion 3005. Upper portion 3007 and lower portion 3005 may be formed from plastic, metal, or other material. Sensor device 3000 also includes a waterproof layer 3015, a support 3022, and a sensor component 3030.

Upper portion 3007 of housing does not include any holes. Therefore, upper portion 3007 of the housing does not allow humidity to pass through from the exterior of sensor device 3000 to the interior of the sensor device.

Lower portion 3005 includes a single hole 3075 that allows humidity (water vapor) to pass into the interior of sensor device 3000 but does not allow water, concrete, or other liquids to enter. For example, hole 3075 may be a hole having a diameter of between about 1.0 millimeters and 3.0 millimeters, preferably about 2.0 millimeters. Other diameters may be used.

Sensor component 3030 includes one or more sensors adapted to measure one or more characteristics of a surrounding material (such as concrete, water, etc.) Sensor component 3030 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Sensor component 3030 may also include a processor. Sensor component 3030 may also include a transceiver, or may include a transmitter and a receiver. Sensor component 3030 may also include a battery. Alternatively, a battery or other power source may be disposed elsewhere in sensor device 3000.

Waterproof layer 3015 is made of a waterproof, breathable material that allows humidity (water vapor) to pass through the layer but does not allow liquid or concrete to pass through. For example, waterproof layer 3015 may be made waterproof, breathable fabric membrane such as Gore-Tex or other similar material.

Support 3022 is disposed between sensor component 3030 and waterproof layer 3015. Support 3022 separates waterproof layer 3015 from sensor component 3030 and thereby protects the sensors (and other electronics) of sensor component 3030 from water, liquids, concrete, etc. that may be proximate waterproof layer 3015. Thus support 3022 may maintain a predetermined distance between waterproof layer 3015 and sensor component 3030.

In the illustrative embodiment, sensor device 3000 is assembled by fitting waterproof layer 3015 and support 3022 into lower portion 3005 of the housing, as illustrated in FIGS. 30A-30B. Sensor component 3030 is then placed above support 3022, and upper portion 3007 is fitted over lower portion 3005, as illustrated in FIGS. 30B and 30C. Upper portion 3007 and lower portion 3005 may form a seal when fitted together. FIG. 30C shows sensor device 3000 in a fully assembled state.

Figure 31A:
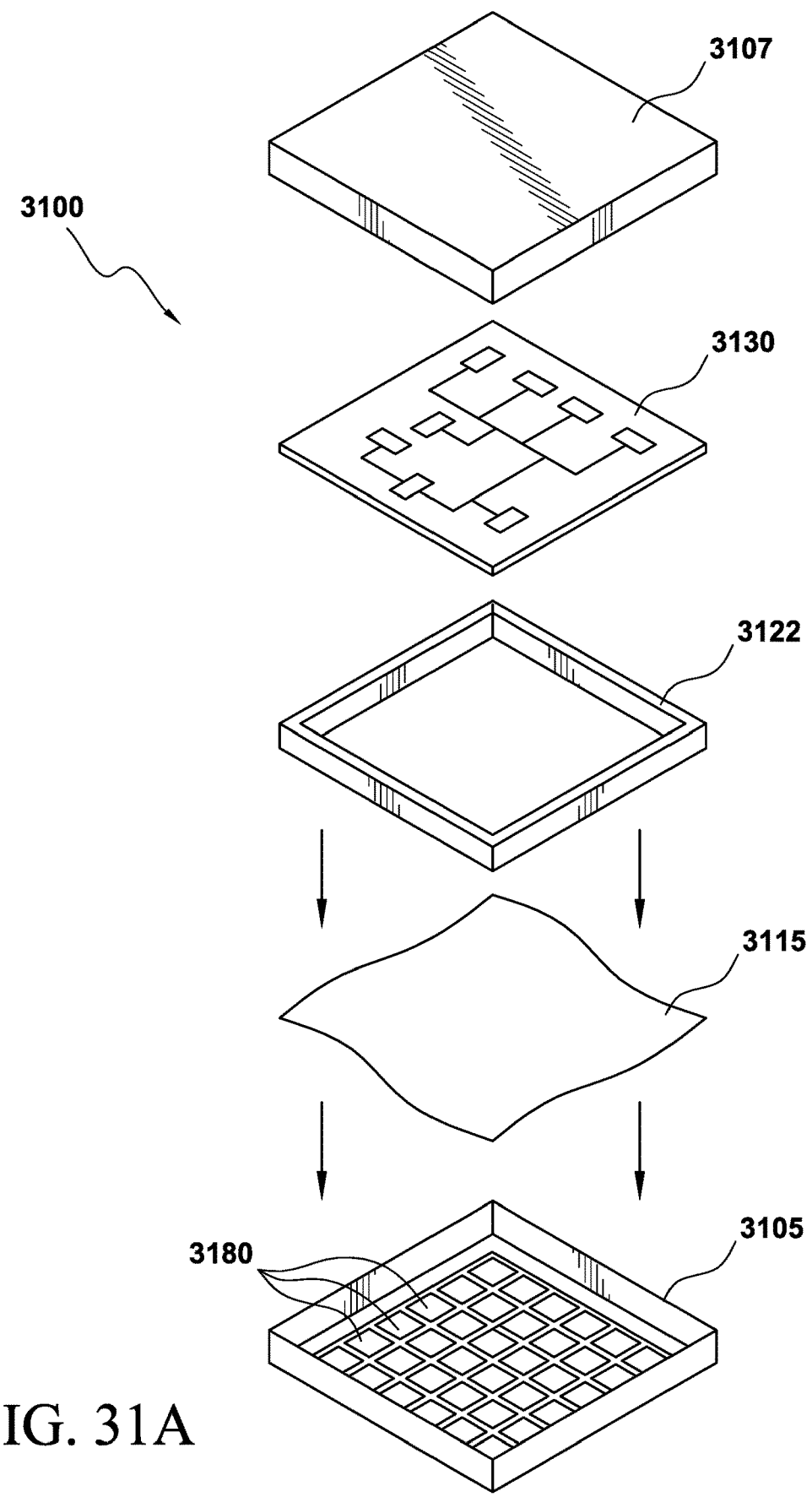
FIGS. 31A-31D show components of a sensor device in accordance with another embodiment.
Figure 31B:
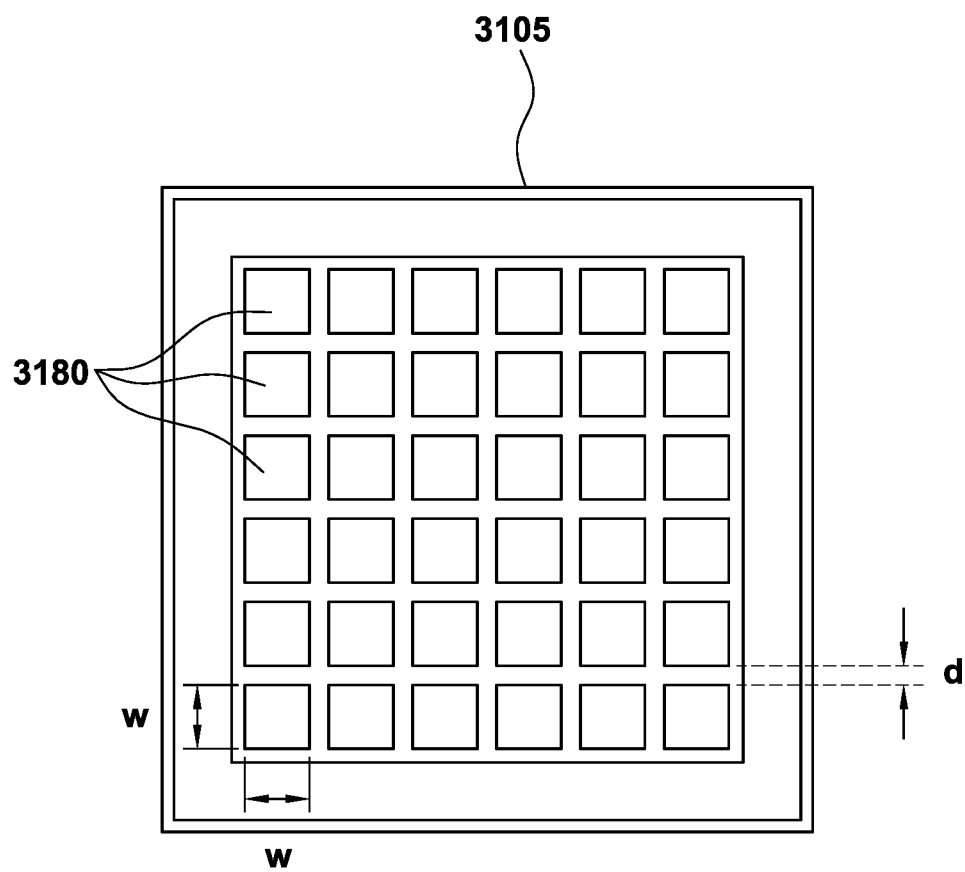

FIGS. 31A-31D show components of a sensor device in accordance with another embodiment. As shown in FIG. 31A, sensor device 3100 includes a housing that includes an upper portion 3107 and a lower portion 3105. Upper portion 3107 and lower portion 3105 may be formed from plastic, metal, or other material. Sensor device 3100 also includes a waterproof layer 3115, a support 3122, and a sensor component 3130.

Upper portion 3107 of housing does not include any holes. Therefore, upper portion 3107 of the housing does not allow humidity to pass through from the exterior of sensor device 3100 to the interior of the sensor device.

Lower portion 3105 includes an array of holes 3180. Holes 3180 allow liquid and humidity (water vapor) to pass into the interior of sensor device 3100. An array of any size may be used. For example, a 5×5 array of holes, a 6×6 array of holes, a 5×6 array of holes, or other configuration may be used. In one embodiment, each hole 3180 may be a square or rectangular hole having sides of length between 5.5 millimeters and 6.5 millimeters, preferably a square hole having sides of length 6.1 millimeters. Other shapes and dimensions may be used. Lower portion 3105 may include an array having holes of uniform shape and size, or may have an array with holes of different shapes and sizes. For example, holes at the corners and around the edges of a 6×5 array may be smaller and/or have shapes that are different from the sizes and shapes of the holes in the center of the array.

Sensor component 3130 includes one or more sensors adapted to measure one or more characteristics of a surrounding material (such as concrete, water, etc.) Sensor component 3130 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, sound, etc. Sensor component 3130 may also include a processor. Sensor component 3130 may also include a transceiver, or may include a transmitter and a receiver. Sensor component 3130 may also include a battery. Alternatively, a battery or other power source may be disposed elsewhere in sensor device 3100.

Waterproof layer 3115 is made of a waterproof, breathable material that allows humidity (water vapor) to pass through the layer but does not allow liquid or concrete to pass through. For example, waterproof layer 3115 may be made a waterproof, breathable fabric membrane such as Gore-Tex or other similar material.

Support 3122 is disposed between sensor component 3130 and waterproof layer 3115. Support 3122 separates waterproof layer 3115 from sensor component 3130 and thereby protects the sensors (and other electronics) of sensor component 3130 from water, liquids, concrete, etc. that may be proximate waterproof layer 3115. Thus support 3122 may maintain a predetermined distance between waterproof layer 3115 and sensor component 3130.

Figure 31C:
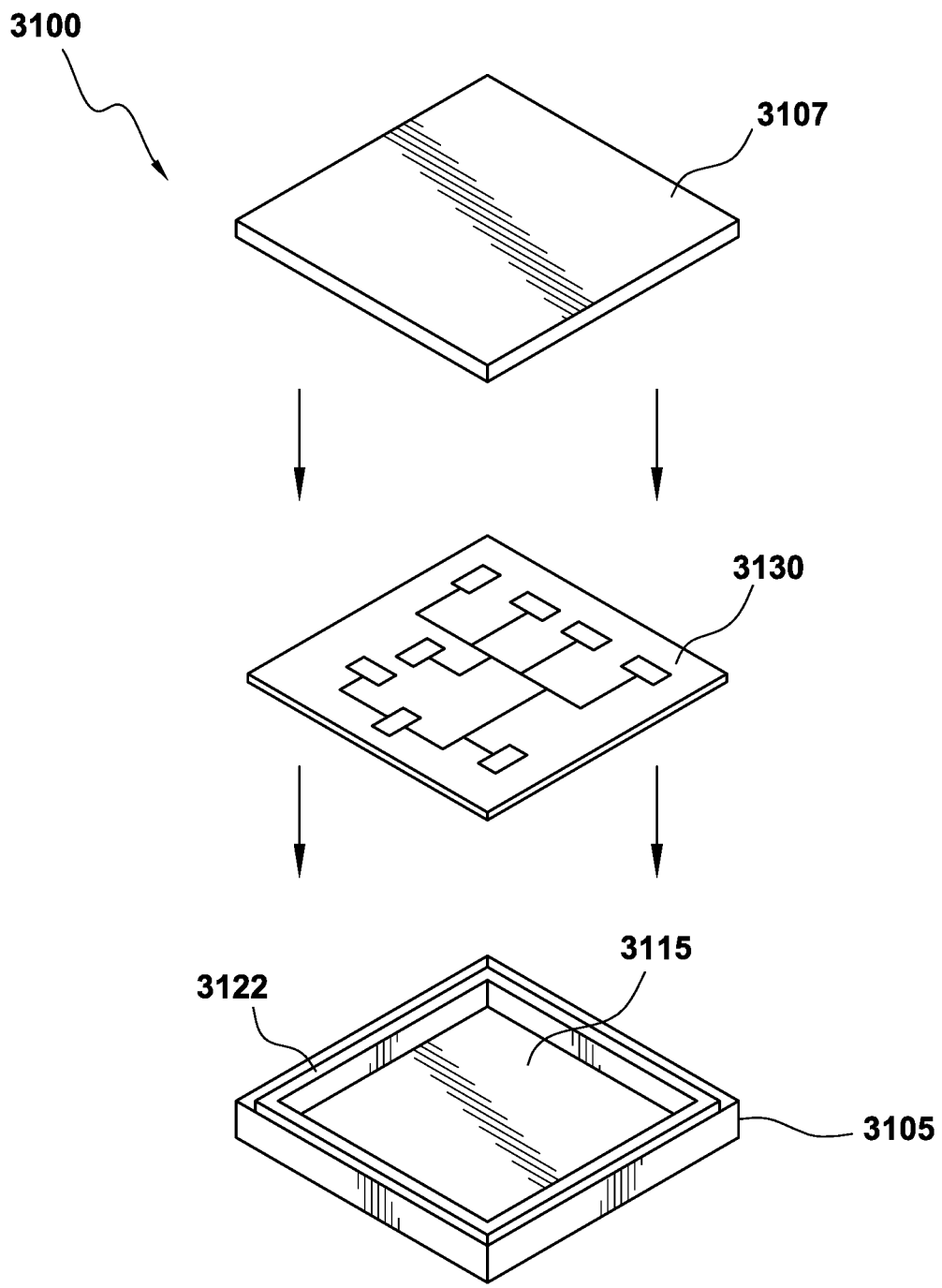
Figure 31D:
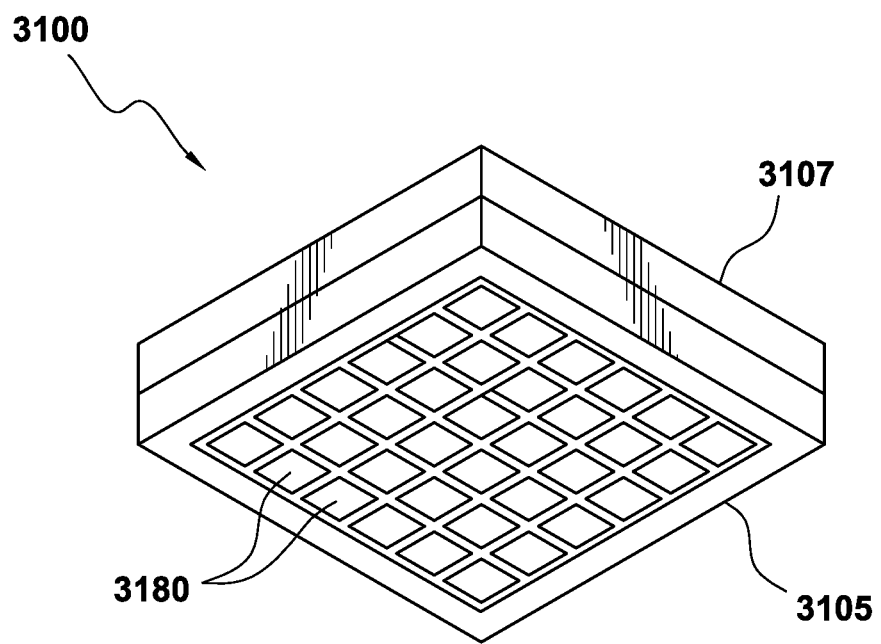

In the illustrative embodiment, sensor device 3100 is assembled by fitting waterproof layer 3115 and support 3122 into lower portion 3105 of the housing, as illustrated in FIGS. 30A and 30C. Sensor component 3130 is then placed above support 3122, and upper portion 3107 is fitted over lower portion 3105, as illustrated in FIGS. 31C and 31D. Upper portion 3107 and lower portion 3105 may form a seal when fitted together. FIG. 31D shows sensor device 3100 in a fully assembled state. Lower portion 3105 and holes 3180 is visible in FIG. 31D.

Figure 32A:
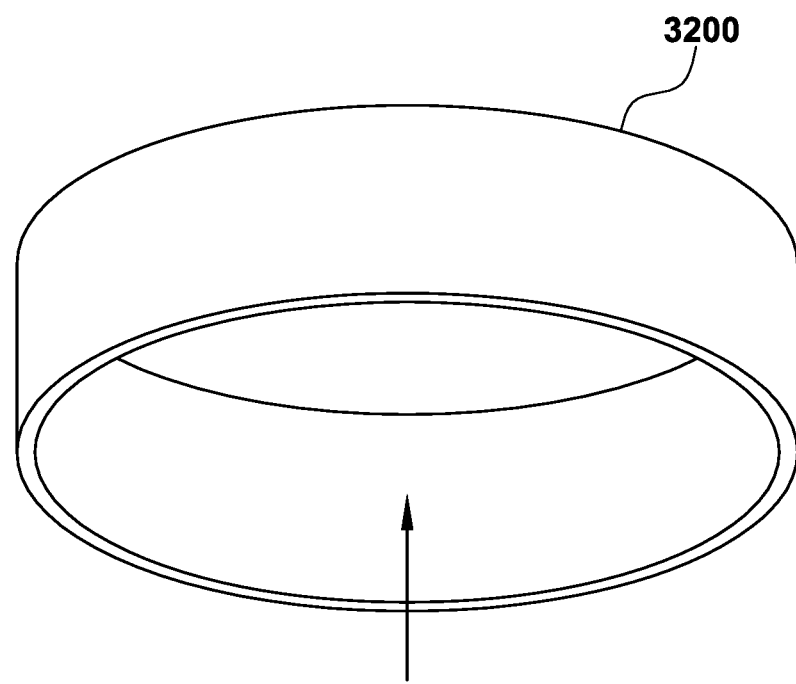
FIG. 32A shows a cap adapted to fit on a standard concrete test cylinder and a sensor device in accordance with an embodiment.
Figure 32B:
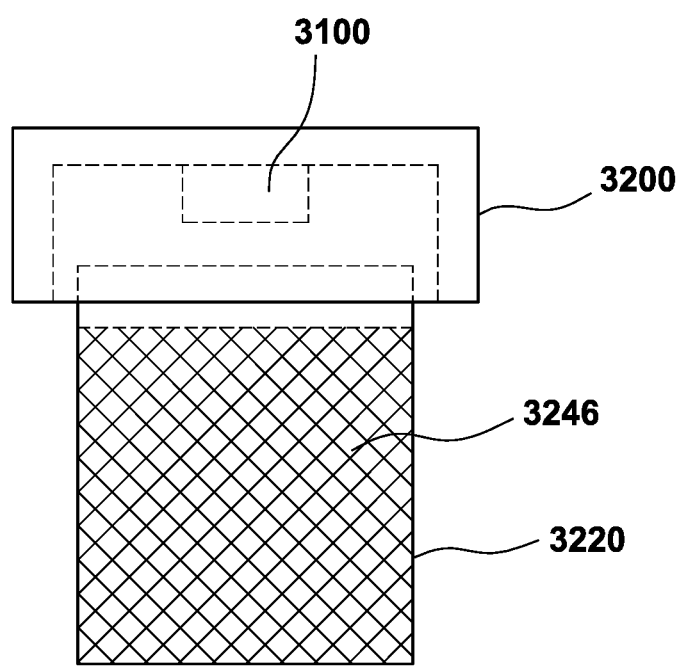
FIG. 32B shows a cap with a sensor device on a standard concrete test cylinder in accordance with an embodiment.

In one embodiment, sensor device 3100 may be attached to an internal surface of a cap adapted to be placed onto a standard test cylinder. FIG. 32A shows a cap and a sensor device in accordance with an embodiment. Cap 3200 is adapted to fit onto the top of a standard concrete test cylinder. Sensor 3100 is attached to an internal surface of cap 3200. Cap 3200 is then placed onto a test cylinder that contains concrete. FIG. 32B shows a cap and a test cylinder in accordance with an embodiment. Sensor device 3100 is attached to the internal surface of the cap 3200. Cap 3200 is fitted onto a test cylinder 3220, which holds a specimen of a concrete mixture 3246. As concrete mixture 3246 dries, sensor device 3100 obtains measurements relating to one or more characteristics of the concrete. For example, sensor device 3100 may obtain data relating to humidity, temperature, etc. Measurement data may be transmitted wirelessly by the sensor device.

Figure 33A:
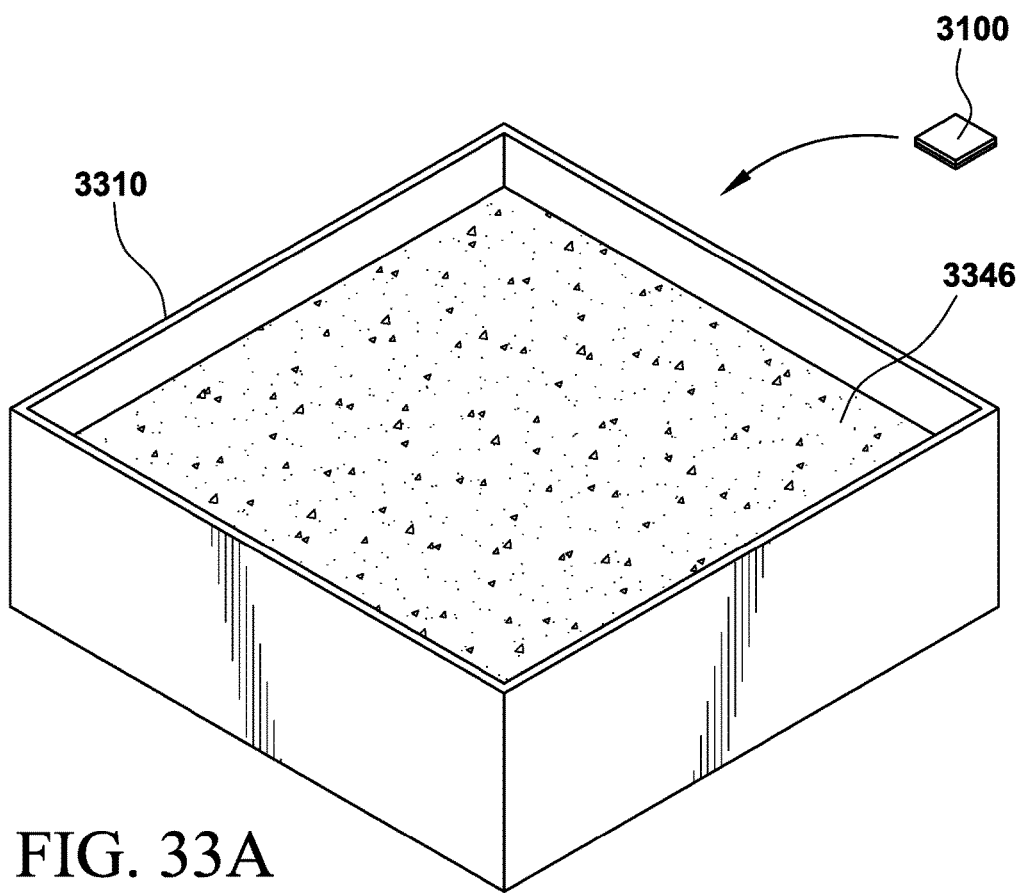
FIG. 33A shows a form containing a concrete mixture and a sensor device in accordance with an embodiment.
Figure 33B:
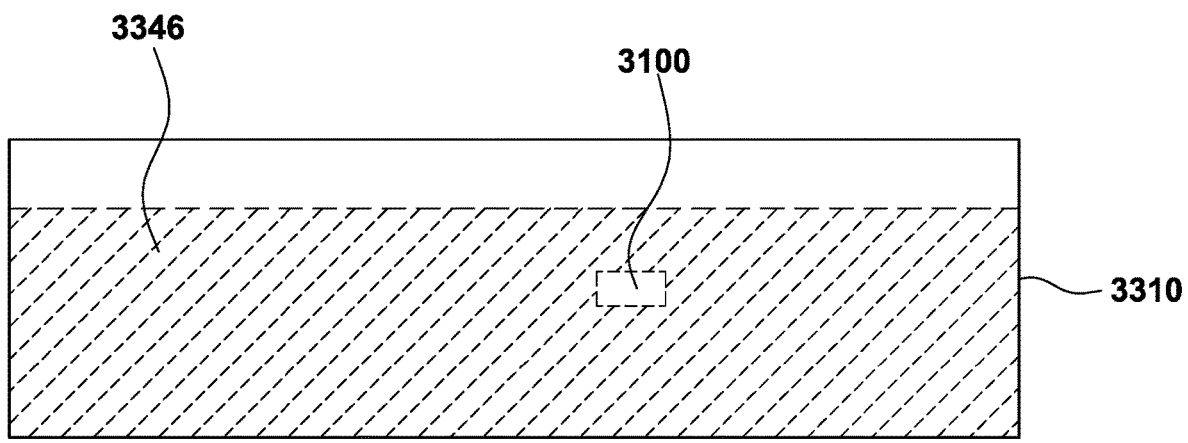
FIG. 33B shows the sensor of FIG. 33A embedded in the concrete mixture within the form of FIG. 33A.

In another embodiment, sensor device 3100 may be inserted into a concrete mixture. FIG. 33A shows a form holding a concrete mixture in accordance with an embodiment. Form 3310 holds a concrete mixture 3346. Sensor device 3100 may be dropped or inserted into concrete mixture 3346. FIG. 33B shows form 3310, concrete mixture 3346, and sensor device 3100 embedded in the concrete mixture in accordance with an embodiment. Sensor device 3100 may obtains measurements relating to one or more characteristics of concrete mixture 3346. Measurement data may be transmitted wirelessly by the sensor device.

In one embodiment, components of a sensor device (such as any of those described herein) may be formed of a thermosetting resin or a thermoplastic.

In one embodiment, a sensor device (such as any of those described herein) may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth ($\frac{3}{16}$) inches.

As mentioned above, in various embodiments, predictions of maturity, strength, and other characteristics may be generated based on measurement data received from one or more sensing devices. Relationships between curing temperature of a concrete mixture and the maturity of the concrete mixture, and between curing temperature of a concrete mixture and the strength of the concrete mixture are well-known. For example, relationships between curing temperature of a concrete mixture and the maturity of the concrete mixture, and between curing temperature of a concrete mixture and the strength of the concrete mixture are discussed in several standards established by ASTM International such as ASTM 1074. Additional examples of relationships between curing temperature and strength and between curing temperature and maturity are found in Burg, Ronald G., "The Influence of Casting and Curing Temperature on The Properties of Fresh and Hardened Concrete," Portland Cement Association: Research and Development Bulletin, ISBN 0-89312-143-6, Skokie, Ill., 1996.

In accordance with another embodiment, a plurality of sensor devices are placed at a plurality of locations at which concrete is to be poured, wherein each sensor device is adapted to measure humidity. For example, the plurality of sensors may be placed at selected locations within a form at a construction site associated with a construction project. Concrete is poured at the plurality of locations. Data representing humidity measurements is received from the plurality of sensor devices. For each of the plurality of sensor devices, a respective spike in humidity and a respective time associated with the spike in humidity are determined, thereby determining a plurality of spikes in humidity and a plurality of corresponding times. A build rate is determined for the construction project based on the plurality of spikes in humidity and a plurality of corresponding times.

Figure 34A:
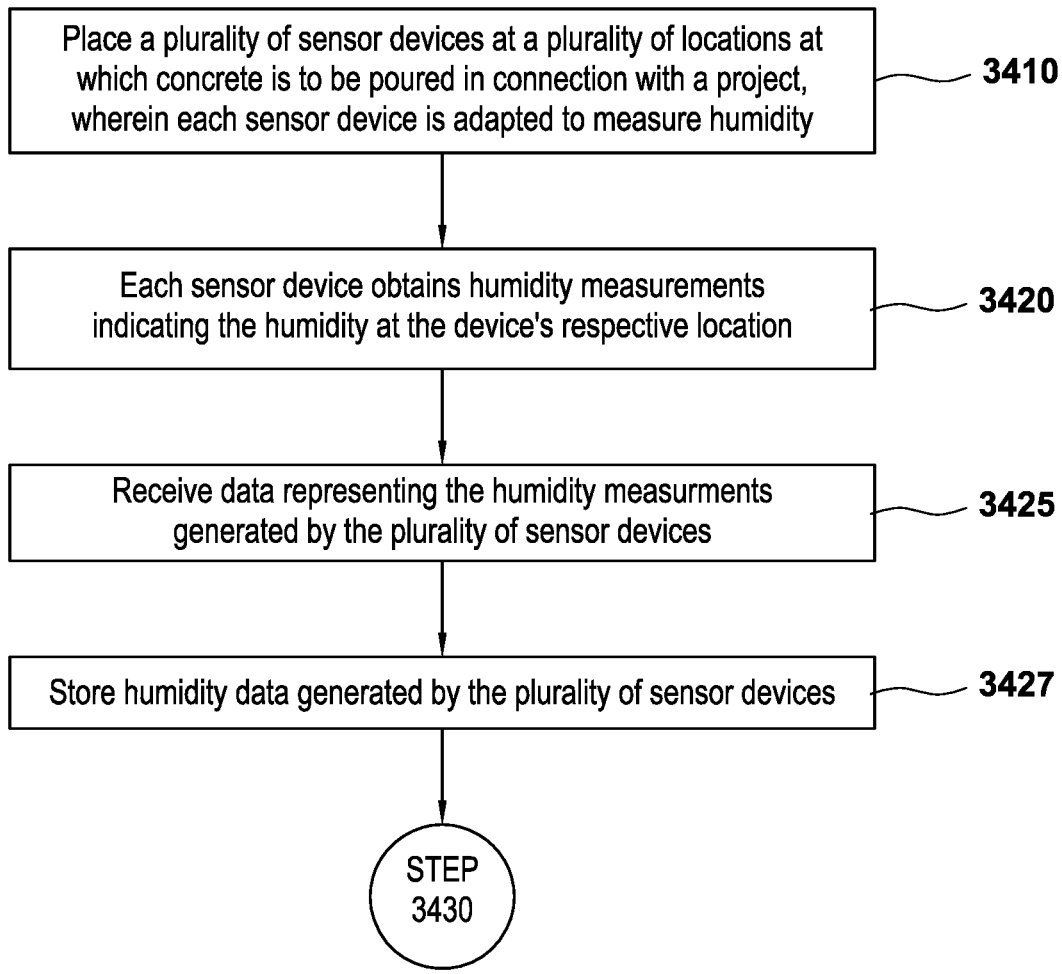
FIGS. 34A-34B include a flowchart of a method of monitoring activity associated with a construction project in accordance with an embodiment.
Figure 34B:
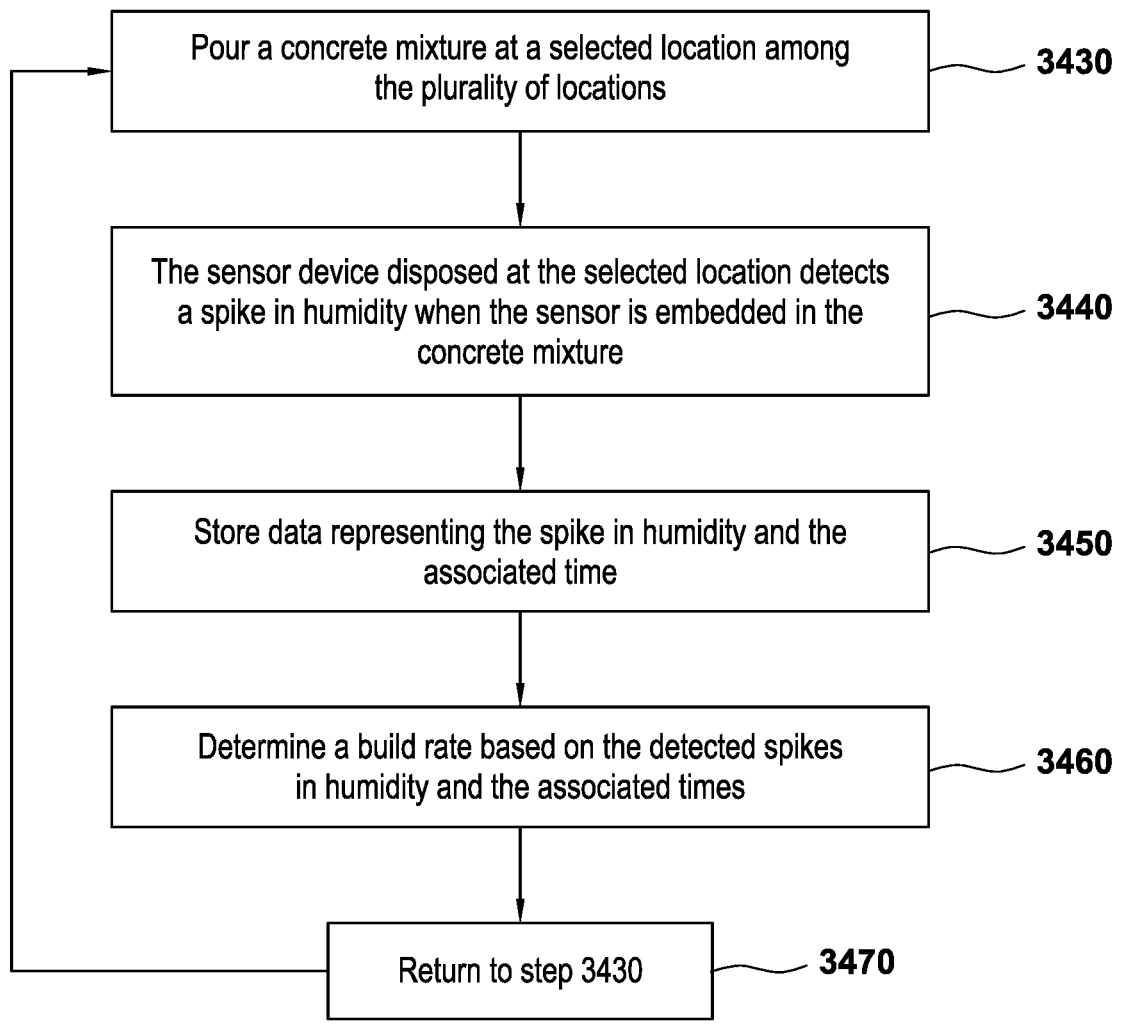
Figure 35:
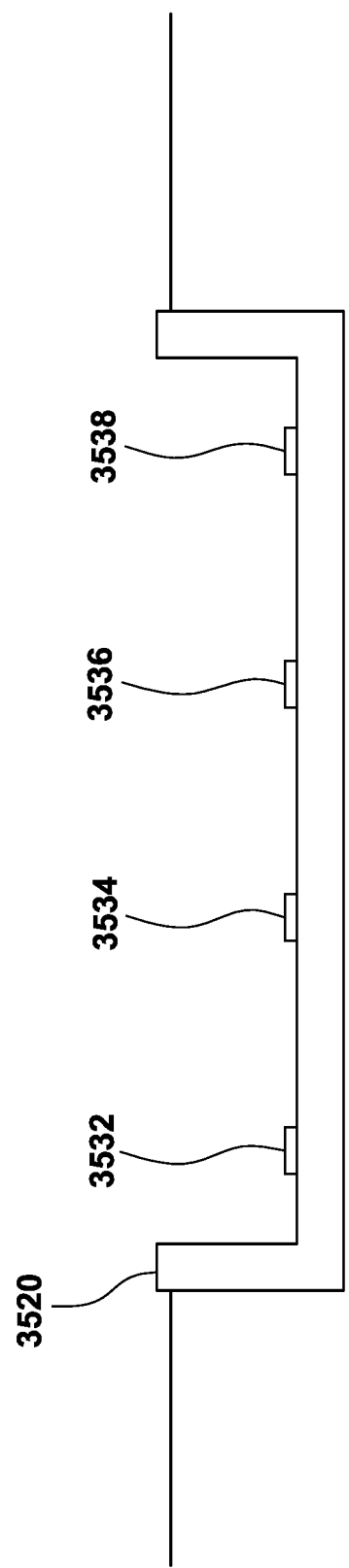
FIG. 35 shows a form and a plurality of sensor devices placed within the form in accordance with an embodiment.

FIGS. 34A-34B include a flowchart of a method of monitoring activity associated with a construction project in accordance with an embodiment. At step 3410, a plurality of sensor devices are placed at a plurality of locations at which concrete is to be poured in connection with a project, wherein each sensor device is adapted to measure humidity. For example, a plurality of sensor devices may be placed at selected locations within a form constructed at a construction site. FIG. 35 shows a form 3520 and a plurality of sensor devices placed within the form in accordance with an embodiment. Sensor devices 3532, 3534, 3536, and 3538 are placed at selected locations with form 3520. For example, each sensor device 3532, 3534, 3536, and 3538 may be a sensor device similar to sensor device 2400 of FIG. 24B. Preferably, the sensor devices are placed in a manner so that each sensor devices is fixed in its location. For example, sensor devices may be attached to a surface of the form or attached to other components within the form.

At step 3420, each sensor device obtains humidity measurements indicating the humidity at the device's respective location. Sensor devices 3532, 3534, 3536, 3538 may be activated immediately and begin to obtain measurements relating to temperature, humidity, and other conditions. Alternatively, each sensor may be partially deactivated when placed in the from and is activated upon detecting predetermined conditions (such as a humidity spike).

At step 3425, data representing the humidity measurements generated by the plurality of sensor devices is received by a processor. Sensor devices 3532, 3534, 3536, 3538 transmit any measurement data obtained. For example, the sensor devices may transmit data wirelessly to a remote processor such as data manager 1935 (shown in FIG. 19). At step 3427, the data generated by the plurality of sensor devices is stored in a memory. For example, data manager 1935 may cause the measurement data to be stored in storage 1970.

Figure 36A:
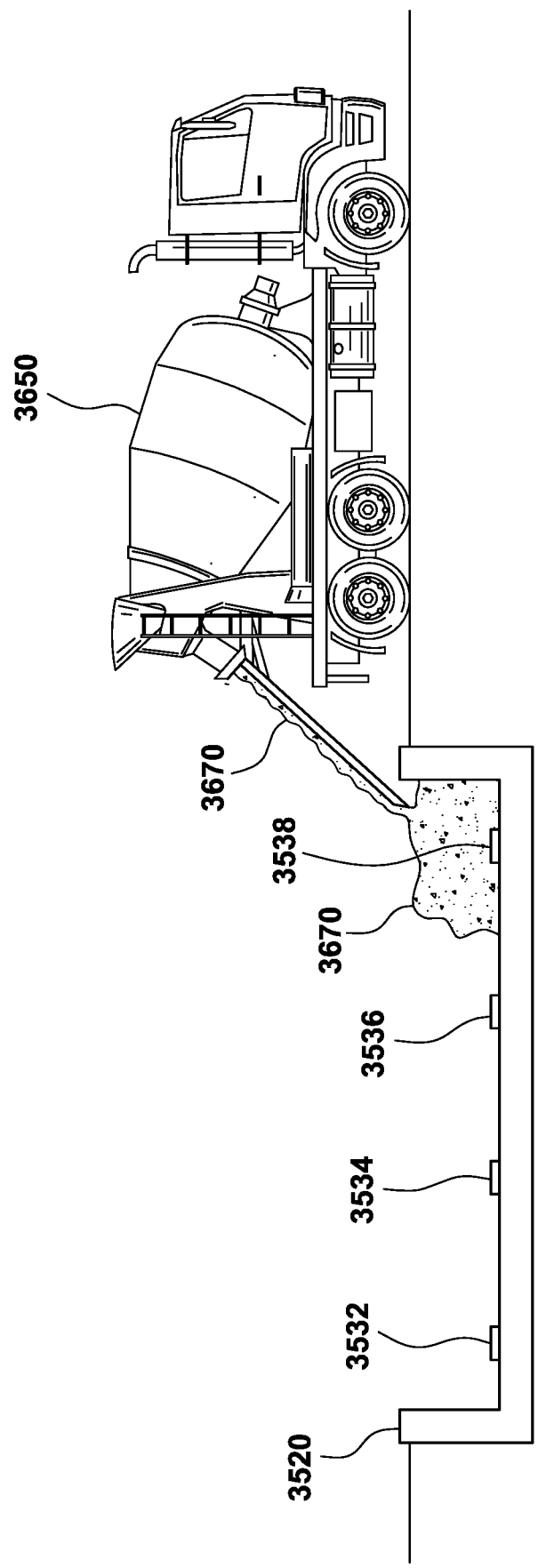
FIGS. 36A-36C shows a concrete mixer truck pouring a concrete mixture into a form at a construction site in accordance with an embodiment.
Figure 36B:
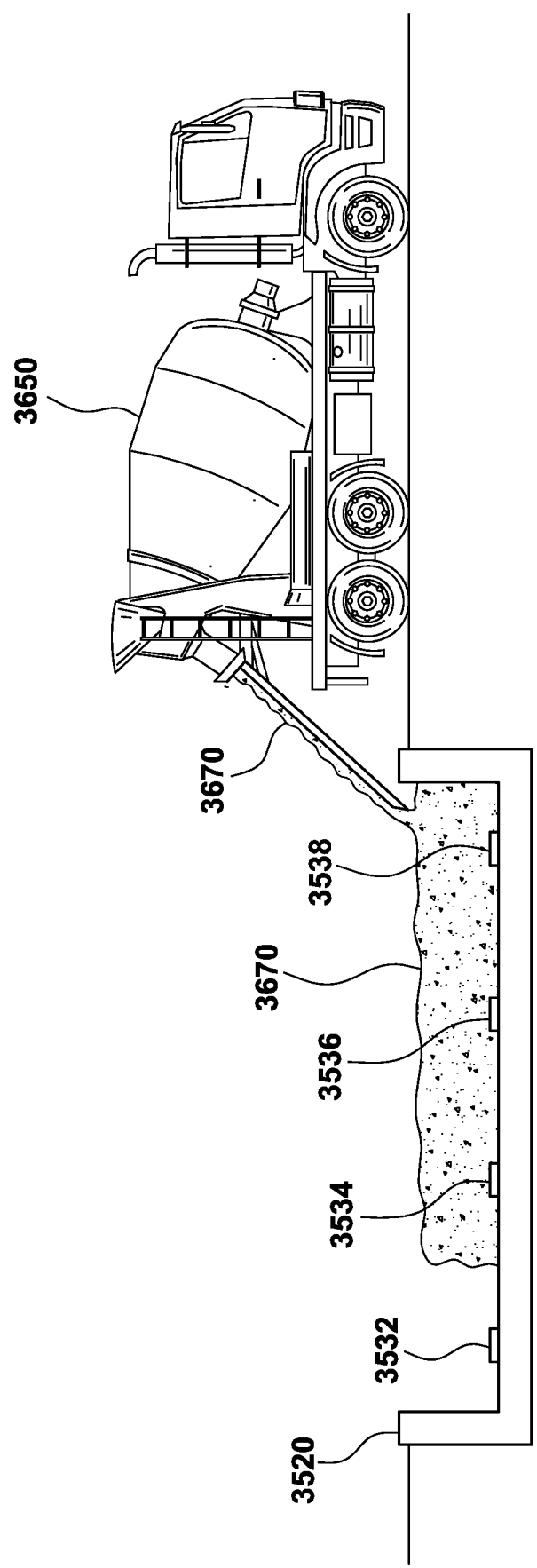
Figure 36C:
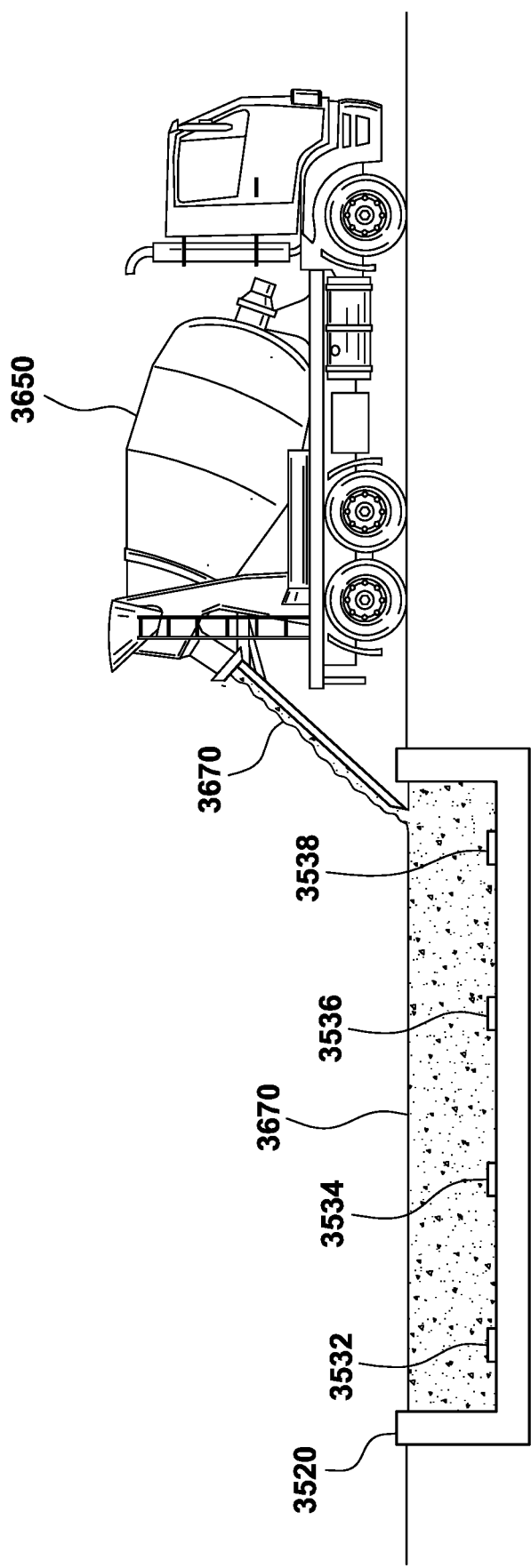

At step 3430, a concrete mixture is poured at a selected location among the plurality of locations. FIGS. 36A-36C show a concrete mixer truck 3650 pouring a concrete mixture 3670 into form 3520 in accordance with an embodiment. In the illustrative embodiment of FIG. 36A, as concrete mixture 3670 is poured into form 3520, the concrete at a first time covers sensor device 3538 but does not cover sensor devices 3536, 3534, or 3532.

At step 3440, the sensor device disposed at the selected location detects a spike in humidity when the sensor is embedded in the concrete mixture. At step 3450, data representing the spike in humidity and the associated time are stored in a memory. At step 3460, the processor determines a build rate based on the recorded spikes in humidity and the associated times. At block 3470, the routine returns to step 3430 and concrete is poured at another selected location.

In the manner described herein, sensor device 3538 detects a spike in humidity after it is covered by concrete mixture 3670. Sensor device 3538 transmits data representing the spike in humidity. For example sensor device 3538 may transmit the data wirelessly. Data manager 1935 receives the data and stores the data representing the humidity spike in storage 1970. Data manager 1935 also stores data indicating the time when the humidity spike was detected by sensor device 3538.

Referring to FIGS. 36B and 36C, as the concrete mixture 3670 is poured into form 3520, the concrete mixture progressively covers sensor devices 3538, 3536, 3534, and 3532. Referring to FIG. 36B, at a second time concrete mixture 3670 covers sensor devices 3538, 3536, and 3534, but does not cover sensor device 3532. Referring to FIG. 36C, at a third time concrete mixture 3670 covers sensor devices 3538, 3536, and 3534, and 3532. As each sensor device is covered by concrete mixture 3670, the sensor device detects a humidity spike and transmits data representing the humidity spike to data manager 1935. Data manager 1935 stores the data representing the various humidity spikes detected by sensor devices 3538, 3536, 3534, and 3532.

After data indicating spikes in humidity is received from multiple sensor devices, data manager 1935 determines a build rate based on the data received from the sensor devices. In particular, after data indicated detection of a humidity spike is received from each sensor device 3538, 3536, 3534, and 3532, data manager 1935 may determine a build rate indicating the rate at which concrete is being poured within frame 3520.

Figure 37:
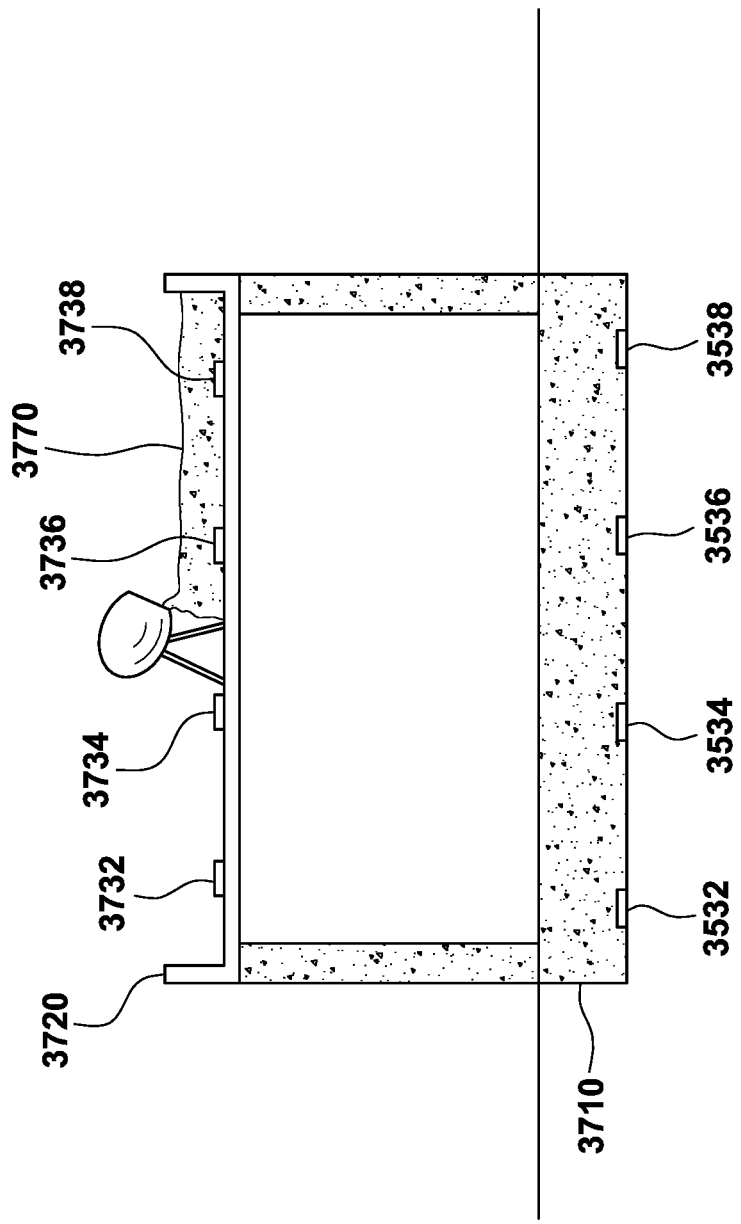
FIG. 37 shows a structure that is under construction in accordance with an embodiment.

The method of determining a build rate may be used for a structure of any size and shape, or for multiple structures being constructed at a construction site or at multiple sites during a construction project. FIG. 37 shows a structure that is under construction in accordance with an embodiment. A completed first level 3710 corresponds to the structure built using form 3520 shown in FIGS. 35 and 36A-36C. First level 3710 includes sensor devices 3532, 3534, 3536, and 3538. A second form 3720 is constructed on a second level. Sensor devices 3732, 3734, 3736, and 3738 are placed at selected locations within form 3720. A concrete mixture 3770 is poured into form 3720 to form a second level of the structure.

In a manner similar to that described above, sensor devices 3732, 3734, 3736, 3738 detect respective spikes in humidity as they are embedded in the concrete mixture 3770. The measurement data is transmitted wirelessly, and data manager 1935 determines a build rate for the second level of the structure based on the data received from the sensor devices.

Figure 38A:
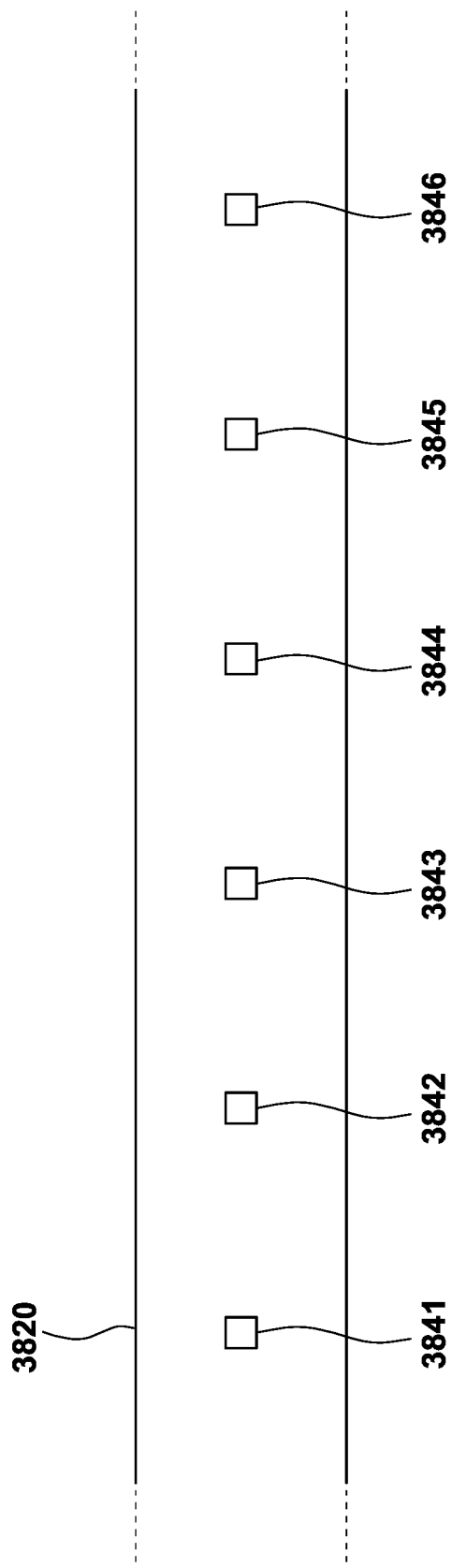
FIG. 38A shows a road under construction in accordance with an embodiment.
Figure 38B:
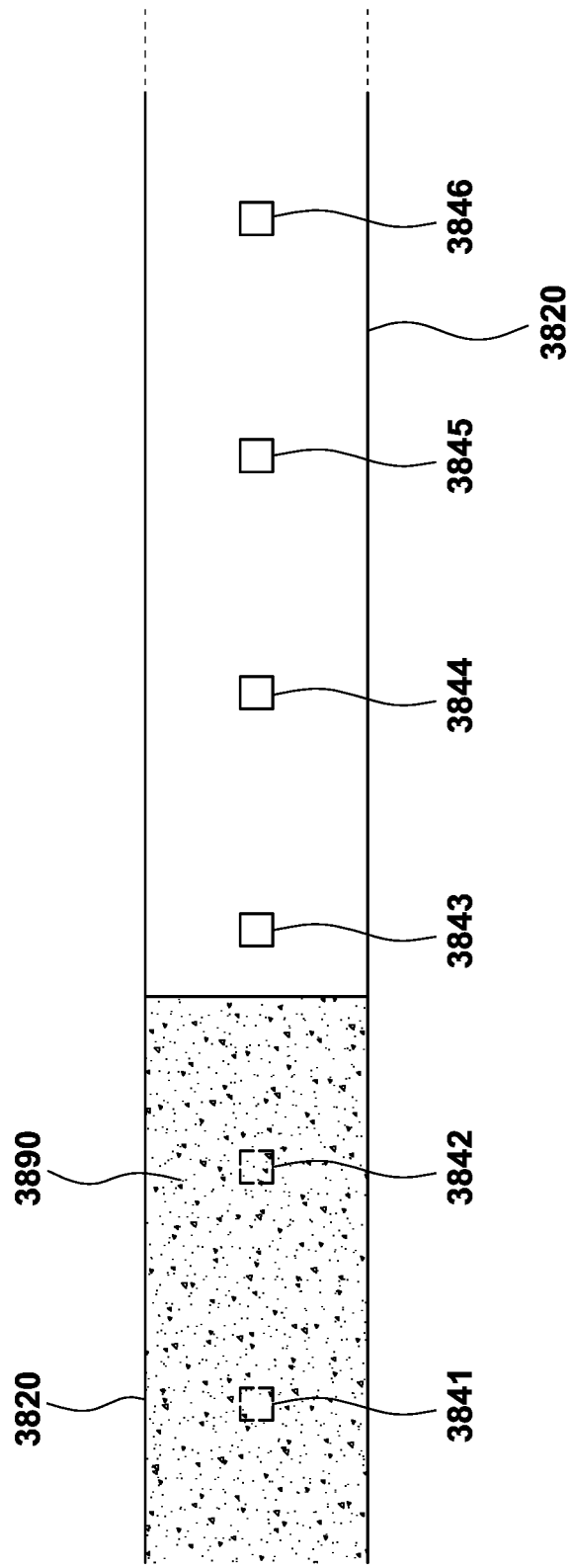
FIG. 38B shows the roadway of FIG. 38A after concrete has been poured on a portion of the roadway.

Devices, systems, and methods described herein may also used in larger projects that are not limited to one or more construction sites. FIG. 38A shows a road under construction in accordance with an embodiment. After a roadway 3830 is defined, a plurality of sensor devices 3841, 3842, 3843, 3844, 3845, 3846, etc. are placed at selected locations on the roadway. Concrete or another material (e.g., asphalt) is poured to form the roadway. FIG. 38B shows the roadway of FIG. 38A after concrete has been poured on a portion of the roadway in accordance with an embodiment. In the illustrative embodiment of FIG. 38B, a concrete mixture 3890 has been poured onto a section of roadway 3820. As a result, sensor devices 3841 and 3842 are embedded in the concrete mixture. Sensor devices 3843, 3844, 3845, 3846 are not embedded in the concrete mixture.

In a manner similar to that described above, sensor devices 3841, 3842, 3843, 3844, 3845, and 3846 detect respective spikes in humidity as they are embedded in the concrete mixture 3890. The measurement data is transmitted wirelessly, and data manager 1935 determines a build rate for the roadway project based on the data received from the sensor devices.

In accordance with another embodiment, a build rate is determined based on the humidity spike data. A build rate indicating a rate at which a concrete mixture is poured over a linear distance may be determined. For example, data manager 1935 may determine a distance between first and second sensor devices at a particular construction site, determine a time between the humidity spikes detected by the first and second sensor devices, and determine a build rate equal to the distance between sensor devices divided by the time between humidity spikes. Alternatively, a build rate indicating other types of information, such as levels of a structure per unit time, may be determined.

In other embodiments, a build rate may be determined based on the humidity spike data and other data received from sensor devices. For example, each sensor device embedded in a structure may include a motion sensor and/or an accelerometer, and a location sensor having GPS capability. Therefore, each sensor device may generate motion data and/or acceleration data, and location data allowing the location of the sensor device to be determined. The motion data and/or acceleration data and the location data is transmitted to data manager 1935 and stored. Data manager 1935 may subsequently analyze the motion and acceleration data to identify patterns of motion and acceleration that are associated with formwork stripping (removal of a form). Accordingly, data manager 1935 may determine when a form (such as form 3520) is removed at a particular location. Data manager 1935 may combine the formwork removal information with the humidity spike data received from sensor devices at a construction site (or associated with a project) to determine a build rate representing when components of the structure are completed (concrete poured and formwork removed).

In accordance with an embodiment, one or more activities may be performed or adjusted based on a build rate determined in the manner described above. Alternatively, a schedule determining when an activity is performed may be adjusted based on a build rate. For example, a schedule for pouring concrete may be adjusted based on a build rate. For example, the components of a concrete mixture used may be adjusted based on a build rate. For example, a schedule for removal of forms may be adjusted based on a build rate. For example, a schedule for ordering components may be adjusted based on a build rate.

In accordance with an embodiment, data relating to a structure's status, or a construction project's status, may be provided to a user in graphical form. For example, data manager 1935 may receive and store data from various sensor devices within various structures located at one or more construction projects and store the data. The data may include data such as measurements of various conditions such as temperature, humidity, motion, acceleration, etc. The data may also include location data obtained using GPS functionality. Data manager 1935 may analyze the data to determine a variety of information and characteristics such as humidity spikes representing when a sensor device has been embedded in a concrete mixture, the strength, maturity, etc., of the concrete mixture, if form have been removed from a structure or from a portion of a structure, etc. Any of such information may be provided to a user in graphical form. Data manager may transmit selected information to a user device and cause the user device to present the information in a selected format. The information may be presented to a user in real-time, or near real-time, by continually updating the information displayed on the user device.

Figure 39:
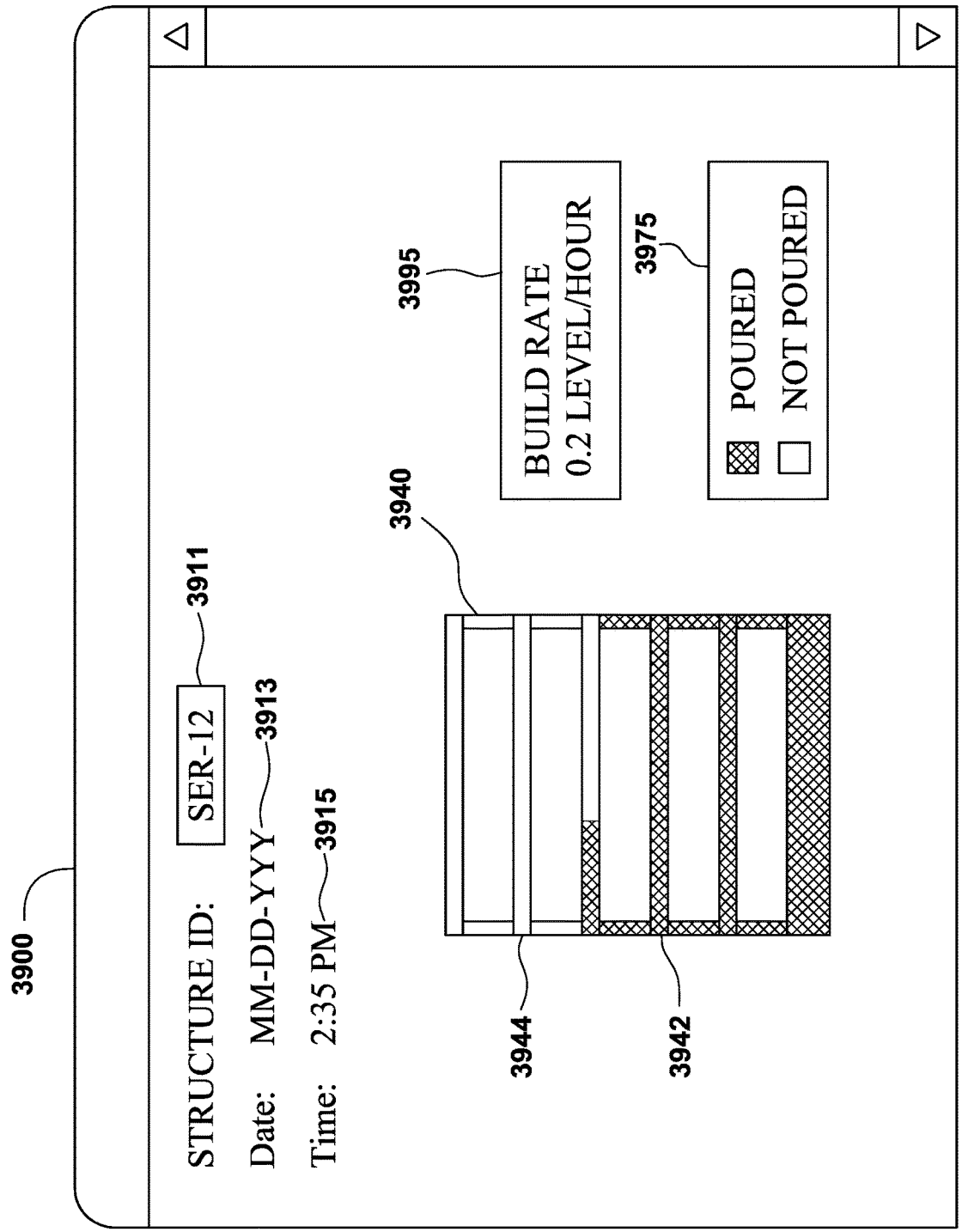
FIG. 39 shows a page showing a plan of a structure that may be displayed on a user device in accordance with an embodiment.

For example, FIG. 39 shows a page showing a plan of a structure that may be displayed on a user device in accordance with an embodiment. Page 3900 includes a structure identifier line 3911 that allows a user to enter information identifying a selected structure. In the illustrative embodiment, a user has entered the identifier "SER-12." Page 3900 also includes a date line 3913, and a time line 3915. Accordingly, a user may view page 3900 to view real-time (or near real-time) information concerning the status of a desired structure.

In the illustrative embodiment, page 3900 shows a plan 3940 of a structure associated with the identifier "SER-12." In accordance with a key 3975 displayed on page 3900, portions of the structure for which concrete has been poured are displayed in a dark color (e.g., black or shaded) while portions of the structure for which concrete has not yet been poured are rendered in a light color (e.g., white). In the illustrative embodiment, the plan 3940 illustrated on page 3900 indicates that concrete has been poured for three levels and for a portion of a fourth level of the structure; however, concrete has not yet been poured for a fifth level and a sixth level.

Page 3900 includes a box 3995 indicating that the build rate for the structure is currently 0.2 levels per hour. Build rates may be displayed in other formats.

Figure 40:
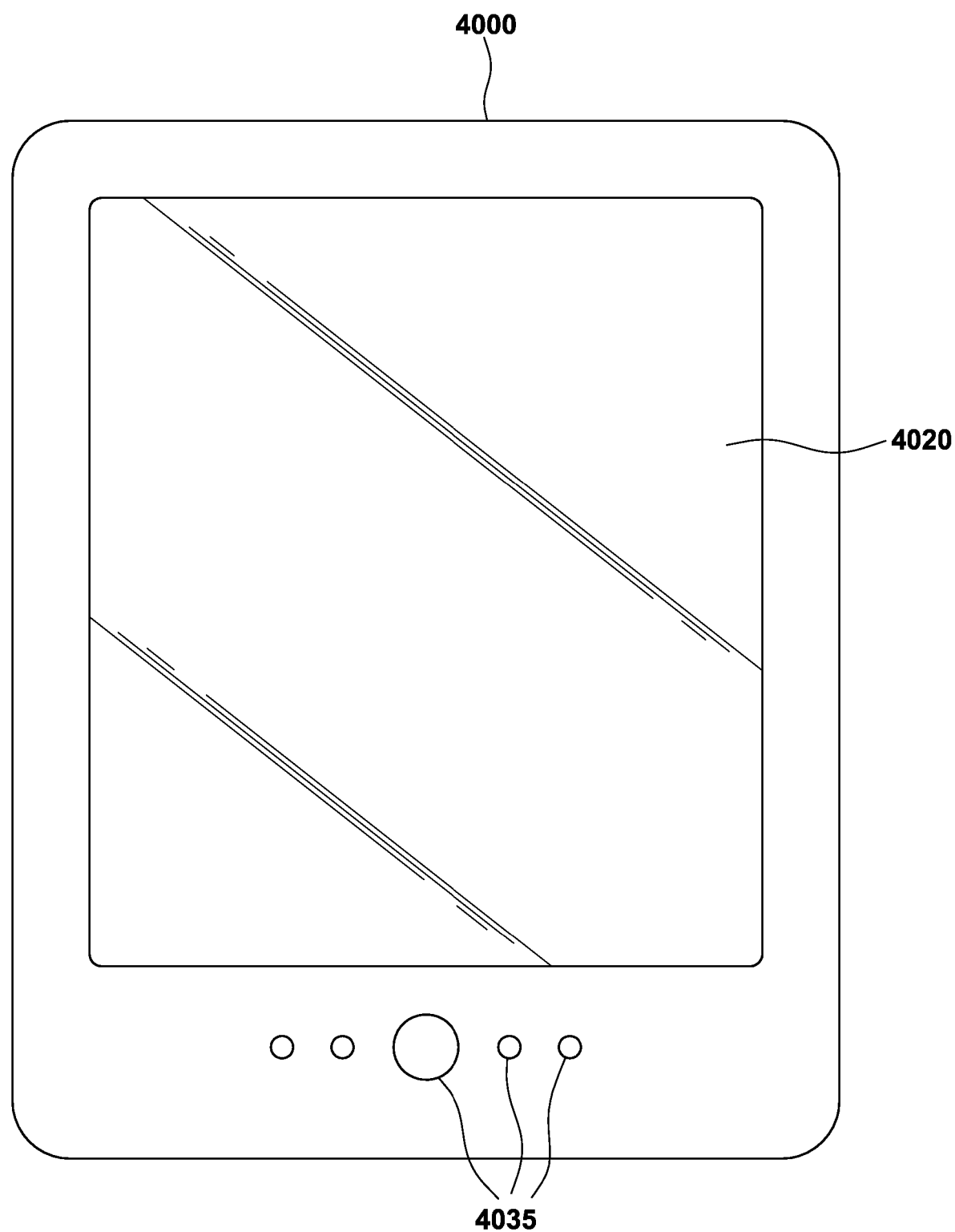
FIG. 40 shows a user device in accordance with an embodiment.

Information related to data generated by sensor devices, such as the information shown on page 3900, may be displayed on any type of user device. FIG. 40 shows a user device in accordance with an embodiment. User device 4000 includes a display device 4020 (e.g., a screen) and several buttons 4035. User device 4000 may be a cell phone, a tablet device, a laptop device, etc. Other types of user devices, such as personal computers, server computers, etc., may be used.

Figure 41:
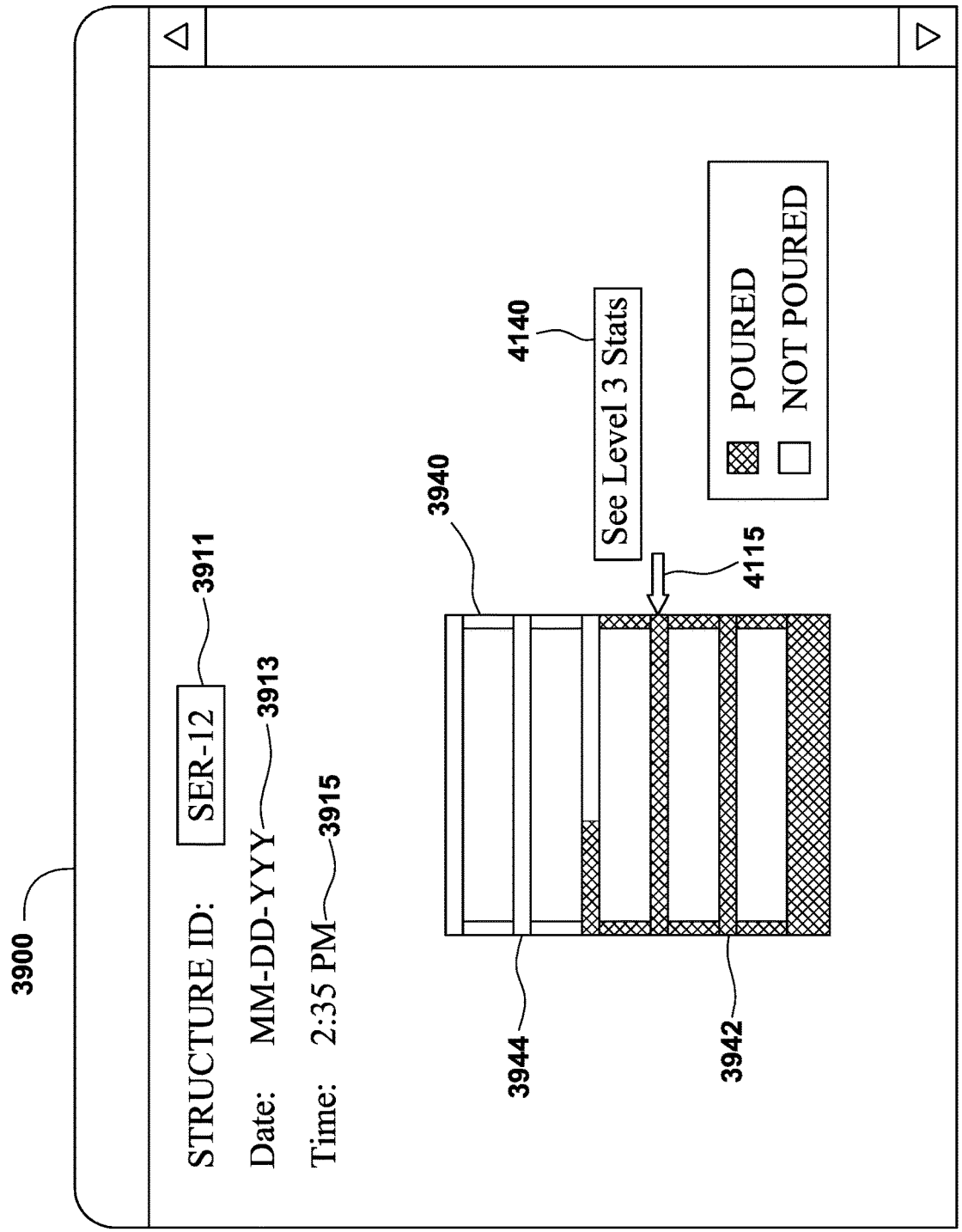
FIG. 41 shows the page of the embodiment of FIG. 39 with an option to view additional information relating to the structure displayed.

In accordance with another embodiment, information relating to one or more selected components of a structure is provided to a user. FIG. 41 shows page 3900 of the embodiment FIG. 39 with an option to view additional information relating to the structure displayed. A user may select a particular component of structure 3940 and obtain additional information about the component. In the illustrative embodiment, the user moves a cursor 4115 to indicate the third level of the structure. In response, the user device causes a "See Level 3 Stats" option 4140 to be displayed.

When the user selects option 4140, a page such as that shown in FIG. 42 is displayed. FIG. 42 shows a page 4200 displaying information relating to a selected portion or component of a structure in accordance with an embodiment. In particular, page 4200 includes a structure identifier line 4111, which indicates that the information on the page pertains to the structure identified as "SER-12." Page 4200 also includes a component line 4113, which indicates that "Level 3" has been selected. Page 4200 includes a strength line 4221, indicating that the selected component has a Strength of 5000 PSI. Page 4200 includes a "Time Used" line 4222, which indicates that 80 hours were used to complete Level 3, a "Cost of Component" line 4223, which indicates the cost of completing the selected component, and a "Cost of Structure (Cumulative)" line 4224, indicating the cumulative cost of building the structure up to and including the completion of the selected component. Page 4200 also includes a "Build Rate" line 4225 indicating that the build rate for Level 3 of the structure is currently six (6) feet per hour. Other items of information relating to the selected component may be included. Page 4200 also includes a "Back" button 4255 which allows the user to return to page 3900.

Figure 43:
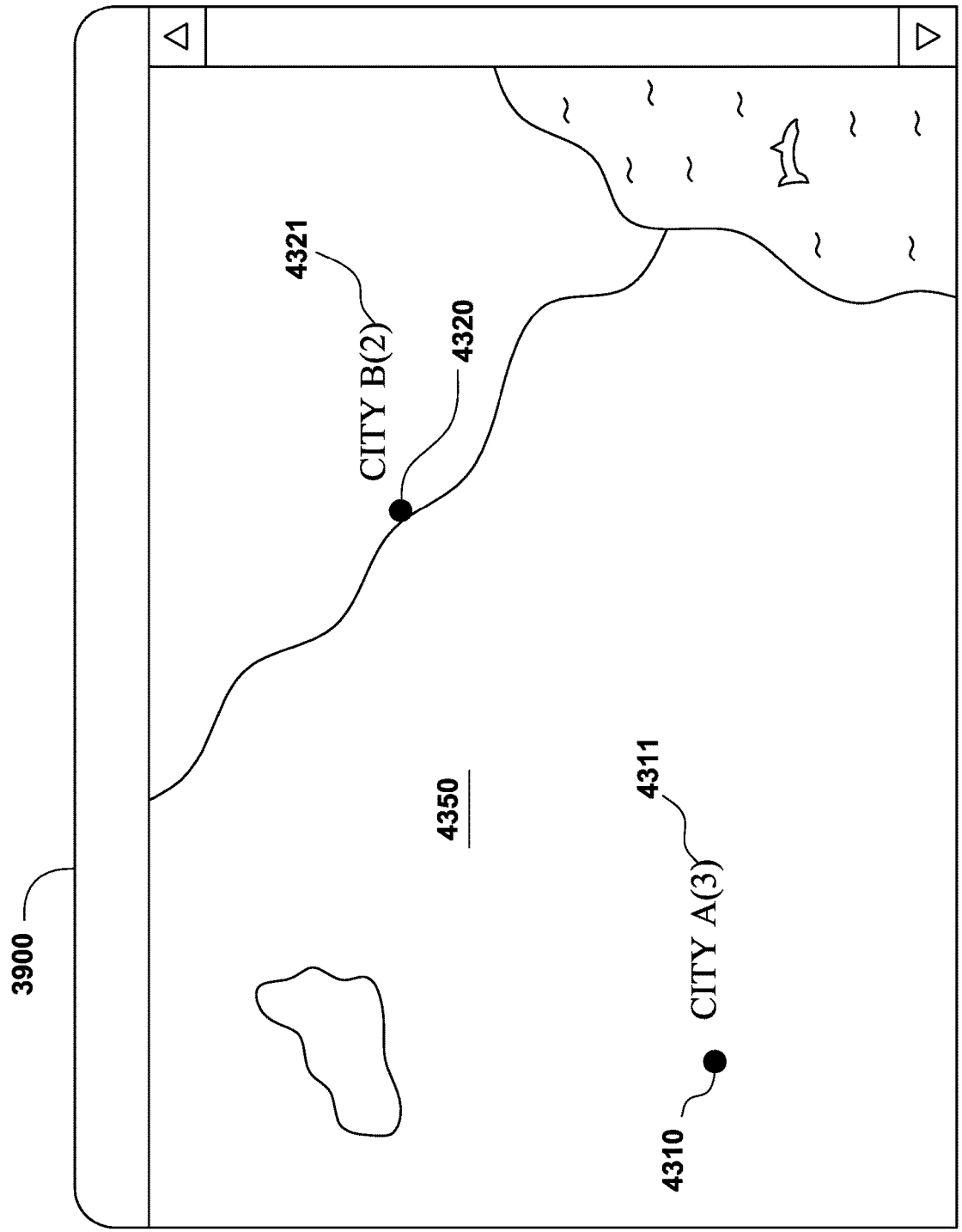
FIG. 43 shows a page showing a region in accordance with an embodiment.

In accordance with another embodiment, a user may employ a user device to view one or more construction sites at various levels of detail. For example, a user may view a map showing the locations of construction projects managed by a particular company within a selected region. FIG. 43 shows a page 4300 showing a region in accordance with an embodiment. Specifically, page 4300 shows a region 4350 that includes a City A 4310 and a City B 4320. Each city is labelled with its name and a number representing a number of active construction projects located in the city. Thus, the label for City A includes the number "3" (4311) indicating that three active construction projects are located in City A. Similarly, the label for City B includes the number "2" (4321) indicating that two active construction projects are located in City B.

Figure 44:
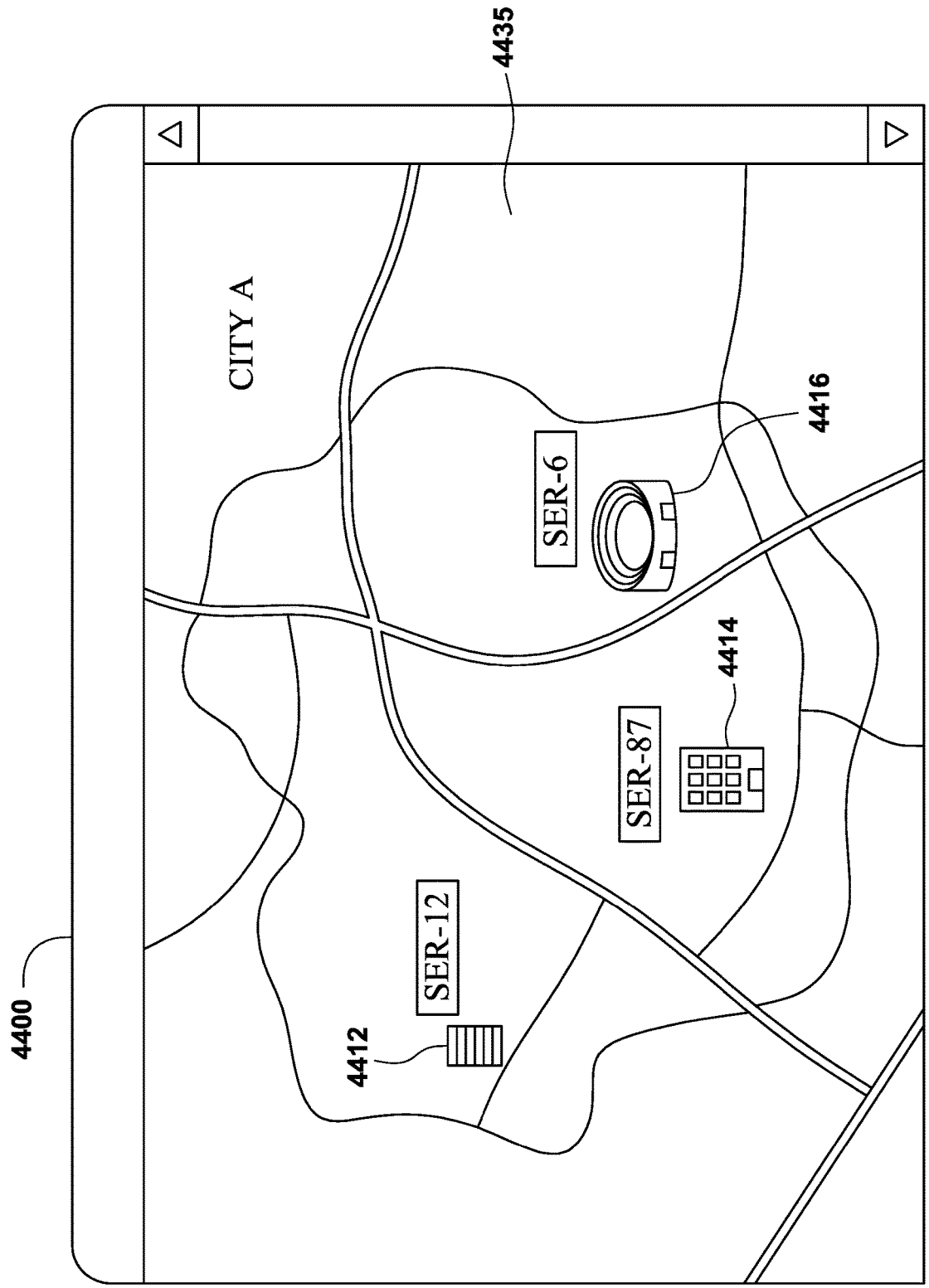
FIG. 44 shows a map of a city in accordance with an embodiment.

The user may use a zoom function to view a portion of the region in greater detail. In the illustrative embodiment, suppose that the user selects City A, for example, by selecting City A with a cursor, by clicking a button on a mouse, or in another manner. In response, the user device may display a "zoomed" image of City A. FIG. 44 shows a map 4435 of City A in accordance with an embodiment. Map 4435 includes graphical indicators representing three construction projects located in City A. Specifically, map 4435 shows graphical indicators 4412, 4414, 4416 representing, respectively, the construction project identified as "SER-12," a construction project identified as "SER-87," and a construction project identified as "SER-6."

Figure 45:
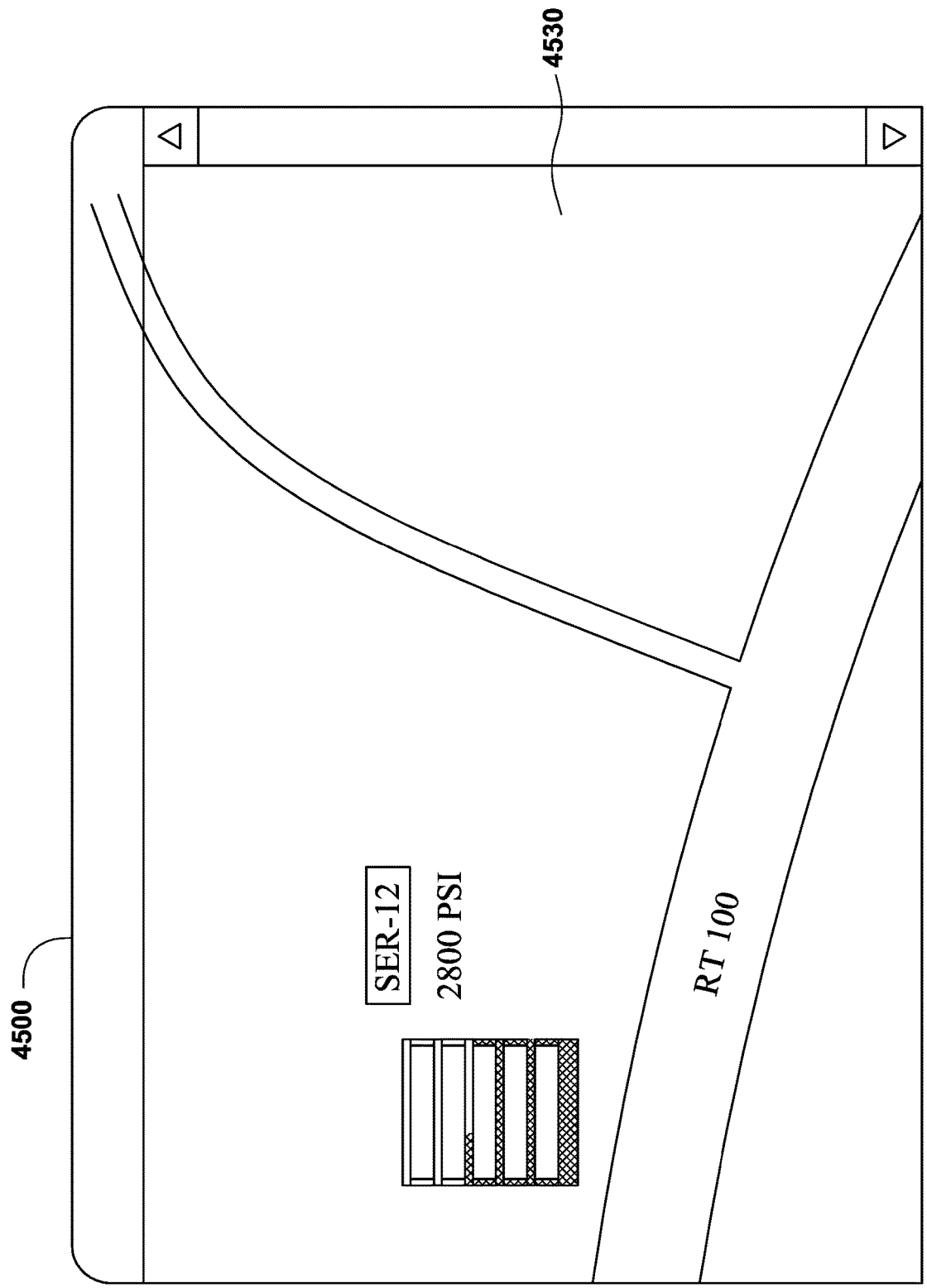
FIG. 45 shows a page that includes a map showing the location of a selected construction project in accordance with an embodiment.

The user may use the zoom feature to obtain additional images and maps showing a particular construction project in greater detail. For example, a user may select a particular construction project shown in map 4435 (on page 4400), for example, by selecting the location with a cursor, by clicking a button, on a mouse, or in another manner, to obtain a map of the selected construction project. FIG. 45 shows a page 4500 that includes a map showing the location of the construction project identified as "SER-12" in accordance with an embodiment.

Figure 46:
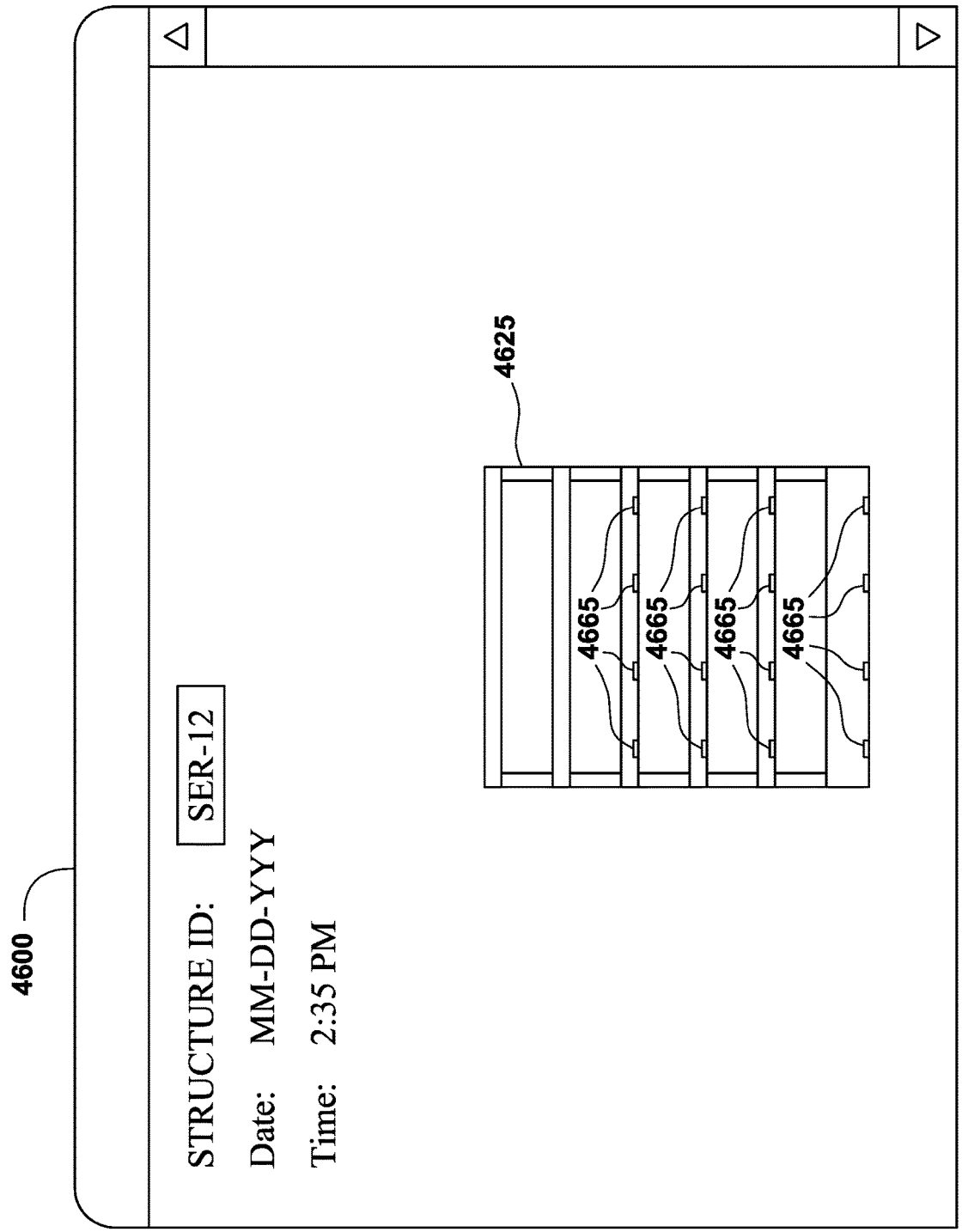
FIG. 46 shows a page showing a plan of a structure in accordance with an embodiment.

In accordance with an embodiment, a user may use the zoom feature to obtain an image of a particular structure at a selected construction project. A user device may display the locations of individual sensor devices within a selected structure. FIG. 46 shows a page showing a plan 4625 of the structure identified as "SER-12" in accordance with an embodiment. FIG. 46 also shows locations of a plurality of sensor devices 4665 that have been placed within the structure.

Figure 47:
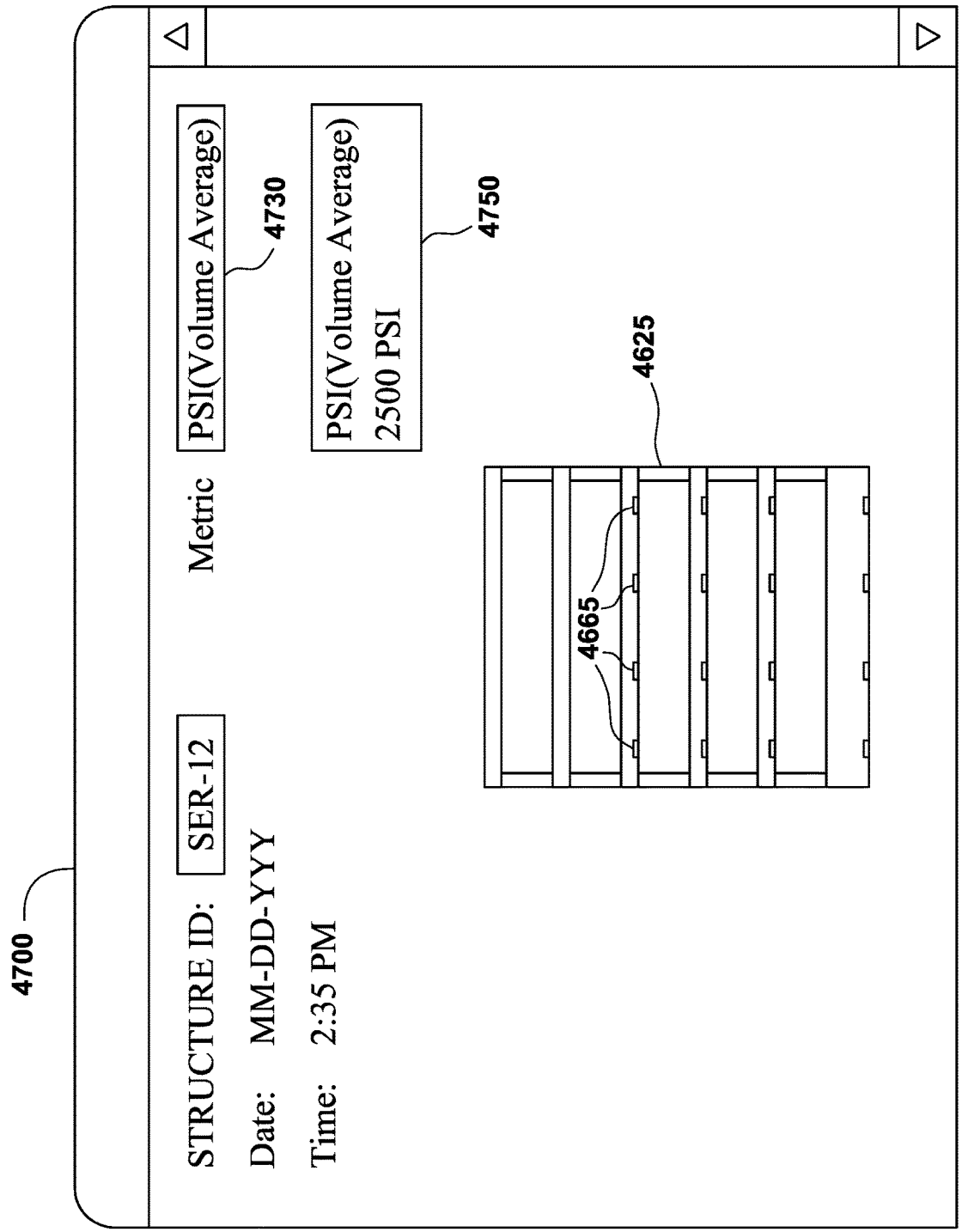
FIG. 47 shows a page showing a plan of a structure and additional information relating to the structure in accordance with an embodiment.

In accordance with another embodiment, a user may view a selected metric for a single component of a structure, or a volume averaged value of a selected metric for a single component of a structure, for the entire structure, for a plurality of structures zai a construction site, for a plurality of construction projects within a city or region, or for a plurality of construction projects within a country. FIG. 47 shows a page 4700 showing plan 4625 of a structure associated with the identifier "SER-12." Page 4700 includes a field 4730 that allows a user to select a desired metric. In the illustrative embodiment, the user selects "PSI (Volume Agerage)." Accordingly, a box 4750 is displayed on page 4700 indicating that the current volume average PSI value for the structure associated with plan 4625 is 2500 PSI. The volume average value is current and may change as additional levels of the structure are completed.

Figure 48:
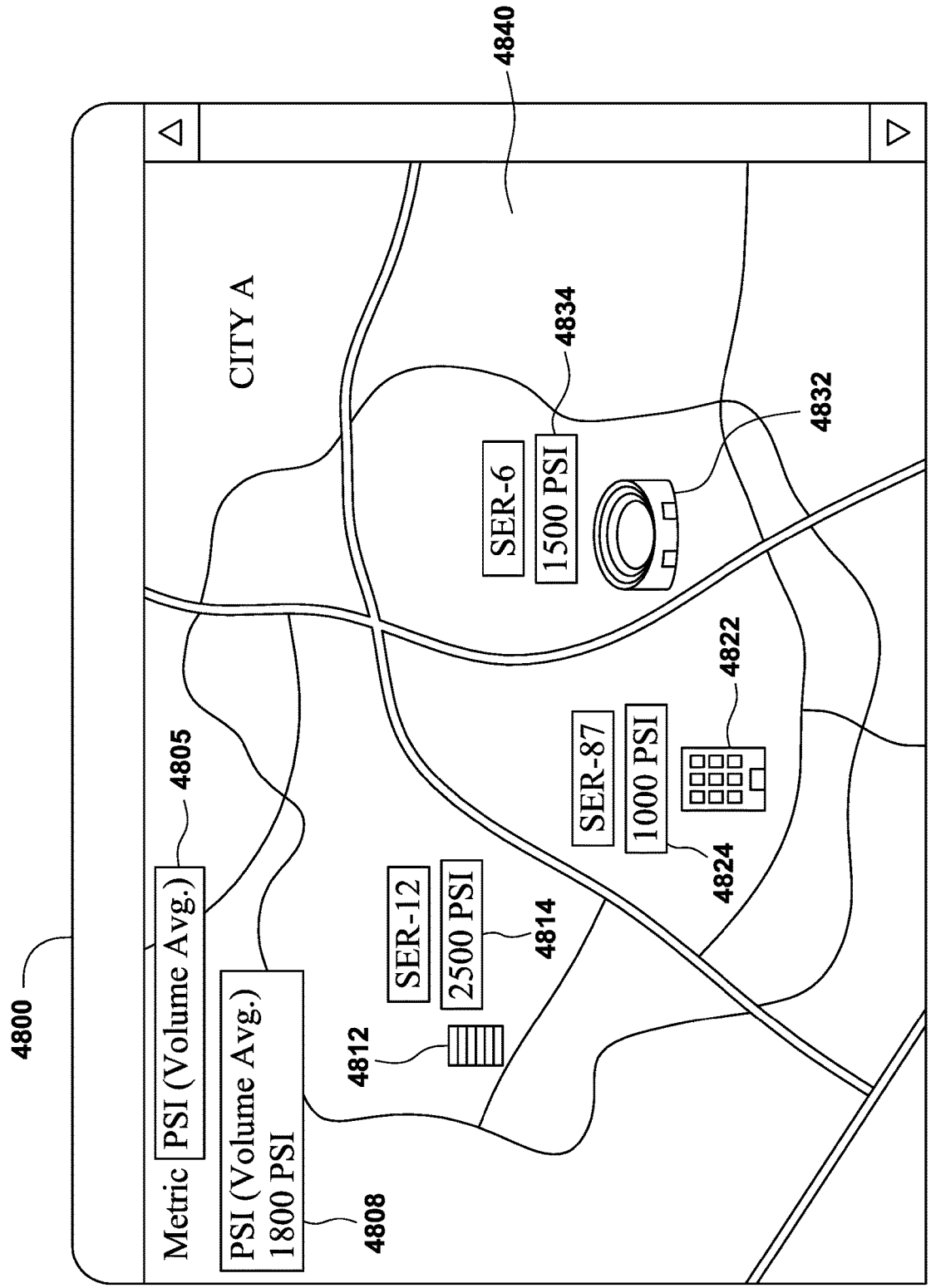
FIG. 48 shows a page displaying a map of a city and statistics related to construction projects within the city in accordance with an embodiment.

FIG. 48 shows a page 4800 displaying a map of a city and statistics related to construction projects within the city in accordance with an embodiment. Page 4800 includes a field 4805 that allows a user to select a desired metric to be displayed. In the illustrative embodiment, the user has selected PSI (Volume Average). Accordingly, a box 4808 specifying that the volume average PSI value for all construction projects within City A is 1800 PSI is displayed. Additionally, volume average PSI information is displayed for several construction projects within City A. Specifically, map 4840 includes a graphical indicator 4812 representing the construction project identified as "SER-12" and a statistic 4814 indicating that the current volume average PSI for the construction project is 2500 PSI. Map 4840 also includes a graphical indicator 4824 representing the construction project identified as "SER-87" and a statistic 4824 indicating that the current volume average PSI for the construction project is 1000 PSI. Map 4840 further includes a graphical indicator 4832 representing the construction project identified as "SER-6" and a statistic 4834 indicating that the current volume average PSI for the construction project is 1500 PSI.

Figure 49:
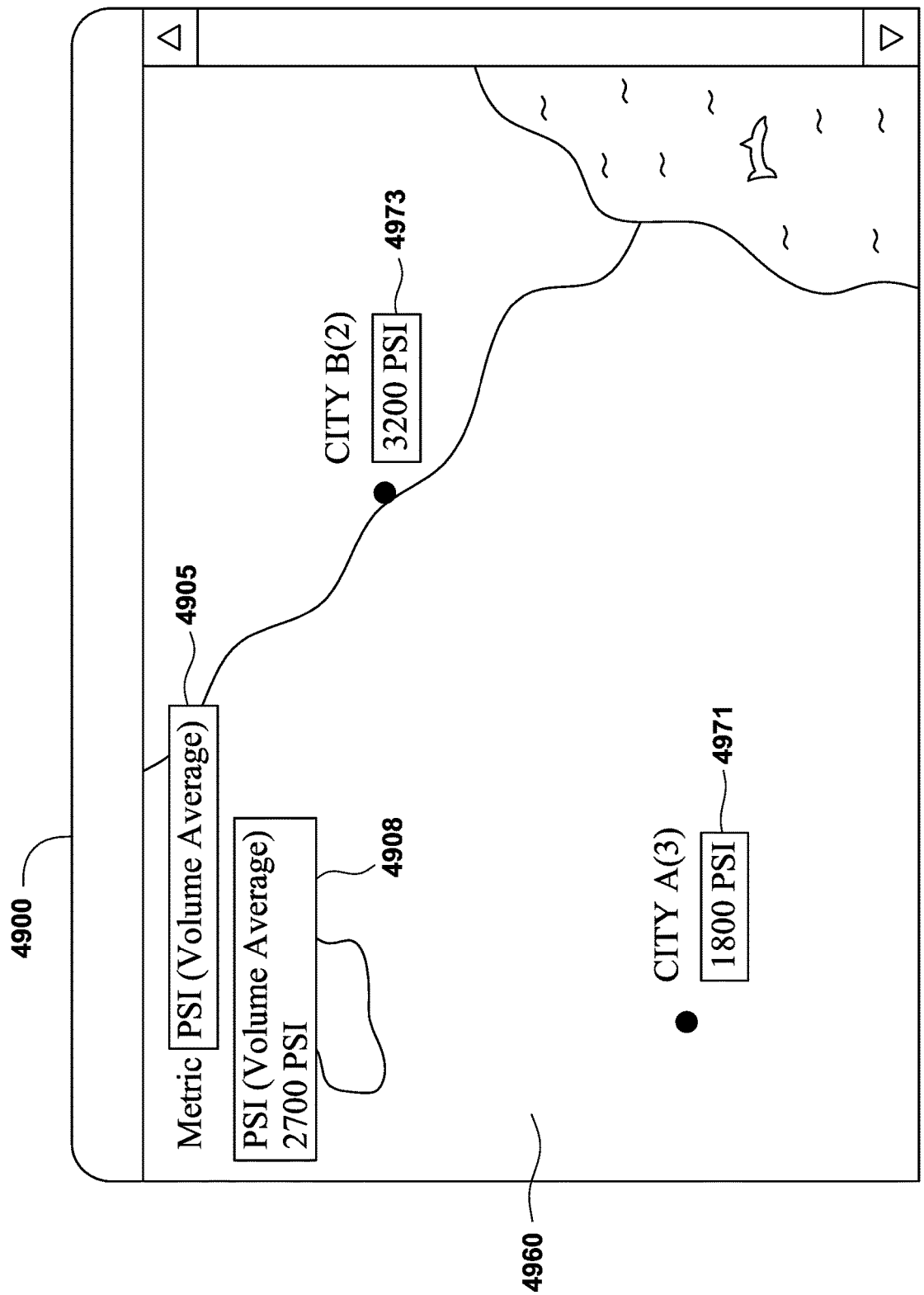
FIG. 49 shows a page displaying a map of a selected region and selected information associated with construction projects in the region in accordance with an embodiment.

A user may zoom in or out to view information at different levels of resolution. For example, a user may view a selected metric for a selected region. FIG. 49 shows a page 4900 displaying a map 4960 of a selected region and selected information associated with construction projects in the region in accordance with an embodiment. Specifically, FIG. 49 shows a region that includes City A and City B. Page 4900 includes a field 4905 that allows a user to select a desired metric to be displayed. In the illustrative embodiment, the user has selected PSI (Volume Average). Accordingly, a box 4908 specifying that the volume average PSI value for construction projects within the selected region is 2700 PSI is displayed. Page 4900 also displays a statistic 4971 proximate the location of City A on map 4960 indicating that the volume average PSI value for construction projects within City A is 1800 PSI, and a statistic 4973 proximate the location of City B on the map indicating that the volume average PSI value for construction projects within City B is 4973 PSI.

Figure 50:
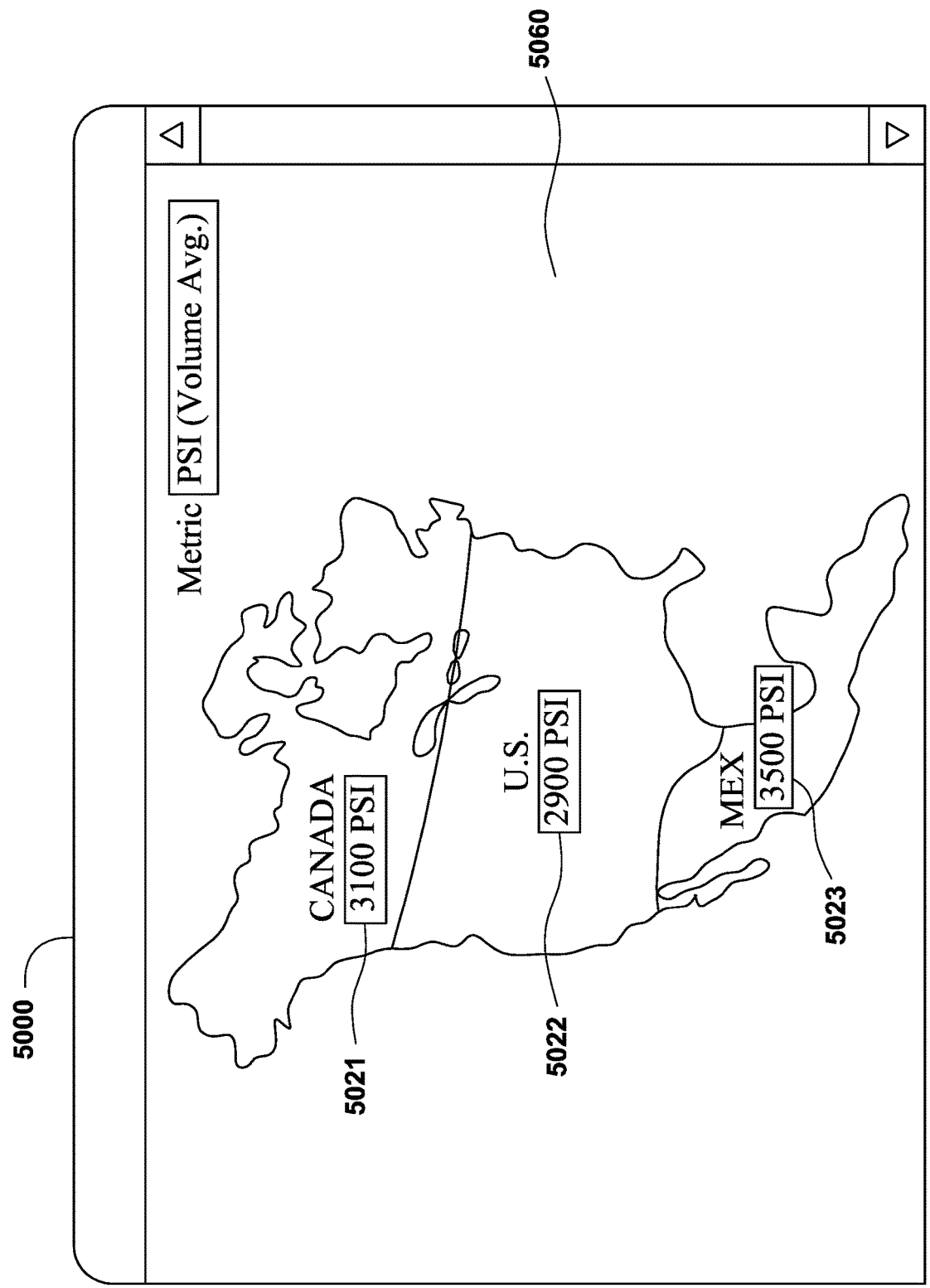
FIG. 50 shows a map showing a plurality of nations and information related to construction projects within the nations in accordance with an embodiment.

FIG. 50 shows a map showing a plurality of nations and information related to construction projects within the nations in accordance with an embodiment. Specifically, page 5000 includes a map 5060 of Canada, the United States, and Mexico. Page 5000 includes a statistic 5021 indicating that the volume average PSI value of construction projects within Canada is 3100, a statistic 5022 indicating that the volume average PSI value of construction projects within the United States is 2900 PSI, and a statistic 5023 indicating that the volume average PSI value of construction projects within Mexico is 3500.

In other embodiments, methods, devices, and systems described herein may be used to determine a build rate based on other characteristics. For example, a build rate may be determined based on measurements of temperature of a concrete mixture obtained by sensor devices embedded at various locations, and on changes in the temperature measurements.

In another embodiment, methods, devices, and systems similar to those described herein may be used to determine a build rate based on a change in the strength of a plurality of signals received from a plurality of sensors located at various locations. For example, a Wi-Fi station located at a construction site may receive a plurality of signals from a plurality of sensor devices at various locations at the site. The signals received by the WiFi station may be observed to detect changes in signal strength. It has been observed that the strength of a signal received from a transmitting sensor device decreases after the sensor device is embedded in, or covered by, a concrete mixture. For example, in some concrete mixtures, every one inch of depth corresponds to a decrease of 5-7 decibels in the level of strength of the signal received from the sensor device. Thus, a sensor device that is not (yet) covered by concrete may produce a signal having a particular strength. After a sensor device is covered by concrete, the signal strength may decrease, and then continue to decrease as more concrete is poured, at a rate that enables an observer to identify when the concrete was poured at that location, the depth of the concrete at that location, etc. Thus, changes in signal strength may be analyzed to determine when concrete has been poured at various locations (associated with respective sensors), and a build rate may be determined.

Accordingly, in accordance with an embodiment, a method is provided. A plurality of sensor devices are placed at a plurality of locations at which a concrete mixture is to be poured, wherein each sensor device is adapted to measure a characteristic related to the concrete mixture. The concrete mixture is poured at the plurality of locations. Data representing measurements of the characteristic are received from the plurality of sensor devices. For each of the plurality of sensor devices, a respective change in the characteristic and a respective time associated with the change are determined, thereby determining a plurality of changes and a plurality of corresponding times. A build rate for the construction project is determined based on the plurality of changes and a plurality of corresponding times.

The characteristic may be humidity, temperature, or a decibel level of a signal.

In one embodiment, the characteristic is humidity, and the change is a spike in humidity measurements.

In another embodiment, the characteristic is a decibel level of a signal, and the change is a decrease in the decibel level of the signal.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
    placing a plurality of sensor devices at a plurality of locations at a construction site where a concrete mixture is to be poured, wherein the plurality of sensor devices comprises at least two sensor devices adapted to measure temperature, the plurality of sensor devices including a first sensor device adapted to measure temperature disposed at a first location at the construction site and a second sensor device adapted to measure temperature disposed at a second location at the construction site;
    pouring the concrete mixture over the plurality of sensor devices at the plurality of locations;
    receiving first data representing first temperature measurements from the first sensor device;
    detecting a first change in temperature and a first point in time associated with the first change in temperature, based on the first data;
    receiving second data representing second temperature measurements from the second sensor device;
    detecting a second change in temperature and a second point in time associated with the second change in temperature, based on the second data;
    determining a time period between a first time when concrete was poured over the first sensor device at the first location and a second time when concrete was poured over the second sensor device at the second location, based on the first point in time associated with the first change in temperature and the second point in time associated with the second change in temperature; and
    determining, based at least on the time period determined based on the first point in time associated with the first change in temperature detected based on the first data received from the first sensor device and the second point in time associated with the second change in temperature detected based on the second data received from the second sensor device, a rate at which the concrete mixture is poured over a distance between the first and second sensor devices, wherein the rate is a build rate equal to the distance divided by the time period.

2. The method of claim 1, further comprising:
    placing the plurality of sensors in a form located at the construction site.

3. The method of claim 2, wherein the form is associated with a component of a multi-level structure.

4. The method of claim 1, the method further comprising:
    causing a user device to display, on a display device, a graphic representation of a structure at the construction site and a value representing the rate.

* * * * *